US010336740B2

(12) United States Patent
Learmonth et al.

(10) Patent No.: US 10,336,740 B2
(45) Date of Patent: Jul. 2, 2019

(54) NITROCATECHOL DERIVATIVES AS COMT INHIBITORS

(71) Applicant: BIAL—PORTELA & CA, S.A., S. Mamede Do Coronado (PT)

(72) Inventors: David Alexander Learmonth, Alfena (PT); Laszlo Erno Kiss, S. Mamede Do Coronado (PT); Pedro Nuno Leal Palma, Leca Da Palmeira (PT); Humberto dos Santos Ferreira, Maia (PT); Patricio Manuel V. A. Soares Da Silva, Oporto (PT)

(73) Assignee: BIAL—PORTELA & CA, S.A., S. Mamede do Coronado (PT)

( * ) Notice: Subject to any disclaimer, the term of this patent is extended or adjusted under 35 U.S.C. 154(b) by 0 days.

(21) Appl. No.: 15/402,607

(22) Filed: Jan. 10, 2017

(65) Prior Publication Data
US 2017/0362213 A1 Dec. 21, 2017

Related U.S. Application Data

(63) Continuation of application No. 14/541,654, filed on Nov. 14, 2014, now Pat. No. 9,550,759, which is a continuation of application No. 13/442,356, filed on Apr. 9, 2012, now Pat. No. 8,907,099, which is a continuation of application No. 11/989,447, filed as application No. PCT/PT2006/000020 on Jul. 26, 2006, now Pat. No. 8,168,793.

(30) Foreign Application Priority Data

Jul. 26, 2005 (GB) .................... 0515327.5
Apr. 20, 2006 (EP) .................... 06008203
May 30, 2006 (EP) .................... 06011073

(51) Int. Cl.
*C07D 413/14* (2006.01)
*A61K 31/4412* (2006.01)
*C07D 213/89* (2006.01)
*C07D 215/60* (2006.01)
*C07D 271/06* (2006.01)
*C07D 271/107* (2006.01)
*C07D 401/04* (2006.01)
*C07D 405/04* (2006.01)
*C07D 413/04* (2006.01)
*C07D 413/06* (2006.01)
*C07D 413/12* (2006.01)
*C07D 417/04* (2006.01)

(52) U.S. Cl.
CPC ........ *C07D 413/14* (2013.01); *A61K 31/4412* (2013.01); *C07D 213/89* (2013.01); *C07D 215/60* (2013.01); *C07D 271/06* (2013.01); *C07D 271/107* (2013.01); *C07D 401/04* (2013.01); *C07D 405/04* (2013.01); *C07D 413/04* (2013.01); *C07D 413/06* (2013.01); *C07D 413/12* (2013.01); *C07D 417/04* (2013.01)

(58) Field of Classification Search
CPC .. C07D 413/14; C07D 213/89; C07D 215/60; C07D 271/06; C07D 271/107; C07D 401/04; C07D 405/04; C07D 413/04; C07D 413/06; C07D 413/12; C07D 417/04; A61K 31/4412
See application file for complete search history.

(56) References Cited

U.S. PATENT DOCUMENTS

| 1,532,178 | A | 4/1925 | Godbold |
| 3,647,809 | A | 3/1972 | Reiter et al. |
| 4,065,563 | A | 12/1977 | Narayanan et al. |
| 4,264,573 | A | 4/1981 | Powell et al. |
| 4,386,668 | A | 6/1983 | Parish |
| 4,963,590 | A | 10/1990 | Backstrom et al. |
| 5,236,952 | A | 8/1993 | Bernauer et al. |
| 5,476,875 | A | 12/1995 | Bernauer et al. |
| 5,633,371 | A | 5/1997 | Bernauer et al. |
| 5,705,703 | A | 1/1998 | Bernauer et al. |
| 5,840,769 | A | 11/1998 | Kolter et al. |
| 6,206,110 | B1 | 3/2001 | Slaughter, Jr. et al. |
| 6,500,867 | B1 | 12/2002 | Virkki et al. |
| 6,509,363 | B2 | 1/2003 | Salituro et al. |
| 6,512,136 | B1 | 1/2003 | Benes et al. |
| 6,660,753 | B2 | 12/2003 | Van Wagenen et al. |
| 7,041,685 | B2 | 5/2006 | Cai et al. |
| 7,112,595 | B2 | 9/2006 | Wagenen et al. |
| 7,144,876 | B2 | 12/2006 | Cai et al. |
| 7,317,029 | B2 | 1/2008 | Cai et al. |
| 7,435,750 | B2 | 10/2008 | Cai et al. |
| 7,553,964 | B2 | 6/2009 | Liu et al. |

(Continued)

FOREIGN PATENT DOCUMENTS

CN 1340500 A 3/2002
CN 1173926 C 11/2004
(Continued)

OTHER PUBLICATIONS

Masjost et al. (Chem. Eur. J., 2000, 6: p. 971-982).*
(Continued)

*Primary Examiner* — Robert H Havlin
(74) *Attorney, Agent, or Firm* — McCarter & English, LLP; Steven G. Davis; Wei Song

(57) ABSTRACT

New compounds of formula I are described. The compounds have potentially valuable pharmaceutical properties in the treatment of some central and peripheral nervous system disorders.

16 Claims, No Drawings

(56) References Cited

U.S. PATENT DOCUMENTS

| | | | |
|---|---|---|---|
| 8,168,793 B2 | 5/2012 | Learmonth et al. | |
| 8,524,746 B2 | 9/2013 | Learmonth et al. | |
| 8,536,203 B2 | 9/2013 | Learmonth et al. | |
| 8,907,099 B2 | 12/2014 | Learmonth et al. | |
| 8,975,410 B2 | 3/2015 | Learmonth et al. | |
| 9,126,988 B2 | 9/2015 | Russo et al. | |
| 9,446,012 B2 | 9/2016 | Learmonth et al. | |
| 9,550,759 B2 | 1/2017 | Learmonth et al. | |
| 9,630,955 B2 | 4/2017 | Russo et al. | |
| 9,745,290 B2 | 8/2017 | Learmonth et al. | |
| 2002/0012701 A1 | 1/2002 | Kolter et al. | |
| 2003/0055085 A1 | 3/2003 | Wagenen et al. | |
| 2004/0097555 A1 | 5/2004 | Ohkawa et al. | |
| 2004/0138281 A1 | 7/2004 | Wikstrom et al. | |
| 2004/0171645 A1 | 9/2004 | Bartoszyk et al. | |
| 2006/0019956 A1 | 1/2006 | Green | |
| 2006/0160812 A1 | 7/2006 | Schubert et al. | |
| 2006/0173074 A1 | 8/2006 | Ellmen et al. | |
| 2006/0257473 A1 | 11/2006 | Puranajoti | |
| 2007/0013830 A1 | 1/2007 | Hayakawa | |
| 2007/0026054 A1 | 2/2007 | Theobald et al. | |
| 2007/0048384 A1 | 3/2007 | Rosenberg et al. | |
| 2007/0078133 A1 | 4/2007 | Liu et al. | |
| 2007/0117165 A1 | 5/2007 | Presnell et al. | |
| 2007/0219187 A1 | 9/2007 | Bessis et al. | |
| 2007/0299110 A1 | 12/2007 | Gagliardi et al. | |
| 2008/0051441 A1 | 2/2008 | Brown et al. | |
| 2008/0071184 A1 | 3/2008 | Carter | |
| 2008/0167286 A1 | 7/2008 | Gopalakrishnan et al. | |
| 2008/0269236 A1 | 10/2008 | Ji et al. | |
| 2009/0000437 A1 | 1/2009 | Johnson et al. | |
| 2009/0054437 A1 | 2/2009 | Learmonth et al. | |
| 2009/0111778 A1 | 4/2009 | Apodaca et al. | |
| 2009/0162283 A1 | 6/2009 | Bando et al. | |
| 2009/0227626 A1 | 9/2009 | Deraeve et al. | |
| 2009/0312347 A1 | 12/2009 | Dahl et al. | |
| 2010/0004284 A1 | 1/2010 | Farina et al. | |
| 2010/0113529 A1 | 5/2010 | Learmonth et al. | |
| 2010/0168113 A1 | 7/2010 | Learmonth et al. | |
| 2010/0256193 A1 | 10/2010 | Cardoso de Vasconcelos et al. | |
| 2010/0256194 A1 | 10/2010 | Cardoso de Vasconcelos et al. | |
| 2010/0266193 A1 | 10/2010 | Park | |
| 2011/0014282 A1 | 1/2011 | de Vasconcelos | |
| 2011/0112301 A1 | 5/2011 | Learmonth et al. | |
| 2011/0301204 A1 | 12/2011 | de Almeida et al. | |
| 2012/0196904 A1 | 8/2012 | Learmonth et al. | |
| 2013/0324578 A1 | 12/2013 | Soares da Silva et al. | |
| 2013/0331416 A1 | 12/2013 | Learmonth et al. | |
| 2014/0024682 A1 | 1/2014 | Learmonth et al. | |
| 2014/0045900 A1 | 2/2014 | Soares da Silva et al. | |
| 2014/0350057 A1 | 11/2014 | Russo et al. | |
| 2015/0072977 A1 | 3/2015 | Learmonth et al. | |
| 2015/0166519 A1 | 6/2015 | Learmonth | |
| 2015/0359583 A1 | 12/2015 | de Vasconcelos et al. | |
| 2016/0009699 A1 | 1/2016 | Learmonth et al. | |
| 2016/0009700 A1 | 1/2016 | Russo et al. | |
| 2017/0340593 A1 | 11/2017 | Soares da Silva et al. | |

FOREIGN PATENT DOCUMENTS

| | | |
|---|---|---|
| DE | 3740383 A1 | 6/1988 |
| EP | 0237929 A1 | 9/1987 |
| EP | 0372654 A2 | 6/1990 |
| EP | 0462639 A1 | 12/1991 |
| EP | 0487774 A1 | 6/1992 |
| EP | 1167342 A1 | 1/2002 |
| EP | 1 845 097 A1 | 10/2007 |
| EP | 1 881 979 A1 | 1/2008 |
| FR | 1260080 A | 5/1961 |
| JP | H10-67651 A | 3/1998 |
| JP | 2002-020319 A | 1/2002 |
| JP | 2003-116966 A | 4/2003 |
| WO | 1993/13083 A1 | 7/1993 |
| WO | 00/37423 A1 | 6/2000 |
| WO | 01/12627 A1 | 2/2001 |
| WO | 2001/68083 A1 | 9/2001 |
| WO | 02/051442 A1 | 7/2002 |
| WO | 02/068417 A2 | 9/2002 |
| WO | 2002/096867 A2 | 12/2002 |
| WO | 2002/100826 A2 | 12/2002 |
| WO | 2004/058163 A2 | 7/2004 |
| WO | 2005/013982 A1 | 2/2005 |
| WO | 2005/044797 A1 | 5/2005 |
| WO | 2005/105780 A2 | 11/2005 |
| WO | 2006/061697 A1 | 6/2006 |
| WO | 2006/071184 A1 | 7/2006 |
| WO | 2006/114400 A1 | 11/2006 |
| WO | 2006/129199 A1 | 12/2006 |
| WO | 2006/132914 A2 | 12/2006 |
| WO | 2007/013830 A1 | 2/2007 |
| WO | 2007/034024 A2 | 3/2007 |
| WO | 2007/113276 A1 | 10/2007 |
| WO | 2007/117165 A1 | 10/2007 |
| WO | 2008/021388 A1 | 2/2008 |
| WO | 2008/094053 A1 | 8/2008 |
| WO | 2009/029632 A1 | 3/2009 |
| WO | 2010/014025 A1 | 2/2010 |
| WO | 2011/107653 A2 | 9/2011 |
| WO | 2012/107708 A1 | 8/2012 |

OTHER PUBLICATIONS

Kubinyi (3D QSAR in Drug Design: Ligand-Protein Interactions and Molecular Similarity, vol. 2-3, Springer, 1998, 800 pages). pp. 243-244 provided.*

Wermuth, The Practice of Medicinal Chemsitry, 2d ed. (2003), 768 pages. Chs. 9-10 provided.*

[No Author Listed] "[1,2,4]-oxadazolyl nitrocatechol derivatives" IP.com Journal, IP.com Inc., West Henrietta, AY, US, May 3, 2012. XP013150541.

[No Author Listed] COMT inhibitor definition from Wikipedia, retrieved from http://en.wikipedia.org/w/index.php?title=COMT_inhibitor&oldid=478541384, last accessed Jan. 31, 2014.

Al-Mousawi, S.M. et al., "Alkylazinylcarbonitriles as building blocks in heterocyclic synthesis: a route for the synthesis of 4-methyl-2-oxopyridines," Pharmazie, 54, 8, pp. 571-574 (1999).

Al-Omran, F. et al., "Heterocyclic Synthesis via Enaminones: Novel Synthesis of (1 H)-Pyridin-2-one, Pyrazolo [1 ,5-?]pyrimidine and Isoxazole Derivatives Incorporating a N-Methylphthalimide and Their Biological Evaluation", J. Heterocyclic Chem., 42, pp. 307-312 (2005).

Ansel et al., Pharmaceutical Dosage Forms and Drug Delivery Systems, 6th edition, 1995. pp. 192-201.

Bondvalli et al., "An Efficient Synthesis of Functionalized 2-Pyridones by Direct Route or via Amide/Enolate Ammonium Salt Intermediates", Synthesis, No. 7, pp. 1169-1174 (1999).

Davies, Ian W. et al., "A General [ 3 + 2 + 1] Annulation Strategy for the Preparation of Pyridine N-Oxides", Organic Letters, vol. 3, No. 2, pp. 209-211 (2001).

Dmitriyeva et al. "Features of the reaction of some 2-chloronicotinonitriles with hydroxylamine. Synthesis of 3-(1, 2, 4-oxadiazol-3yl)pyridines and their fragmentation under electron impact." IzvestiyaVysshikh UchehnykhZavedenii, Khimiya i Khimicheskaya Tekhnologiya, 2005, vol. 48, No. 11, pp. 15-17, CAPLUS Abstract, ON 145:103612.

Dutrow, B. "X-ray Powder Diffraction," excerpt, http://serc.carleton.edu/research_education/geochemsheets/techniques/XRD.html posted Aug. 2008, retrieved from Internet Archive Wayback Machine May 11, 2016.

English translation of JP 2003-116966.

EPO Search Report and Written Opinion—EP 06075343 Date of completion of the search Mar. 28, 2006, 5 pages.

Girges et al., (Chemical Papers (1992), 46(4), 272-277).

Grosset, D.G. et al., Parkinson's Disease, Clinician's Desk Reference, Manson Publishing, 2009, p. 62.

Howse, "Brocresine in Parkinson's disease, Action of a peripheral and central decarboxylase inhibitor in potentiating levodopa," Journal of Neurology, Neurosurgery, and Psychiatry, 1973,36, pp. 27-29.

(56) References Cited

OTHER PUBLICATIONS

International Preliminary Report on Patentability for PCT/PT2006/000020, dated Jan. 29, 2008.
International Preliminary Report on Patentability for PCT/PT2007/000016, dated Oct. 14, 2008.
International Preliminary Report on Patentability for PCT/PT2007/000043, dated Aug. 4, 2009.
International Preliminary Report on Patentability for PCT/PT2009/000044, dated Feb. 10, 2011.
International Search Report and Written Opinion for PCT/PT2006/000020, dated Nov. 8, 2006.
International Search Report and Written Opinion for PCT/PT2007/000016, dated Jul. 13, 2007,12 pages.
International Search Report and Written Opinion for PCT/PT2007/000043, dated Apr. 23, 2008.
International Search Report and Written Opinion for PCT/PT2009/000044, dated Nov. 16, 2009, 16 pages.
Ivanova, L.A., "Technology of dosage forms," Moscow, Medicine, vol. 2, 1991, pp. 223-224. English translation.
Kiss, L. E. et al., "Discovery of a long-acting, peripherally selective inhibitor of a catechol-O-methyltransferase" Journal of Medicinal Chemistry, American Chemical Society, US, vol. 53, No. 8, Apr. 22, 2010, pp. 3396-3411. XP002594266.
Korolkovas, A. "Essentials of Medicinal Chemistry", Development of Drugs, Second Edition, pp. 97-103 and 135-137 (1988).
Kristensen et al., "Granulation A Review on Pharmaceutical Wet-Granulation Drug Development and Industrial Pharmacy", 13(48,5), 803-872 (1987).
Krogsgaard-Larsen, P. et al., "Textbook of Drug Design and Discovery", Third Edition, Table 14.3, pp. 426-427 (2002).
Learmonth, David., et al., "Chemical Synthesis and Characterization of Conjugates of a Novel Catechol-O-methyltransferase Inhibitor", Bioconjugate Chem., vol. 13, pp. 1112-1118, American Chemical Society, 2002.
Marcoux, Jean-Francois et al., "A General Preparation of Pyridines and Pyridones via the Annulation of Ketones and Esters," J. Org. Chem, 66, pp. 4194-4199 (2001).
Morbus Parkinson, Stellenwert von COMT-Hemmern Bestatigt, May 3, 2004, 2 pages.
Nutt, John G., "Catechol-O-methyltransferase inhibitors for treatment of Parkinson's disease", Commentary, vol. 351, pp. 1221-1222, The Lancet, Apr. 1998.
Nutt, John G., et al., "Pharmacokinetics of Levodopa", Clinical Neuropharmacology, vol. 7, No. 1, pp. 35-49, Raven Press, 1984.
Parashos, S.A., et al., "Frequency, Reasons, and Risk Factors of Entacapone Discontinuation in Parkinson Disease", Clin. Neuropharmacol, (2004), vol. 27, No. 3, pp. 119-123.
Pedrosa, R., et al., "Oxidative and non-oxidative mechanisms of neuronal cell death and apoptosis by L-3,4-dihydroxyphenylalanine (L-DPOA) and dopamine", British Journal of Pharmacology, vol. 137, pp. 1305-1313, Nature Publishing Group, 2002.
Poulain, R.F. et al., "Parallel synthesis of 1, 2, 4-oxadiazoles from carboxylic acids using an improved, uranium-based, acitvation", Tetrahedron Letters 42: 1495-1498 (2001).
Rasenack, N et al., "Micron-size drug particles: common and novel micronization techniques", Pharmaceutical Development and Technology, New York, NY, US, vol. 9, No. 1., Jan. 1, 2004, pp. 1-13, XP009055393.
Reches, A., et al., "3-O-Methyldopa inhibits rotations induced by levodopa in rats after unilateral destruction of the higrostriatal pathway", Neurology, (1982), vol. 32, No. 8, pp. 887-888.
Smith, K.S., et al., "In Vitro Metabolism of Tolcapone to Reactive Intermediates: Relevance to Tolcapone Liver Toxicity", Chem. Res. Toxicol., (2003), vol. 16, pp. 123-128.
Soares-Da-Silva, P. et al., "The O-methylated derivative of L-DOPA, 3-O-methyl-L-DOPA, fails to inhibit neuronal and non-neuronal aromatic L-amino acid decarboxylase", Brain Research, (2000), 863, pp. 293-297.
Tervo, Anu J., et al., "A structure-activity relationship study of catechol-O-methyltransferase inhibitors combining molecular docking and 3D QSAR methods", Journal of Computer-Aided Molecular Design, vol. 17, pp. 797-810, Kluwer Academic Publishers, 2003.
Tohgi, Hideo, et al., "The significance of 3-O-methyldopa concentrations in the cerebrospinal fluid in the pathogenesis of wearing-off phenomenon in Parkinson's Disease", Neuroscience Letters, vol. 132, pp. 19-22, Elsevier Scientific Publishers Ireland Lt (1991).
Vieira-Coelho, M.A., et al., "Effects of tolcapone upon soluble and membrane-bound brain and liver catechol-O-methyltransferase", Brain Research, vol. 821, pp. 69-78, Elsevier Science B.V., 1999.
Madopar, Instructions for use, found on-line Jun. 28, 2016; URL:http://www.webvidal.ru/2010/drug/LP_18271.htm; Feb. 2, 2011.
Bioavailability; published Feb. 2, 2011; retrieved from internet Apr. 7, 2016; https://en.wikipedia.org/w/index.php?title=Bioavailability&oldid=411623071>.
Bonifati et al., New, selective catechol-O-methyltransferase inhibitors as therapeutic agents in Parkinson's disease. Pharmacol Ther. Jan. 1999;81(1):1-36.
Bonifácio et al., Brain and peripheral pharmacokinetics of levodopa in the cynomolgus monkey following administration of opicapone, a third generation nitrocatechol COMT inhibitor. Neuropharmacology. Feb. 2014;77:334-41.
Caplus Accession No. 2003:365244. Preparation of substituted benzamide derivatives as inhibitors of phosphodiesterase IV. 1 page. (2010).
Costa et al., Opicapone long-term efficacy and safety in Parkinson's disease BIPARK-II study: a one-year open-label follow-up. European Journal of Neurology. 2014;21(Suppl. 1):171. Abstract No. eP1259.
Ferreira et al., Effect of opicapone multiple-dose regimens on levodopa pharmacokinetics, motor response, and erythrocyte-COMT activity in Parkinson's patients co-administered with levodopa/dopa-decarboxylase inhibitor. Journal of Neurological Sciences. 2013;333:e116. vol. 333, Abstract No. 1034.
Kubinyi, 3D QSAR in Drug Design, Theory Methods and Applications. Kluwer/Escom, pp. 243-244, (1998).
Lees et al., Efficacy and safety of opicapone, a new COMT-inhibitor, for the treatment of motor fluctuations in Parkinson's Disease patients: BIPARK-II study. Journal of Neurological Sciences. 2013;333:e116. Abstract No. 1038.
Masjost et al., Structure-Based Design, Synthesis, and in vitro Evaluation of Bisubstrate Inhibitors for Catechol O-Methyltransferase (COMT). Chem Eur J. 2000;6(6):971-982.
Reagan-Shaw et al., Dose translation from animal to human studies revisited. FASEB J. Mar. 2008;22(3):659-61.
Wermuth, The Practice of Medicinal Chemistry, 2nd Edition. Chapters 9-10, pp. 131-145, 147-157 (2003).
Wikberg et al., Identification of major metabolites of the catechol-O-methyltransferase inhibitor entacapone in rats and humans. Drug Metab Dispos. Jan.-Feb. 1993;21(1):81-92.
Wikipedia. Bioavailability. retrieved online at: https://en.wikipedia.org/w/index.php?title=Bioavailability&oldid=411623071> Oct. 24, 2016. 7 pages.

\* cited by examiner

NITROCATECHOL DERIVATIVES AS COMT INHIBITORS

This application is a continuation of U.S. application Ser. No. 14/541,654, filed on Nov. 14, 2014 and now U.S. Pat. No. 9,550,759, which, in turn, is a continuation of U.S. application Ser. No. 13/442,356, filed on Apr. 9, 2012 and now U.S. Pat. No. 8,907,099, which, in turn, is a continuation of U.S. application Ser. No. 11/989,447, filed on Jan. 24, 2008 and now U.S. Pat. No. 8,168,793, which, in turn, is the U.S. National Stage of International Application No. PCT/PT2006/000020, filed on Jul. 26, 2006 and claims priority under 35 U.S.C. § 119 or 365 to European Application No. 06011073.1, filed on May 30, 2006; European Application No. 06008203.9, filed on Apr. 20, 2006; and United Kingdom Application No. 0515327.5, filed on Jul. 26, 2005. The entire contents of each of the aforementioned applications are incorporated herein by reference.

This invention relates to novel substituted nitrocatechols, their use in the treatment of some central and peripheral nervous system disorders and pharmaceutical compositions containing them.

Despite being used in clinical practice for several decades, levodopa (L-DOPA) continues to be the gold standard drug for the symptomatic treatment of Parkinson's disease. This has helped to maintain keen interest in the development of inhibitors of the enzyme catechol-O-methyltransferase (COMT) based on the hypothesis that inhibition of this enzyme may provide clinical improvements in patients afflicted by Parkinson's disease undergoing treatment with L-DOPA and a peripheral amino acid decarboxylase (AADC) inhibitor. The rationale for the use of COMT inhibitors as adjuncts to L-DOPA/AADC therapy is based on their ability to reduce metabolic O-methylation of L-DOPA to 3-O-methyl-L-DOPA (3-OMD). The duration of L-DOPA induced clinical improvement is brief as a result of the short in vivo half-life of L-DOPA which contrasts with the long half-life of 3-OMD. Additionally, 3-OMD competes with L-DOPA for transport across the blood-brain barrier (BBB), which means that only a very limited amount of an orally administered dose of L-DOPA actually reaches the site of action, i.e. the brain. Commonly, within only a few years of starting L-DOPA therapy with the usual dosage regime, L-DOPA induced clinical improvement declines at the end of each dose cycle, giving rise to the so-called 'wearing-off' pattern of motor fluctuations. A close relationship between the 'wearing-off' phenomenon and accumulation of 3-OMD has been described (Tohgi, H., et al., Neurosci. Letters, 132:19-22, 1992). It has been speculated that this may result from impaired brain penetration of L-DOPA due to competition for the transport system across the BBB with 3-OMD (Reches, A. et al., Neurology, 32:887-888, 1982) or more simply that there is less L-DOPA available to reach the brain (Nutt, J. G., Fellman, J. H., Clin. Neuropharmacol., 7:35-49, 1984). In effect, COMT inhibition protects L-DOPA from metabolic breakdown in the periphery through O-methylation, such that with repeated doses of L-DOPA, the mean plasma L-DOPA concentration is raised. In addition to reduced competition for transport into the brain, a significantly greater percentage of the orally administered dose of L-DOPA is able to reach the site of action. Thus COMT inhibition serves to increase the bioavailability of L-DOPA and the duration of antiparkinsonian action is prolonged with single doses of L-DOPA (Nutt, J. G., Lancet, 351:1221-1222, 1998).

The most potent COMT inhibitors thusfar reported are 3,4-dihydroxy-4'-methyl-5-nitrobenzophenone (Tolcapone, Australian pat. AU-B-69764/87), (E)-2-cyano-N,N-diethyl-3-(3,4-dihydroxy-5-nitrophenyl)acrylamide (Entacapone, German pat. DE 3740383 A1) and BIA 3-202 (American U.S. Pat. No. 6,512,136) which all have inhibition constants in the low nanomolar range. Although sharing essentially the same pharmacophore, tolcapone differs from entacapone and BIA 3-202 in that it easily enters the central nervous systems (CNS) and is able to inhibit cerebral COMT as well as peripheral COMT. It could be speculated that central inhibition may be less important if the more significant action of inhibiting COMT is to prevent breakdown of L-DOPA in the periphery. Indeed, the use of COMT inhibitors which do not penetrate into the brain at clinically relevant doses may avoid potential undesired CNS side-effects of these agents.

Another serious issue which has emerged since these COMT inhibitors were introduced into clinical practice relates to the potential of these nitrocatechol-based xenobiotics to cause severe liver damage (hepatotoxicity). Indeed, shortly after its launch, tolcapone was withdrawn from the market after several cases of hepatotoxicity were reported including three unfortunate deaths from fatal fulminant hepatitis. Today tolcapone can only be used in Parkinsonian patients who are unresponsive to other treatments and strictly only with regular monitoring of liver function, which is expensive and inconvenient for the patient. Although the actual mechanistic causes of the liver toxicity associated with tolcapone are not fully understood, in vitro studies have shown that tolcapone may be reduced metabolically to reactive intermediates and it has been speculated that these may form covalent adducts with hepatic proteins resulting in hepatocellular injury (Smith, K. S. et al, Chem. Res. Toxicol., 16:123-128, 2003).

Entacapone on the other hand, although sharing the same nitrocatechol pharmacophore with tolcapone, is not associated with liver toxicity and is generally regarded as a safe drug. Unfortunately however, entacapone is a significantly less potent COMT inhibitor than tolcapone and has a much shorter in-vivo half-life. This means that entacapone has a very limited duration of effect and as a consequence, the drug must be administered in very high doses with every dose of L-DOPA taken by the patient. As such, the clinical efficacy of entacapone has been questioned—indeed a recent study (Parashos, S. A. et al., Clin. Neuropharmacol., 27(3): 119-123, 2004) revealed that the principal reason for discontinuation of entacapone treatment in Parkinson's disease patients was a perceived lack of efficacy.

In summary, there still remains a clear clinical requirement for a safe and effective COMT inhibitor for adjunctive therapy in the management of the symptoms of Parkinson's disease. Preferably, the COMT inhibitor should be endowed with greater potency and duration of COMT inhibition than entacapone, which would lead to greater clinical efficacy. More preferably, the COMT inhibitor should, unlike tolcapone, have limited access to the CNS, i.e. it should preferentially inhibit peripheral COMT rather than central COMT. Even more preferably, the COMT inhibitor should combine the aforementioned features and in addition should not be endowed with potential to cause liver toxicity as seen with tolcapone.

We have now surprisingly found that certain nitrocatechols are very potent COMT inhibitors which are also devoid of, or have greatly reduced, toxicity risk. Furthermore, it has been unexpectedly ascertained that it is the chemical functionality of the non-catecholic substituent connected to the heterocyclic ring that determines the lack of toxic effects of the compounds.

To date, there has been only one reported example of a nitrocatecholic [1,2,4]-oxadiazole in the prior art (Example 75 of Australian pat. AU-B-69764/87), this being 5-(3-methyl-1,2,4-oxadiazol-5-yl)-3-nitropyrocatechol 1, which has the chemical structure shown below;

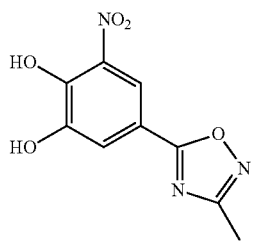

1

This substance is a 3,5-disubstituted-[1,2,4]-oxadiazole with the methyl group occupying position C-3 of the heterocyclic oxadiazolyl ring and the nitrocatecholic pharmacophore attached to C-5.

We have studied the oxadiazolyl compound 1 mentioned above and found it to be moderately active in the COMT inhibition assay (59% of control, see experimental section). Unfortunately however, compound 1 presents a significant toxicity risk (55% cell viability, see experimental section). As such, this particular compound 1 cannot be considered to represent an adequate solution to the present problem of a providing a potent and clinically safe COMT inhibitor.

We have surprisingly found that if the central ring is substituted with a pyridyl ring in oxidised form (i.e. pyridine N-oxide), that the resulting pyridine N-oxide compounds exhibit greatly reduced toxicity, or are even devoid of toxicity risk, whilst it is still concomitantly possible to maintain COMT inhibition superior to entacapone. If the position of the nitrocatechol pharmacophore is 'switched' from C-5 to the C-3 position of the oxadiazole ring, then the resulting compounds are usually less active in terms of COMT inhibition. The regioisomeric 1,3,4-oxadiazoles, wherein the nitrocatechol pharmacophore is attached to C-2 of the oxadiazolyl central ring are also usually less active in terms of COMT inhibition. For example, consider the regioisomers 2 and 3 of the prior art oxadiazole 1 which we have also synthesised and evaluated in vivo;

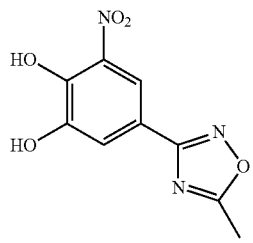

2

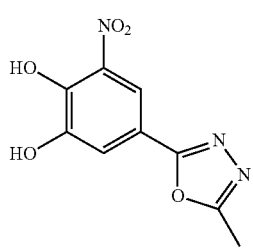

3

Although both 2 and 3 each present a reduced toxicity risk in relation to 1, in terms of COMT inhibition compound 2 displayed only 79% of control and compound 3 was only marginally better at 64%. Thus it can be concluded that it is the combination of the correct positional arrangement of the heteroatoms in the central oxadiazole ring and the incorporation of the pyridine N-oxide functionality is unexpectedly crucial for obtaining synergy between high COMT inhibitory activity and safety for this type of COMT-inhibitor.

Accordingly, the present invention relates to nitrocatecholic COMT inhibitors which are devoid of, or have greatly reduced, toxicity risk. Furthermore, it has been unexpectedly ascertained that it is the introduction of a nitrogen-based heterocyclic group in N-oxidised form, such as, for example, a pyridine N-oxide, that determines the lack of toxic effects of the nitrocatecholic compounds. We have further surprisingly found that compounds of general formula I are COMT inhibitors which are endowed with balanced properties of bioactivity, bioavailability and, in particular, safety:

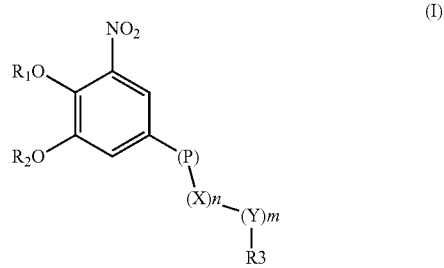

(I)

wherein $R_1$ and $R_2$ are independently from each other hydrogen or a group which is hydrolysable under physiological conditions, optionally substituted lower alkanoyl or aroyl; X represents a methylene group; Y represents an atom of oxygen, nitrogen or sulphur; n represents the number 0, 1, 2 or 3 and m represents the number 0 or 1; $R_3$ represents a pyridine N-oxide group according to the formula A, B or C, which is connected as indicated by the unmarked bond:

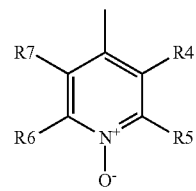

A

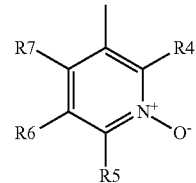

B

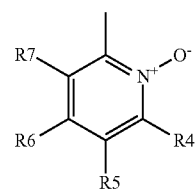

C where $R_4$, $R_5$, $R_6$ and $R_7$ independently from each other represent hydrogen, $C_1$-$C_6$-alkyl, $C_1$-$C_6$-thioalkyl, $C_1$-$C_6$- alkoxy, $C_6$-$C_{12}$-aryloxy or a $C_6$-$C_{12}$-thioaryl group, $C_1$-$C_6$-alkanoyl or $C_7$-$C_{13}$-aroyl group, amino, $C_1$-$C_6$-alkylamino, $C_1$-$C_6$-dialkylamino, $C_3$-$C_{12}$-cycloalkylamino, $C_3$-$C_{12}$-heterocycloalkylamino, $C_1$-$C_6$-alkylsulphonyl, $C_6$-$C_{12}$-arylsulphonyl, halogen, $C_1$-$C_6$-haloalkyl, trifluoromethyl, cyano, nitro or a heteroaryl group; or two or more of residues $R_4$, $R_5$, $R_6$ and $R_7$ taken together represent aliphatic or heteroaliphatic rings or aromatic or heteroaromatic rings and wherein P represents a central unit, which is preferably a planar unit and which is even more preferably selected from the regioisomers of 1,3,4-oxadiazol-2,5-diyl, 1,2,4-oxadiazol-3,5-diyl, 4-methyl-4H-1,2,4-triazol-3,5-diyl, 1,3,5-triazin-2,4-diyl, 1,2,4-triazin-3,5-diyl, 2H-tetrazol-2,5-diyl, 1,2,3-thiadiazol-4,5-diyl, 1-alkyl-3-(alkoxycarbonyl)-1H-pyrrol-2,5-diyl, wherein alkyl is represented by methyl, ethyl, n-propyl and n-butyl and wherein alkoxy is represented by methoxy, ethoxy, n-propoxy and isopropoxy, 1-alkyl-1H-pyrrol-2,5-diyl, wherein alkyl is represented by methyl, ethyl, n-propyl and n-butyl, thiazol-2,4-diyl, 1-H-pyrazol-1,5-diyl, pyrimidin-2,4-diyl, oxazol-2,4-diyl, carbonyl, 1H-imidazol-1,5-diyl, isoxazol-3,5-diyl, furan-2,4-diyl, 3-alkoxycarbonylfuran-2,4-diyl, wherein alkoxy is represented by methoxy, ethoxy, n-propoxy and isopropoxy, benzene-1,3-diyl and (Z)-1-cyanoethen-1,2-diyl.

In the above definition, the regioisomers of the central unit include both regioisomers realizable by exchange of the nitrocatechol moiety and the —(X)$_n$—(Y)$_m$—$R_3$ moiety.

Preferably, $C_1$-$C_6$-alkyl residues represent methyl, ethyl, n-propyl, isopropyl, n-butyl, sec-butyl, tert-butyl, pentyl or hexyl. Preferably, $C_1$-$C_6$-thioalkyl residues represent thiomethyl, thioethyl, thio-n-propyl, thio-isopropyl, thio-n-butyl, thio-n-pentyl and thio-n-hexyl. Preferably, $C_1$-$C_6$-alkoxy residues represent methoxy, ethoxy, n-propoxy, isopropoxy, n-butoxy, sec-butoxy and tert-butoxy. Preferably, $C_6$-$C_{12}$-aryloxy residues represent phenoxy or naphthoxy which may optionally be substituted. Preferably, $C_6$-$C_{12}$-thioaryl residues represent thiophenyl and thionaphthyl which may optionally be substituted. Preferably, $C_1$-$C_6$-alkanoyl residues represent methanoyl, ethanoyl, propanoyl or butanoyl. Preferably, $C_7$-$C_{13}$-aroyl residues represent benzoyl and naphthoyl. Preferably, $C_1$-$C_6$-alkylamino residues represent methylamino, ethylamino, n-propylamino, isopropylamino and n-butylamino. Preferably, $C_1$-$C_6$-dialkylamino residues represent dimethylamino, diethylamino, di-n-propylamino, di-n-butylamino, di-isopropylamino, methylethylamino, methylpropylamino and ethylpropylamino. Preferably, $C_3$-$C_{12}$-cycloalkylamino residues represent pyrrolidino, piperidino, cyclohexylamino and dicyclohexylamino. Preferably, $C_3$-$C_{12}$-heterocycloalkylamino residues represent morpholino, 2,6-dimethylmorpholino, 3,5-dimethylmorpholino, piperazino, N-methylpiperazino and N-ethylpiperazino. Preferably, $C_1$-$C_6$-alkylsulphonyl or $C_6$-$C_{12}$-arylsulphonyl residues represent methylsufonyl, ethylsulfonyl, phenylsulfonyl, and tolylsulfonyl. Preferably, halogen residues represent chloro, bromo, iodo and fluoro. Preferably, $C_1$-$C_6$-haloalkyl represents chloromethyl, fluoromethyl, dichloromethyl, difluoromethyl, trichloromethyl and trifluoromethyl. Preferably, heteroaryl residues represent pyridyl, pyrimidyl, isoxazolyl, oxazolyl, isoxadiazolyl, oxadiazolyl, triazolyl and tetrazolyl. In cases where two or more of residues $R_4$, $R_5$, $R_6$ and $R_7$ taken together represent aliphatic or heteroaliphatic rings or aromatic or heteroaromatic rings, preferred combined residues are indolizinyl, isoindolyl, indolyl, indazolyl, purinyl, quinolizinyl, naphthyridinyl, isoquinolyl and quinolyl.

Preferably, the central unit is selected from a heteroaromatic five-membered ring which includes 1 to 4 of the heteroatoms N, O and S. More preferably, the central unit P is selected from the regioisomers of 1,3,4-oxadiazol-2,5-diyl, 1,2,4-oxadiazol-3,5-diyl, 4-methyl-4H-1,2,4-triazol-3,5-diyl, 1,3,5-triazin-2,4-diyl, 1,2,4-triazin-3,5-diyl, 2H-tetrazol-2,5-diyl, 1,2,3-thiadiazol-4,5-diyl, 1-alkyl-3-(alkoxycarbonyl)-1H-pyrrol-2,5-diyl, wherein alkyl is represented by methyl, ethyl, n-propyl and n-butyl and wherein alkoxy is represented by methoxy, ethoxy, n-propoxy and isopropoxy, 1-alkyl-1H-pyrrol-2,5-diyl, wherein alkyl is represented by methyl, ethyl, n-propyl and n-butyl, thiazol-2,4-diyl, 1-H-pyrazol-1,5-diyl, oxazol-2,4-diyl, carbonyl, 1H-imidazol-1,5-diyl, isoxazol-3,5-diyl, furan-2,4-diyl, 3-alkoxycarbonylfuran-2,4-diyl, wherein alkoxy is represented by methoxy, ethoxy, n-propoxy and isopropoxy.

Most preferably, the central unit P is selected from 1,3,4-oxadiazol-2,5-diyl and 1,2,4-oxadiazol-3,5-diyl.

Preferred compounds of the above general formula (I) having a 1,2,4-oxadiazol-3,5-diyl as central unit include 5-[3-(3,5-dichloro-1-oxy-pyridin-4-yl)-[1,2,4]oxadiazol-5-yl]-3-nitro-benzene-1,2-diol, 5-[3-(2-chloro-1-oxy-pyridin-4-yl)-[1,2,4]oxadiazol-5-yl]-3-nitro-benzene-1,2-diol, 5-[3-(2-morpholin-4-yl-1-oxy-pyridine-4-yl)-[1,2,4]oxadiazol-5-yl]-3-nitro-benzene-1,2-diol, 3-nitro-5-[3-(1-oxy-4-trifluoromethyl-pyridin-3-yl)-[1,2,4]oxadiazol-5-yl]-benzene-1,2-diol, 5-[3-(4-bromo-1-oxy-pyridin-3-yl)-[1,2,4]oxadiazol-5-yl]-3-nitro-benzene-1,2-diol, 5-[3-(2-chloro-6-methyl-1-oxy-pyridin-3-yl)-[1,2,4]oxadiazol-5-yl]-3-nitro-benzene-1,2-diol, 5-[3-(2-morpholin-4-yl-1-oxy-pyridin-3-yl)-[1,2,4]oxadiazol-5-yl]-3-nitro-benzene-1,2-diol, 3-nitro-5-[3-(1-oxy-6-trifluoromethyl-pyridin-3-yl)-[1,2,4]oxadiazol-5-yl]-benzene-1,2-diol, 5-[3-(2-methyl-1-oxy-6-trifluoromethyl-pyridin-3-yl)-[1,2,4]oxadiazol-5-yl]-3-nitro-benzene-1,2-diol, 5-[3-(6-methyl-1-oxy-4-trifluoromethyl-pyridin-3-yl)-[1,2,4]oxadiazol-5-yl]-3-nitro-benzene-1,2-diol, 5-[3-(2,6-dimethyl-1-oxy-4-trifluoromethyl-pyridin-3-yl)-[1,2,4]oxadiazol-5-yl]-3-nitro-benzene-1,2-diol, 5-[3-(2-methyl-1-oxy-6-phenyl-4-trifluoromethyl-pyridin-3-yl)-[1,2,4]oxadiazol-5-yl]-3-nitro-benzene-1,2-diol, 5-[3-(6-methyl-1-oxy-2-phenyl-4-trifluoromethyl-pyridin-3-yl)-[1,2,4]oxadiazol-5-yl]-3-nitro-benzene-1,2-diol, 5-[3-(2-bromo-6-methyl-1-oxy-pyridin-3-yl)-[1,2,4]oxadiazol-5-yl]-3-nitro-benzene-1,2-diol, 5-[3-(2-chloro-4,6-dimethyl-1-oxy-pyridin-3-yl)-[1,2,4]oxadiazol-5-yl]-3-nitro-benzene-1,2-diol, 5-[3-(2-bromo-4,6-dimethyl-1-oxy-pyridin-3-yl)-[1,2,4]oxadiazol-5-yl]-3-nitro-benzene-1,2-diol, 5-[3-(2-bromo-4,5,6-trimethyl-1-oxy-pyridin-3-yl)-[1,2,4]oxadiazol-5-yl]-3-nitrobenzene-1,2-diol, 5-[3-(2-chloro-4,5,6-trimethyl-1-oxy-pyridin-3-yl)-[1,2,4]oxadiazol-5-yl]-3-nitrobenzene-1,2-diol, 5-[3-(2,5-dichloro-4,6-dimethyl-1-oxy-pyridin-3-yl)-[1,2,4]oxadiazol-5-yl]-3-nitrobenzene-1,2-diol, 5-[3-(2-bromo-5-chloro-4,6-dimethyl-1-oxy-pyridin-3-yl)-[1,2,4]oxadiazol-5-yl]-3-nitrobenzene-1,2-diol, and 3-nitro-5-[3-(1-oxy-2-trifluoromethyl-pyridin-3-yl)-[1,2,4]oxadiazol-5-yl]-benzene-1,2-diol, 3-(3-(3,4-dihydroxy-5-nitrophenyl)-1,2,4-oxadiazol-5-yl)-4-(trifluoromethyl)pyridine 1-oxide, 2-chloro-3-(3-(3,4-dihydroxy-5-nitrophenyl)-1,2,4-oxadiazol-5-yl)-4,6-dimethylpyridine 1-oxide, 3-(3-(3,4-dihydroxy-5-nitrophenyl)-1,2,4-oxadiazol-5-yl)-2-methyl-6-(trifluoromethyl)pyridine 1-oxide, 5-(3-(3,4-dihydroxy-5-nitrophenyl)-1,2,4-oxadiazol-5-yl)-2-(trifluoromethyl)pyridine 1-oxide, 5-(3-(3,4-dihydroxy-5-nitrophenyl)-1,2,4-oxadiazol-5-yl)-2-methyl-4-(trifluoromethyl)pyridine 1-oxide, 3-(3-(3,4-dihydroxy-5-nitrophenyl)-1,2,4-oxadiazol-5-yl)-2,6-dimethyl-4-(trifluoromethyl)pyridine 1-oxide, 3,5-dichloro-4-(3-(3,4-dihydroxy-5-nitrophenyl)-1,2,4- oxadiazol-5-yl)pyridine 1-oxide, 3-(3-(3,4-dihydroxy-5-nitrophenyl)-1,2,4-oxadiazol-5-yl)-6-methyl-2-phenyl-4-(trifluoromethyl)pyridine 1-oxide, 2-bromo-3-(3-(3,4-dihydroxy-5-nitrophenyl)-1,2,4-oxadiazol-5-yl)-4,5,6-trimethylpyridine 1-oxide, 2-chloro-3-(3-(3,4-dihydroxy-5-nitrophenyl)-1,2,4-oxadiazol-5-yl)-4,5,6-trimethylpyridine 1-oxide, 3-(3-(3,4-dihydroxy-5-nitrophenyl)-1,2,4-oxadiazol-5-yl)-2-(trifluoromethyl)pyridine 1-oxide, 2,5-dichloro-3-(3-(3,4-dihydroxy-5-nitrophenyl)-1,2,4-oxadiazol-5-yl)-4,6-dimethylpyridine 1-oxide, 3-(3-(3,4-dihydroxy-5-nitrophenyl)-1,2,4-oxadiazol-5-yl)-5-(trifluoromethyl)pyridine 1-oxide, 3-(3-(3,4-dihydroxy-5-nitrophenyl)-1,2,4-oxadiazol-5-yl)-2-fluoropyridine 1-oxide, 4-(3-(3,4-dihydroxy-5-nitrophenyl)-1,2,4-oxadiazol-5-yl)-2-fluoropyridine 1-oxide, 2-(3-(3,4-dihydroxy-5-nitrophenyl)-1,2,4-oxadiazol-5-yl)-6-fluoropyridine 1-oxide, 2-chloro-3-(3-(3,4-dihydroxy-5-nitrophenyl)-1,2,4-oxadiazol-5-yl)-6-methylpyridine 1-oxide, 2-bromo-3-(3-(3,4-dihydroxy-5-nitrophenyl)-1,2,4-oxadiazol-5-yl)-6-methylpyridine 1-oxide, and 2-bromo-5-chloro-3-(3-(3,4-dihydroxy-5-nitrophenyl)-1,2,4-oxadiazol-5-yl)-4,6-dimethylpyridine 1-oxide.

Preferred compounds of the above general formula (I) having a 1,3,4-oxadiazol-2,5-diyl as central unit include 3-(5-(3,4-dihydroxy-5-nitrophenyl)-1,3,4-oxadiazol-2-yl)-4-(trifluoromethyl)pyridine 1-oxide, 2-chloro-3-(5-(3,4-dihydroxy-5-nitrophenyl)-1,3,4-oxadiazol-2-yl)-4,6-dimethylpyridine 1-oxide, 3-(5-(3,4-dihydroxy-5-nitrophenyl)-1,3,4-oxadiazol-2-yl)-2-methyl-6-(trifluoromethyl)pyridine 1-oxide, 5-(5-(3,4-dihydroxy-5-nitrophenyl)-1,3,4-oxadiazol-2-yl)-2-(trifluoromethyl)pyridine 1-oxide, 5-(5-(3,4-dihydroxy-5-nitrophenyl)-1,3,4-oxadiazol-2-yl)-2-methyl-4-(trifluoromethyl)pyridine 1-oxide, 3-(5-(3,4-dihydroxy-5-nitrophenyl)-1,3,4-oxadiazol-2-yl)-2,6-dimethyl-4-(trifluoromethyl)pyridine 1-oxide, 3,5-dichloro-4-(5-(3,4-dihydroxy-5-nitrophenyl)-1,3,4-oxadiazol-2-yl)pyridine 1-oxide, 3-(5-(3,4-dihydroxy-5-nitrophenyl)-1,3,4-oxadiazol-2-yl)-6-methyl-2-phenyl-4-(trifluoromethyl)pyridine 1-oxide, 2-bromo-3-(5-(3,4-dihydroxy-5-nitrophenyl)-1,3,4-oxadiazol-2-yl)-4,5,6-trimethylpyridine 1-oxide, 2-chloro-3-(5-(3,4-dihydroxy-5-nitrophenyl)-1,3,4-oxadiazol-2-yl)-4,5,6-trimethylpyridine 1-oxide, 3-(5-(3,4-dihydroxy-5-nitrophenyl)-1,3,4-oxadiazol-2-yl)-2-(trifluoromethyl)pyridine 1-oxide, 2,5-dichloro-3-(5-(3,4-dihydroxy-5-nitrophenyl)-1,3,4-oxadiazol-2-yl)-4,6-dimethylpyridine 1-oxide, 3-(5-(3,4-dihydroxy-5-nitrophenyl)-1,3,4-oxadiazol-2-yl)-5-(trifluoromethyl)pyridine 1-oxide, 3-(5-(3,4-dihydroxy-5-nitrophenyl)-1,3,4-oxadiazol-2-yl)-2-fluoropyridine 1-oxide, 4-(5-(3,4-dihydroxy-5-nitrophenyl)-1,3,4-oxadiazol-2-yl)-2-fluoropyridine 1-oxide, 2-(5-(3,4-dihydroxy-5-nitrophenyl)-1,3,4-oxadiazol-2-yl)-6-fluoropyridine 1-oxide, 2-chloro-3-(5-(3,4-dihydroxy-5-nitrophenyl)-1,3,4-oxadiazol-2-yl)-6-methylpyridine 1-oxide, 2-bromo-3-(5-(3,4-dihydroxy-5-nitrophenyl)-1,3,4-oxadiazol-2-yl)-6-methylpyridine 1-oxide, and 2-bromo-5-chloro-3-(5-(3,4-dihydroxy-5-nitrophenyl)-1,3,4-oxadiazol-2-yl)-4,6-dimethylpyridine 1-oxide.

Preferred compounds of the above general formula (I) having a 4-methyl-4H-1,2,4-triazol-3,5-diyl as central unit include 3-(5-(3,4-dihydroxy-5-nitrophenyl)-4-methyl-4H-1,2,4-triazol-3-yl)-4-(trifluoromethyl)pyridine 1-oxide, 2-chloro-3-(5-(3,4-dihydroxy-5-nitrophenyl)-4-methyl-4H-1,2,4-triazol-3-yl)-4,6-dimethylpyridine 1-oxide, 3-(5-(3,4-dihydroxy-5-nitrophenyl)-4-methyl-4H-1,2,4-triazol-3-yl)-2-methyl-6-(trifluoromethyl)pyridine 1-oxide, 5-(5-(3,4-dihydroxy-5-nitrophenyl)-4-methyl-4H-1,2,4-triazol-3-yl)-2-(trifluoromethyl)pyridine 1-oxide, 5-(5-(3,4-dihydroxy-5-nitrophenyl)-4-methyl-4H-1,2,4-triazol-3-yl)-2-methyl-4-(trifluoromethyl)pyridine 1-oxide, 3-(5-(3,4-dihydroxy-5-nitrophenyl)-4-methyl-4H-1,2,4-triazol-3-yl)-2,6-dimethyl-4-(trifluoromethyl)pyridine 1-oxide, 3,5-dichloro-4-(5-(3,4-dihydroxy-5-nitrophenyl)-4-methyl-4H-1,2,4-triazol-3-yl)pyridine 1-oxide, 3-(5-(3,4-dihydroxy-5-nitrophenyl)-4-methyl-4H-1,2,4-triazol-3-yl)-6-methyl-2-phenyl-4-(trifluoromethyl)pyridine 1-oxide, 2-bromo-3-(5-(3,4-dihydroxy-5-nitrophenyl)-4-methyl-4H-1,2,4-triazol-3-yl)-4,5,6-trimethylpyridine 1-oxide, 2-chloro-3-(5-(3,4-dihydroxy-5-nitrophenyl)-4-methyl-4H-1,2,4-triazol-3-yl)-4,5,6-trimethylpyridine 1-oxide, 3-(5-(3,4-dihydroxy-5-nitrophenyl)-4-methyl-4H-1,2,4-triazol-3-yl)-2-(trifluoromethyl)pyridine 1-oxide, 2,5-dichloro-3-(5-(3,4-dihydroxy-5-nitrophenyl)-4-methyl-4H-1,2,4-triazol-3-yl)-4,6-dimethylpyridine 1-oxide, 3-(5-(3,4-dihydroxy-5-nitrophenyl)-4-methyl-4H-1,2,4-triazol-3-yl)-5-(trifluoromethyl)pyridine 1-oxide, 3-(5-(3,4-dihydroxy-5-nitrophenyl)-4-methyl-4H-1,2,4-triazol-3-yl)-2-fluoropyridine 1-oxide, 4-(5-(3,4-dihydroxy-5-nitrophenyl)-4-methyl-4H-1,2,4-triazol-3-yl)-2-fluoropyridine 1-oxide, 2-(5-(3,4-dihydroxy-5-nitrophenyl)-4-methyl-4H-1,2,4-triazol-3-yl)-6-fluoropyridine 1-oxide, 2-chloro-3-(5-(3,4-dihydroxy-5-nitrophenyl)-4-methyl-4H-1,2,4-triazol-3-yl)-6-methylpyridine 1-oxide, 2-bromo-3-(5-(3,4-dihydroxy-5-nitrophenyl)-4-methyl-4H-1,2,4-triazol-3-yl)-6-methylpyridine 1-oxide and 2-bromo-5-chloro-3-(5-(3,4-dihydroxy-5-nitrophenyl)-4-methyl-4H-1,2,4-triazol-3-yl)-4,6-dimethylpyridine 1-oxide.

Preferred compounds of the above general formula (I) having a 1,3,5-triazin-2,4-diyl as central unit include 3-(4-(3,4-dihydroxy-5-nitrophenyl)-1,3,5-triazin-2-yl)-4-(trifluoromethyl)pyridine 1-oxide, 3-(4-(3,4-dihydroxy-5-nitrophenyl)-1,3,5-triazin-2-yl)-2-methyl-6-(trifluoromethyl)pyridine 1-oxide, 5-(4-(3,4-dihydroxy-5-nitrophenyl)-1,3,5-triazin-2-yl)-2-(trifluoromethyl)pyridine 1-oxide, 5-(4-(3,4-dihydroxy-5-nitrophenyl)-1,3,5-triazin-2-yl)-2-methyl-4-(trifluoromethyl)pyridine 1-oxide, 3-(4-(3,4-dihydroxy-5-nitrophenyl)-1,3,5-triazin-2-yl)-2,6-dimethyl-4-(trifluoromethyl)pyridine 1-oxide, 3-(4-(3,4-dihydroxy-5-nitrophenyl)-1,3,5-triazin-2-yl)-6-methyl-2-phenyl-4-(trifluoromethyl)pyridine 1-oxide, 3-(4-(3,4-dihydroxy-5-nitrophenyl)-1,3,5-triazin-2-yl)-2-(trifluoromethyl)pyridine 1-oxide, and 3-(4-(3,4-dihydroxy-5-nitrophenyl)-1,3,5-triazin-2-yl)-5-(trifluoromethyl)pyridine 1-oxide.

Preferred compounds of the above general formula (I) having a 1,2,4-triazin-3,5-diyl as a central unit include 3-(5-(3,4-dihydroxy-5-nitrophenyl)-1,2,4-triazin-3-yl)-4-(trifluoromethyl)pyridine 1-oxide, 3-(5-(3,4-dihydroxy-5-nitrophenyl)-1,2,4-triazin-3-yl)-2-methyl-6-(trifluoromethyl)pyridine 1-oxide, 5-(5-(3,4-dihydroxy-5-nitrophenyl)-1,2,4-triazin-3-yl)-2-(trifluoromethyl)pyridine 1-oxide, 5-(5-(3,4-dihydroxy-5-nitrophenyl)-1,2,4-triazin-3-yl)-2-methyl-4-(trifluoromethyl)pyridine 1-oxide, 3-(5-(3,4-dihydroxy-5-nitrophenyl)-1,2,4-triazin-3-yl)-2,6-dimethyl-4-(trifluoromethyl)pyridine 1-oxide, 3-(5-(3,4-dihydroxy-5-nitrophenyl)-1,2,4-triazin-3-yl)-6-methyl-2-phenyl-4-(trifluoromethyl)pyridine 1-oxide, 3-(5-(3,4-dihydroxy-5-nitrophenyl)-1,2,4-triazin-3-yl)-2-(trifluoromethyl)pyridine 1-oxide, 3-(5-(3,4-dihydroxy-5-nitrophenyl)-1,2,4-triazin-3-yl)-5-(trifluoromethyl)pyridine 1-oxide, 4-(5-(3,4-dihydroxy-5-nitrophenyl)-1,2,4-triazin-3-yl)-2-fluoropyridine 1-oxide and 2-(5-(3,4-dihydroxy-5-nitrophenyl)-1,2,4-triazin-3-yl)-6-fluoropyridine 1-oxide.

Preferred compounds of the above general formula (I) having a (Z)-1-cyanoethen-1,2-diyl moiety as central unit include (Z)-3-(1-cyano-2-(3,4-dihydroxy-5-nitrophenyl)vinyl)-4-(trifluoromethyl)pyridine 1-oxide, (Z)-2-chloro-3-(1-cyano-2-(3,4-dihydroxy-5-nitrophenyl)vinyl)-4,6-dimethylpyridine 1-oxide, (Z)-3-(1-cyano-2-(3,4-dihydroxy-5-nitrophenyl)vinyl)-2-methyl-6-(trifluoromethyl)pyridine 1-oxide, (Z)-5-(1-cyano-2-(3,4-dihydroxy-5-nitrophenyl)vinyl)-2-(trifluoromethyl)pyridine 1-oxide, (Z)-5-(1-cyano-2-(3,4-dihydroxy-5-nitrophenyl)vinyl)-2-methyl-4-(trifluoromethyl)pyridine 1-oxide, (Z)-3-(1-cyano-2-(3,4-dihydroxy-5-nitrophenyl)vinyl)-2,6-dimethyl-4-(trifluoromethyl)pyridine 1-oxide, (Z)-3,5-dichloro-4-(1-cyano-2-(3,4-dihydroxy-5-nitrophenyl)vinyl)pyridine 1-oxide, (Z)-3-(1-cyano-2-(3,4-dihydroxy-5-nitrophenyl)vinyl)-6-methyl-2-phenyl-4-(trifluoromethyl)pyridine 1-oxide, (Z)-2-bromo-3-(1-cyano-2-(3,4-dihydroxy-5-nitrophenyl)vinyl)-4,5,6-trimethylpyridine 1-oxide, (Z)-2-chloro-3-(1-cyano-2-(3,4-dihydroxy-5-nitrophenyl)vinyl)-4,5,6-trimethylpyridine 1-oxide, (Z)-3-(1-cyano-2-(3,4-dihydroxy-5-nitrophenyl)vinyl)-2-(trifluoromethyl)pyridine 1-oxide, (Z)-2,5-dichloro-3-(1-cyano-2-(3,4-dihydroxy-5-nitrophenyl)vinyl)-4,6-dimethylpyridine 1-oxide, (Z)-3-(1-cyano-2-(3,4-dihydroxy-5-nitrophenyl)vinyl)-5-(trifluoromethyl)pyridine 1-oxide, (Z)-3-(1-cyano-2-(3,4-dihydroxy-5-nitrophenyl)vinyl)-2-fluoropyridine 1-oxide, (Z)-4-(1-cyano-2-(3,4-dihydroxy-5-nitrophenyl)vinyl)-2-fluoropyridine 1-oxide, (Z)-2-(1-cyano-2-(3,4-dihydroxy-5-nitrophenyl)vinyl)-6-fluoropyridine 1-oxide, (Z)-2-chloro-3-(1-cyano-2-(3,4-dihydroxy-5-nitrophenyl)vinyl)-6-methylpyridine 1-oxide, (Z)-2-bromo-3-(1-cyano-2-(3,4-dihydroxy-5-nitrophenyl)vinyl)-6-methylpyridine 1-oxide, and (Z)-2-bromo-5-chloro-3-(1-cyano-2-(3,4-dihydroxy-5-nitrophenyl)vinyl)-4,6-dimethylpyridine 1-oxide.

Preferred compounds of the above general formula (I) having as central unit a furan-2,4-diyl or a 3-alkoxycarbonylfuran-2,4-diyl moiety, wherein alkoxy is represented by methoxy, ethoxy, n-propoxy and isopropoxy, include 3-(4-(3,4-dihydroxy-5-nitrophenyl)-3-(ethoxycarbonyl)furan-2-yl)-4-(trifluoromethyl)pyridine 1-oxide, 2-chloro-3-(4-(3,4-dihydroxy-5-nitrophenyl)-3-(ethoxycarbonyl) furan-2-yl)-4,6-dimethylpyridine 1-oxide, 3-(4-(3,4-dihydroxy-5-nitrophenyl)-3-(ethoxycarbonyl)furan-2-yl)-2-methyl-6-(trifluoromethyl)pyridine 1-oxide, 5-(4-(3,4-dihydroxy-5-nitrophenyl)-3-(ethoxycarbonyl)furan-2-yl)-2-(trifluoromethyl)pyridine 1-oxide, 5-(4-(3,4-dihydroxy-5-nitrophenyl)-3-(ethoxycarbonyl)furan-2-yl)-2-methyl-4-(trifluoromethyl)pyridine 1-oxide, 5-(4-(3,4-dihydroxy-5-nitrophenyl)-3-(ethoxycarbonyl)furan-2-yl)-2,6-dimethyl-4-(trifluoromethyl)pyridine 1-oxide, 3,5-dichloro-4-(4-(3,4-dihydroxy-5-nitrophenyl)-3-(ethoxycarbonyl)furan-2-yl)pyridine 1-oxide, 3-(4-(3,4-dihydroxy-5-nitrophenyl)furan-2-yl)-6-methyl-2-phenyl-4-(trifluoromethyl)pyridine 1-oxide, 2-bromo-3-(4-(3,4-dihydroxy-5-nitrophenyl)furan-2-yl)-4,5,6-trimethylpyridine 1-oxide, 2-chloro-3-(4-(3,4-dihydroxy-5-nitrophenyl)furan-2-yl)-4,5,6-trimethylpyridine 1-oxide, 3-(4-(3,4-dihydroxy-5-nitrophenyl)furan-2-yl)-2-(trifluoromethyl)pyridine 1-oxide, 2,5-dichloro-3-(4-(3,4-dihydroxy-5-nitrophenyl)furan-2-yl)-4,6-dimethylpyridine 1-oxide, 3-(4-(3,4-dihydroxy-5-nitrophenyl)furan-2-yl)-5-(trifluoromethyl)pyridine 1-oxide, 3-(4-(3,4-dihydroxy-5-nitrophenyl)-3-(ethoxycarbonyl)furan-2-yl)-2-fluoropyridine 1-oxide, 4-(4-(3,4-dihydroxy-5-nitrophenyl)-3-(ethoxycarbonyl)furan-2-yl)-2-fluoropyridine 1-oxide, 2-(4-(3,4-dihydroxy-5-nitrophenyl)-3-(ethoxycarbonyl)furan-2-yl)-6-fluoropyridine 1-oxide, 2-chloro-3-(4-(3,4-dihydroxy-5-nitrophenyl)-3-(ethoxycarbonyl)furan-2-yl)-6-methylpyridine 1-oxide, 2-bromo-3-(4-(3,4-dihydroxy-5-nitrophenyl)-3-(ethoxycarbonyl)furan-2-yl)-6-methylpyridine 1-oxide, and 2-bromo-5-chloro-3-(4-(3,4-dihydroxy-5-nitrophenyl)-3-(ethoxycarbonyl)furan-2-yl)-4,6-dimethylpyridine 1-oxide.

Preferred compounds of the above general formula (I) having as central unit a 1H-imidazol-1,5-diyl moiety include 3-(5-(3,4-dihydroxy-5-nitrophenyl)-1H-imidazol-1-yl)-4-(trifluoromethyl)pyridine 1-oxide, 2-chloro-3-(5-(3,4-dihydroxy-5-nitrophenyl)-1H-imidazol-1-yl)-4,6-dimethylpyridine 1-oxide, 3-(5-(3,4-dihydroxy-5-nitrophenyl)-1H-imidazol-1-yl)-2-methyl-6-(trifluoromethyl)pyridine 1-oxide, 5-(5-(3,4-dihydroxy-5-nitrophenyl)-1H-imidazol-1-yl)-2-(trifluoromethyl)pyridine 1-oxide, 3,5-dichloro-4-(5-(3,4-dihydroxy-5-nitrophenyl)-1H-imidazol-1-yl)pyridine 1-oxide, 3-(5-(3,4-dihydroxy-5-nitrophenyl)-1H-imidazol-1-yl)-2-(trifluoromethyl)pyridine 1-oxide, 3-(5-(3,4-dihydroxy-5-nitrophenyl)-1H-imidazol-1-yl)-5-(trifluoromethyl)pyridine 1-oxide, 3-(5-(3,4-dihydroxy-5-nitrophenyl)-1H-imidazol-1-yl)-2-fluoropyridine 1-oxide, 2-(5-(3,4-dihydroxy-5-nitrophenyl)-1H-imidazol-1-yl)-6-fluoropyridine 1-oxide, 2-chloro-3-(5-(3,4-dihydroxy-5-nitrophenyl)-1H-imidazol-1-yl)-6-methylpyridine 1-oxide, and 2-bromo-3-(5-(3,4-dihydroxy-5-nitrophenyl)-1H-imidazol-1-yl)-6-methylpyridine 1-oxide.

Preferred compounds of the above general formula (I) having as central unit a isoxazol-3,5-diyl moiety include 3-(3-(3,4-dihydroxy-5-nitrophenyl)isoxazol-5-yl)-4-(trifluoromethyl)pyridine 1-oxide, 2-chloro-3-(3-(3,4-dihydroxy-5-nitrophenyl)isoxazol-5-yl)-4,6-dimethylpyridine 1-oxide, 3-(3-(3,4-dihydroxy-5-nitrophenyl)isoxazol-5-yl)-2-methyl-6-(trifluoromethyl)pyridine 1-oxide, 5-(3-(3,4-dihydroxy-5-nitrophenyl)isoxazol-5-yl)-2-(trifluoromethyl)pyridine 1-oxide, 5-(3-(3,4-dihydroxy-5-nitrophenyl)isoxazol-5-yl)-2-methyl-4-(trifluoromethyl)pyridine 1-oxide, 3-(3-(3,4-dihydroxy-5-nitrophenyl)isoxazol-5-yl)-2,6-dimethyl-4-(trifluoromethyl)pyridine 1-oxide, 3,5-dichloro-4-(3-(3,4-dihydroxy-5-nitrophenyl)isoxazol-5-yl)pyridine 1-oxide, 3-(3-(3,4-dihydroxy-5-nitrophenyl)isoxazol-5-yl)-6-methyl-2-phenyl-4-(trifluoromethyl)pyridine 1-oxide, 2-bromo-3-(3-(3,4-dihydroxy-5-nitrophenyl)isoxazol-5-yl)-4,5,6-trimethylpyridine 1-oxide, 2-chloro-3-(3-(3,4-dihydroxy-5-nitrophenyl)isoxazol-5-yl)-4,5,6-trimethylpyridine 1-oxide, 3-(3-(3,4-dihydroxy-5-nitrophenyl)isoxazol-5-yl)-2-(trifluoromethyl)pyridine 1-oxide, 2,5-dichloro-3-(3-(3,4-dihydroxy-5-nitrophenyl)isoxazol-5-yl)-4,6-dimethylpyridine 1-oxide, 3-(3-(3,4-dihydroxy-5-nitrophenyl)isoxazol-5-yl)-5-(trifluoromethyl)pyridine 1-oxide, 3-(3-(3,4-dihydroxy-5-nitrophenyl)isoxazol-5-yl)-2-fluoropyridine 1-oxide, 4-(3-(3,4-dihydroxy-5-nitrophenyl)isoxazol-5-yl)-2-fluoropyridine 1-oxide, 2-(3-(3,4-dihydroxy-5-nitrophenyl)isoxazol-5-yl)-6-fluoropyridine 1-oxide, 2-chloro-3-(3-(3,4-dihydroxy-5-nitrophenyl)isoxazol-5-yl)-6-methylpyridine 1-oxide, 2-bromo-3-(3-(3,4-dihydroxy-5-nitrophenyl)isoxazol-5-yl)-6-methylpyridine 1-oxide, and 2-bromo-5-chloro-3-(3-(3,4-dihydroxy-5-nitrophenyl)isoxazol-5-yl)-4,6-dimethylpyridine 1-oxide.

Preferred compounds of the above general formula (I) having as central unit a carbonyl moiety include 3-(3,4-dihydroxy-5-nitrobenzoyl)-4-(trifluoromethyl)pyridine 1-oxide, 2-chloro-3-(3,4-dihydroxy-5-nitrobenzoyl)-4,6-dimethylpyridine 1-oxide, 3-(3,4-dihydroxy-5-nitrobenzoyl)-2-methyl-6-(trifluoromethyl)pyridine 1-oxide, 5-(3,4-dihydroxy-5-nitrobenzoyl)-2-(trifluoromethyl)pyridine 1-oxide, 5-(3,4-dihydroxy-5-nitrobenzoyl)-2-methyl-4-(trifluoromethyl)pyridine 1-oxide, 3-(3,4-dihydroxy-5-nitrobenzoyl)-2,6-dimethyl-4-(trifluoromethyl)pyridine 1-oxide, 3,5-dichloro-4-(3,4-dihydroxy-5-nitrobenzoyl)pyridine 1-oxide, 3-(3,4-dihydroxy-5-nitrobenzoyl)-6-methyl-2-phenyl-4-(trifluoromethyl)pyridine 1-oxide, 2-bromo-3-(3,4-dihydroxy-5-nitrobenzoyl)-4,5,6-trimethylpyridine 1-oxide, 2-chloro-3-(3,4-dihydroxy-5-nitrobenzoyl)-4,5,6-trimethylpyridine 1-oxide, 3-(3,4-dihydroxy-5-nitrobenzoyl)-2-(trifluoromethyl)pyridine 1-oxide, 2,5-dichloro-3-(3,4-dihydroxy-5-nitrobenzoyl)-4,6-dimethylpyridine 1-oxide, 3-(3,4-dihydroxy-5-nitrobenzoyl)-5-(trifluoromethyl)pyridine 1-oxide, 3-(3,4-dihydroxy-5-nitrobenzoyl)-2-fluoropyridine 1-oxide, 4-(3,4-dihydroxy-5-nitrobenzoyl)-2-fluoropyridine 1-oxide, 2-(3,4-dihydroxy-5-nitrobenzoyl)-6-fluoropyridine 1-oxide, 2-chloro-3-(3,4-dihydroxy-5-nitrobenzoyl)-6-methylpyridine 1-oxide, 2-bromo-3-(3,4-dihydroxy-5-nitrobenzoyl)-6-methylpyridine 1-oxide, and 2-bromo-5-chloro-3-(3,4-dihydroxy-5-nitrobenzoyl)-4,6-dimethylpyridine 1-oxide.

Preferred compounds of the above general formula (I) having as central unit an oxazol-2,4-diyl moiety include 3-(4-(3,4-dihydroxy-5-nitrophenyl)oxazol-2-yl)-4-(trifluoromethyl)pyridine 1-oxide, 2-chloro-3-(4-(3,4-dihydroxy-5-nitrophenyl)oxazol-2-yl)-4,6-dimethylpyridine 1-oxide, 3-(4-(3,4-dihydroxy-5-nitrophenyl)oxazol-2-yl)-2-methyl-6-(trifluoromethyl)pyridine 1-oxide, 5-(4-(3,4-dihydroxy-5-nitrophenyl)oxazol-2-yl)-2-(trifluoromethyl)pyridine 1-oxide, 5-(4-(3,4-dihydroxy-5-nitrophenyl)oxazol-2-yl)-2-methyl-4-(trifluoromethyl)pyridine 1-oxide, 3-(4-(3,4-dihydroxy-5-nitrophenyl)oxazol-2-yl)-2,6-dimethyl-4-(trifluoromethyl)pyridine 1-oxide, 3,5-dichloro-4-(4-(3,4-dihydroxy-5-nitrophenyl)oxazol-2-yl)pyridine 1-oxide, 3-(4-(3,4-dihydroxy-5-nitrophenyl)oxazol-2-yl)-6-methyl-2-phenyl-4-(trifluoromethyl)pyridine 1-oxide, 2-bromo-3-(4-(3,4-dihydroxy-5-nitrophenyl)oxazol-2-yl)-4,5,6-trimethylpyridine 1-oxide, 2-chloro-3-(4-(3,4-dihydroxy-5-nitrophenyl)oxazol-2-yl)-4,5,6-trimethylpyridine 1-oxide, 3-(4-(3,4-dihydroxy-5-nitrophenyl)oxazol-2-yl)-2-(trifluoromethyl)pyridine 1-oxide, 2,5-dichloro-3-(4-(3,4-dihydroxy-5-nitrophenyl)oxazol-2-yl)-4,6-dimethylpyridine 1-oxide, 3-(4-(3,4-dihydroxy-5-nitrophenyl)oxazol-2-yl)-5-(trifluoromethyl)pyridine 1-oxide, 3-(4-(3,4-dihydroxy-5-nitrophenyl)oxazol-2-yl)-2-fluoropyridine 1-oxide, 4-(4-(3,4-dihydroxy-5-nitrophenyl)oxazol-2-yl)-2-fluoropyridine 1-oxide, 2-(4-(3,4-dihydroxy-5-nitrophenyl)oxazol-2-yl)-6-fluoropyridine 1-oxide, 2-chloro-3-(4-(3,4-dihydroxy-5-nitrophenyl)oxazol-2-yl)-6-methylpyridine 1-oxide, 2-bromo-3-(4-(3,4-dihydroxy-5-nitrophenyl)oxazol-2-yl)-6-methylpyridine 1-oxide, and 2-bromo-5-chloro-3-(4-(3,4-dihydroxy-5-nitrophenyl)oxazol-2-yl)-4,6-dimethylpyridine 1-oxide.

Preferred compounds of the above general formula (I) having as central unit an benzene-1,3-diyl moiety include 3-(3',4'-dihydroxy-5'-nitrobiphenyl-3-yl)-4-(trifluoromethyl)pyridine 1-oxide, 5-(3',4'-dihydroxy-5'-nitrobiphenyl-3-yl)-2-(trifluoromethyl)pyridine 1-oxide, 3,5-dichloro-4-(3',4'-dihydroxy-5'-nitrobiphenyl-3-yl)pyridine 1-oxide, 3-(3',4'-dihydroxy-5'-nitrobiphenyl-3-yl)-2-(trifluoromethyl)pyridine 1-oxide, and 3-(3',4'-dihydroxy-5'-nitrobiphenyl-3-yl)-5-(trifluoromethyl)pyridine 1-oxide.

Preferred compounds of the above general formula (I) having as central unit an 1-H-pyrazol-1,5-diyl moiety include 3-(5-(3,4-dihydroxy-5-nitrophenyl)-1H-pyrazol-1-yl)-4-(trifluoromethyl)pyridine 1-oxide, 5-(5-(3,4-dihydroxy-5-nitrophenyl)-1H-pyrazol-1-yl)-2-(trifluoromethyl)pyridine 1-oxide, 3,5-dichloro-4-(5-(3,4-dihydroxy-5-nitrophenyl)-1H-pyrazol-1-yl)pyridine 1-oxide, 3-(5-(3,4-dihydroxy-5-nitrophenyl)-1H-pyrazol-1-yl)-2-(trifluoromethyl)pyridine 1-oxide, 3-(5-(3,4-dihydroxy-5-nitrophenyl)-1H-pyrazol-1-yl)-5-(trifluoromethyl)pyridine 1-oxide, and 4-(5-(3,4-dihydroxy-5-nitrophenyl)-1H-pyrazol-1-yl)-2-fluoropyridine 1-oxide.

Preferred compounds of the above general formula (I) having as central unit an pyrimidin-2,4-diyl moiety include 3-(4-(3,4-dihydroxy-5-nitrophenyl)pyrimidin-2-yl)-4-(trifluoromethyl)pyridine 1-oxide, 2-chloro-3-(4-(3,4-dihydroxy-5-nitrophenyl)pyrimidin-2-yl)-4,6-dimethylpyridine 1-oxide, 3-(4-(3,4-dihydroxy-5-nitrophenyl)pyrimidin-2-yl)-2-methyl-6-(trifluoromethyl)pyridine 1-oxide, 5-(4-(3,4-dihydroxy-5-nitrophenyl)pyrimidin-2-yl)-2-(trifluoromethyl)pyridine 1-oxide, 5-(4-(3,4-dihydroxy-5-nitrophenyl)pyrimidin-2-yl)-2-methyl-4-(trifluoromethyl)pyridine 1-oxide, 3-(4-(3,4-dihydroxy-5-nitrophenyl)pyrimidin-2-yl)-2,6-dimethyl-4-(trifluoromethyl)pyridine 1-oxide, 3,5-dichloro-4-(4-(3,4-dihydroxy-5-nitrophenyl)pyrimidin-2-yl)pyridine 1-oxide, 3-(4-(3,4-dihydroxy-5-nitrophenyl)pyrimidin-2-yl)-6-methyl-2-phenyl-4-(trifluoromethyl)pyridine 1-oxide, 2-bromo-3-(4-(3,4-dihydroxy-5-nitrophenyl)pyrimidin-2-yl)-4,5,6-trimethylpyridine 1-oxide, 2-chloro-3-(4-(3,4-dihydroxy-5-nitrophenyl)pyrimidin-2-yl)-4,5,6-trimethylpyridine 1-oxide, 3-(4-(3,4-dihydroxy-5-nitrophenyl)pyrimidin-2-yl)-2-(trifluoromethyl)pyridine 1-oxide, 2,5-dichloro-3-(4-(3,4-dihydroxy-5-nitrophenyl)pyrimidin-2-yl)-4,6-dimethylpyridine 1-oxide, and 3-(4-(3,4-dihydroxy-5-nitrophenyl)pyrimidin-2-yl)-5-(trifluoromethyl)pyridine 1-oxide.

Preferred compounds of the above general formula (I) having as central unit an 1H-pyrrol-2,5-diyl moiety include 3-(5-(3,4-dihydroxy-5-nitrophenyl)-1-methyl-3-(ethoxycarbonyl)-1H-pyrrol-2-yl)-4-(trifluoromethyl)pyridine 1-oxide, 2-chloro-3-(5-(3,4-dihydroxy-5-nitrophenyl)-3-(ethoxycarbonyl)-1-methyl-1H-pyrrol-2-yl)-4,6-dimethylpyridine 1-oxide, 3-(5-(3,4-dihydroxy-5-nitrophenyl)-1-methyl-1H-pyrrol-2-yl)-2-methyl-6-(trifluoromethyl)pyridine 1-oxide, 5-(5-(3,4-dihydroxy-5-nitrophenyl)-1-ethyl-3-(ethoxycarbonyl)-1H-pyrrol-2-yl)-2-(trifluoromethyl)pyridine 1-oxide, 5-(5-(3,4-dihydroxy-5-nitrophenyl)-1-methyl-1H-pyrrol-2-yl)-2-methyl-4-(trifluoromethyl)pyridine 1-oxide, 3-(5-(3,4-dihydroxy-5-nitrophenyl)-1-methyl-1H-pyrrol-2-yl)-2,6-dimethyl-4-(trifluoromethyl)pyridine 1-oxide, 3,5-dichloro-4-(5-(3,4-dihydroxy-5-nitrophenyl)-1-methyl-1H-pyrrol-2-yl)pyridine 1-oxide, 3-(5-(3,4-dihydroxy-5-nitrophenyl)-1-methyl-1H-pyrrol-2-yl)-6-methyl-2-phenyl-4-(trifluoromethyl)pyridine 1-oxide, 2-bromo-3-(5-(3,4-dihydroxy-5-nitrophenyl)-1-methyl-1H-pyrrol-2-yl)-4,5,6-trimethylpyridine 1-oxide, 2-chloro-3-(5-(3,4-dihydroxy-5-nitrophenyl)-1-methyl-1H-pyrrol-2-yl)-4,5,6-trimethylpyridine 1-oxide, 3-(5-(3,4-dihydroxy-5-nitrophenyl)-1-methyl-1H-pyrrol-2-yl)-2-(trifluoromethyl)pyridine 1-oxide, 2,5-dichloro-3-(5-(3,4-dihydroxy-5-nitrophenyl)-1-methyl-1H-pyrrol-2-yl)-4,6-dimethylpyridine 1-oxide, 3-(5-(3,4-dihydroxy-5-nitrophenyl)-1-methyl-1H-pyrrol-2-yl)-5-(trifluoromethyl)pyridine 1-oxide, 3-(5-(3,4-dihydroxy-5-nitrophenyl)-1-methyl-1H-pyrrol-2-yl)-2-fluoropyridine 1-oxide, 4-(5-(3,4-dihydroxy-5-nitrophenyl)-1-methyl-1H-pyrrol-2-yl)-2-fluoropyridine 1-oxide, 2-(5-(3,4-dihydroxy-5-nitrophenyl)-3-(ethoxycarbonyl)-1-methyl-1H-pyrrol-2-yl)-6-fluoropyridine 1-oxide, 2-chloro-3-(5-(3,4-dihydroxy-5-nitrophenyl)-1-methyl-1H-pyrrol-2-yl)-6-methylpyridine 1-oxide, 2-bromo-3-(5-(3,4-dihydroxy-5-nitrophenyl)-1-methyl-1H-pyrrol-2-yl)-6-methylpyridine 1-oxide, and 2-bromo-5-chloro-3-(5-(3,4-dihydroxy-5-nitrophenyl)-1-methyl-1H-pyrrol-2-yl)-4,6-dimethylpyridine 1-oxide.

Preferred compounds of the above general formula (I) having as central unit an 2H-tetrazol-2,5-diyl moiety include 3-(5-(3,4-dihydroxy-5-nitrophenyl)-2H-tetrazol-2-yl)-4-(trifluoromethyl)pyridine 1-oxide, 5-(5-(3,4-dihydroxy-5-nitrophenyl)-2H-tetrazol-2-yl)-2-(trifluoromethyl)pyridine 1-oxide, 3,5-dichloro-4-(5-(3,4-dihydroxy-5-nitrophenyl)-2H-tetrazol-2-yl)pyridine 1-oxide, 3-(5-(3,4-dihydroxy-5-nitrophenyl)-2H-tetrazol-2-yl)-2-(trifluoromethyl)pyridine 1-oxide, and 3-(5-(3,4-dihydroxy-5-nitrophenyl)-2H-tetrazol-2-yl)-5-(trifluoromethyl)pyridine 1-oxide.

Preferred compounds of the above general formula (I) having as central unit an 1,2,3-thiadiazol-4,5-diyl moiety include 3-(4-(3,4-dihydroxy-5-nitrophenyl)-1,2,3-thiadiazol-5-yl)-4-(trifluoromethyl)pyridine 1-oxide, 2-chloro-3-(4-(3,4-dihydroxy-5-nitrophenyl)-1,2,3-thiadiazol-5-yl)-4,6-dimethylpyridine 1-oxide, 3-(4-(3,4-dihydroxy-5-nitrophenyl)-1,2,3-thiadiazol-5-yl)-2-methyl-6-(trifluoromethyl)pyridine 1-oxide, 5-(4-(3,4-dihydroxy-5-nitrophenyl)-1,2,3-thiadiazol-5-yl)-2-(trifluoromethyl)pyridine 1-oxide, 5-(4-(3,4-dihydroxy-5-nitrophenyl)-1,2,3-thiadiazol-5-yl)-2-methyl-4-(trifluoromethyl)pyridine 1-oxide, 3-(4-(3,4-dihydroxy-5-nitrophenyl)-1,2,3-thiadiazol-5-yl)-2,6-dimethyl-4-(trifluoromethyl)pyridine 1-oxide, 3,5-dichloro-4-(4-(3,4-dihydroxy-5-nitrophenyl)-1,2,3-thiadiazol-5-yl)pyridine 1-oxide, 3-(4-(3,4-dihydroxy-5-nitrophenyl)-1,2,3-thiadiazol-5-yl)-6-methyl-2-phenyl-4-(trifluoromethyl)pyridine 1-oxide, 2-bromo-3-(4-(3,4-dihydroxy-5-nitrophenyl)-1,2,3-thiadiazol-5-yl)-4,5,6-trimethylpyridine 1-oxide, 2-chloro-3-(4-(3,4-dihydroxy-5-nitrophenyl)-1,2,3-thiadiazol-5-yl)-4,5,6-trimethylpyridine 1-oxide, 3-(4-(3,4-dihydroxy-5-nitrophenyl)-1,2,3-thiadiazol-5-yl)-2-(trifluoromethyl)pyridine 1-oxide, 2,5-dichloro-3-(4-(3,4-dihydroxy-5-nitrophenyl)-1,2,3-thiadiazol-5-yl)-4,6-dimethylpyridine 1-oxide, 3-(4-(3,4-dihydroxy-5-nitrophenyl)-1,2,3-thiadiazol-5-yl)-5-(trifluoromethyl)pyridine 1-oxide, 3-(4-(3,4-dihydroxy-5-nitrophenyl)-1,2,3-thiadiazol-5-yl)-2-fluoropyridine 1-oxide, 4-(4-(3,4-dihydroxy-5-nitrophenyl)-1,2,3-thiadiazol-5-yl)-2-fluoropyridine 1-oxide, 2-(4-(3,4-dihydroxy-5-nitrophenyl)-1,2,3-thiadiazol-5-yl)-6-fluoropyridine 1-oxide, 2-chloro-3-(4-(3,4-dihydroxy-5-nitrophenyl)-1,2,3-thiadiazol-5-yl)-6-methylpyridine 1-oxide, 2-bromo-3-(4-(3,4-dihydroxy-5-nitrophenyl)-1,2,3-thiadiazol-5-yl)-6-methylpyridine 1-oxide, and 2-bromo-5-chloro-3-(4-(3,4-dihydroxy-5-nitrophenyl)-1,2,3-thiadiazol-5-yl)-4,6-dimethylpyridine 1-oxide.

Preferred compounds of the above general formula (I) having as central unit an thiazol-2,4-diyl moiety include 3-(4-(3,4-dihydroxy-5-nitrophenyl)thiazol-2-yl)-4-(trifluoromethyl)pyridine 1-oxide, 2-chloro-3-(4-(3,4-dihydroxy-5-nitrophenyl)thiazol-2-yl)-4,6-dimethylpyridine 1-oxide, 3-(4-(3,4-dihydroxy-5-nitrophenyl)thiazol-2-yl)-2-methyl-6-(trifluoromethyl)pyridine-1-oxide, 5-(4-(3,4-dihydroxy-5-nitrophenyl)thiazol-2-yl)-2-(trifluoromethyl)pyridine 1-oxide, 5-(4-(3,4-dihydroxy-5-nitrophenyl)thiazol-2-yl)-2-methyl-4-(trifluoromethyl)pyridine 1-oxide, 3-(4-(3,4-dihydroxy-5-nitrophenyl)thiazol-2-yl)-2,6-dimethyl-4-(trifluoromethyl)pyridine 1-oxide, 3,5-dichloro-4-(4-(3,4-dihydroxy-5-nitrophenyl)thiazol-2-yl)pyridine 1-oxide, 3-(4-(3,4-dihydroxy-5-nitrophenyl)thiazol-2-yl)-6-methyl-2-phenyl-4-(trifluoromethyl)pyridine 1-oxide, 2-bromo-3-(4-(3,4-dihydroxy-5-nitrophenyl)thiazol-2-yl)-4,5,6-trimethylpyridine 1-oxide, 2-chloro-3-(4-(3,4-dihydroxy-5-nitrophenyl)thiazol-2-yl)-4,5,6-trimethylpyridine 1-oxide, 3-(4-(3,4-dihydroxy-5-nitrophenyl)thiazol-2-yl)-2-(trifluoromethyl)pyridine 1-oxide, 2,5-dichloro-3-(4-(3,4-dihydroxy-5-nitrophenyl)thiazol-2-yl)-4,6-dimethylpyridine 1-oxide, 3-(4-(3,4-dihydroxy-5-nitrophenyl)thiazol-2-yl)-5-(trifluoromethyl)pyridine 1-oxide, 3-(4-(3,4-dihydroxy-5-nitrophenyl)thiazol-2-yl)-2-fluoropyridine 1-oxide, 4-(4-(3,4-dihydroxy-5-nitrophenyl)thiazol-2-yl)-2-fluoropyridine 1-oxide, 2-(4-(3,4-dihydroxy-5-nitrophenyl)thiazol-2-yl)-6-fluoropyridine 1-oxide, 2-chloro-3-(4-(3,4-dihydroxy-5-nitrophenyl)thiazol-2-yl)-6-methylpyridine 1-oxide, 2-bromo-3-(4-(3,4-dihydroxy-5-nitrophenyl)thiazol-2-yl)-6-methylpyridine 1-oxide, and 2-bromo-5-chloro-3-(4-(3,4-dihydroxy-5-nitrophenyl)thiazol-2-yl)-4,6-dimethylpyridine 1-oxide.

In one embodiment, compounds of the general formula I wherein the central unit consists of a 1,2,4-oxadiazo-3,5-diyl-moiety can be prepared by a process wherein a compound of the general formula IIA, IIB or IIC,

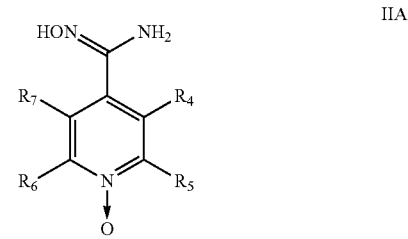

IIA

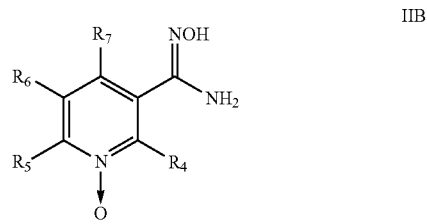

IIB

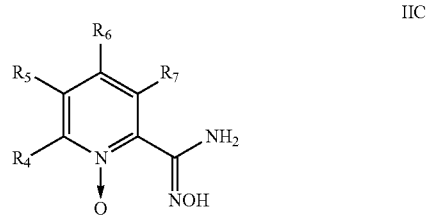

IIC wherein $R_4$, $R_5$, $R_6$ and $R_7$ are defined as in the general formula I, is subjected to a cyclisation reaction comprising condensation and dehydration with a compound of the general formula III,

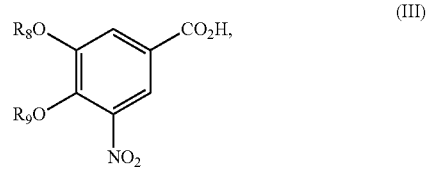

(III)

wherein $R_8$ and $R_9$ independently from each other represent hydrogen or suitable protective groups for aromatic hydroxyl groups, under conditions suitable to produce oxadiazole derivatives of formula IVA, IVB or IVC,

IVA

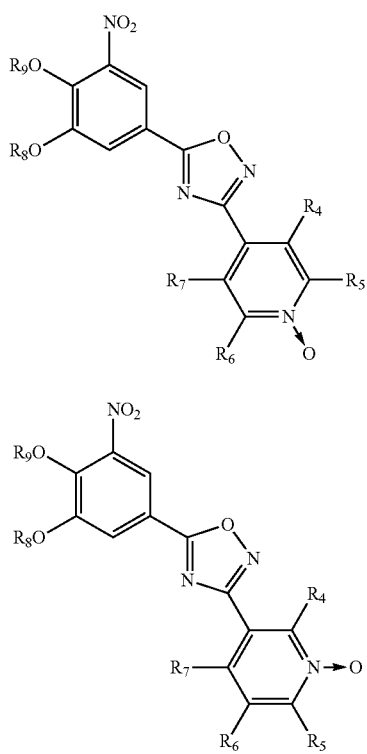

IVB

IVC

VA

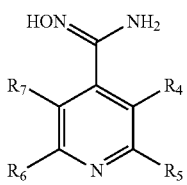

VB

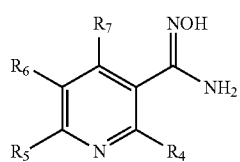

VC

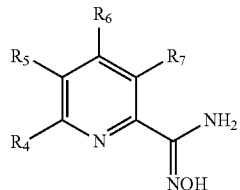

wherein $R_4$, $R_5$, $R_6$ and $R_7$ are defined as in the general formula I, is subjected to a cyclisation reaction comprising condensation and dehydration with a compound of the general formula III under conditions suitable to produce oxadiazole derivatives of formula VIA, VIB or VIC,

VIA

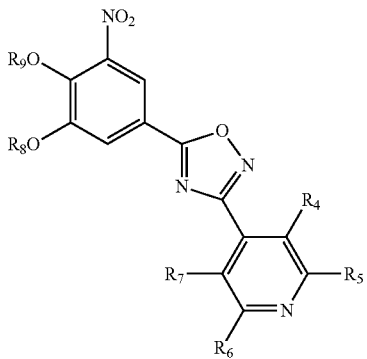

VIB

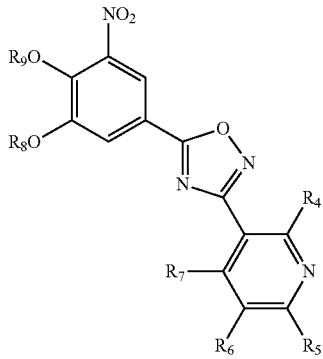

followed by removal of the hydroxyl protecting groups to provide the compounds of general formula I wherein the central unit consists of a 1,2,4-oxadiazo-3,5-diyl-moiety.

In another embodiment, the compounds of the general formula I wherein the central unit consists of a 1,2,4-oxadiazo-3,5-diyl-moiety can be prepared by a process wherein a compound of the general formula VA, VB or VC, -continued

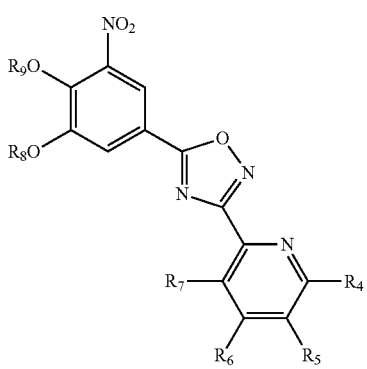

VIC followed by oxidation of the pyridyl nitrogen atom to give a compound according to formula IVA, IVB or IVC as shown above and finally, if necessary, the removal of the hydroxyl protecting groups to provide the compounds of general formula I wherein the central unit consists of a 1,2,4-oxadiazo-3,5-diyl-moiety.

Suitable protective groups for aromatic hydroxyl groups are well known in the art. Examples of suitable protective groups for aromatic hydroxyl groups include methyl, ethyl, isopropyl, benzyl, 4-methoxybenzyl, methoxymethyl, benzyloxymethyl, methoxyethoxymethyl, tetrahydropyranyl, phenacyl, allyl, trimethylsilyl, tert-butyldimethylsilyl, benzyloxycarbonyl, tert-butoxycarbonyl, ester, sulphonate, carbamate, phosphinate, acetal and ketal derivatives.

In a preferred embodiment, one of the groups $R_8$ and $R_9$ is hydrogen and the other is methyl. In a particularly preferred embodiment, $R_8$ represents methyl and $R_9$ represents hydrogen.

In an alternative preferred embodiment, the protective groups $R_8$ and $R_9$ are replaced with hydrogen or a group which is hydrolysable under physiological conditions. The protective groups $R_8$ and $R_9$ may be removed independently from each other in separate reaction steps or they may be removed in the same reaction step. Likewise, the insertion of a group which is hydrolysable under physiological conditions may take place either in the same or in a subsequent reaction step.

In the present invention, conditions suitable to produce oxadiazole derivatives comprise conditions which give the oxadiazole derivative in high yield and purity. Preferably, the yield of the desired oxadiazole derivative is at least 70%, more preferably 75 to 99%, even more preferably 80 to 97%, and most preferably 85 to 95%. Preferably, the purity of the desired oxadiazole derivative is at least 90%, more preferably at least 95%, even more preferably at least 99%, and most preferably at least 99.5%. Following the teaching of the present invention the skilled person can routinely determine the most suitable reaction conditions in order to optimize the yield and purity of the oxadiazole. Parameters to be taken into consideration by the skilled person include, but are not limited to, reagents effecting the condensation and dehydration agents, choice of protective groups $R_8$ and $R_9$, solvent system, reaction temperature and reaction time and solubility of reagents.

The compound of general formula III requires activation before condensation with a compound of formula IIA-IIC or VA-VC. Suitable reagents for activation of the compound of formula III include 1,1-carbonyldiimidazole, thionyl chloride, sulfonylchloride, N,N'-dicyclohexylcarbodiimide, 1-hydroxybenzotriazole and N-(3-dimethylaminopropyl)-N'-ethylcarbodiimide, phosgene, $PCl_3$, $POCl_3$, $PCl_5$, anhydrides, trichlorotriazine and chlorodimethoxytriazine and the like. Particularly preferable are 1,1-carbonyldiimidazole and thionyl chloride. In some cases, the same reagents can be employed to effect the cyclisation step, which consists of condensation and dehydration. Alternative reagents to effect condensation and/or dehydration include pyridine and tetrabutylammonium fluoride. Preferably the dehydration can be effected by thermal heating of the reaction mixture in conjunction with the aforementioned reagents.

The compound of general formula III can be activated with an excess of a reagent such as thionyl chloride in a suitable solvent or without the need for additional solvent. If preferred, the excess reagent can then be removed, e.g. by distillation, and replaced with a solvent and another reagent such as pyridine to effect the condensation and dehydration steps. Preferred solvent systems for activating the compound of general formula III, and cyclisation with compounds of general formulas IIA-IIC or VA-VC are dipolar aprotic solvents including dimethylformamide, dimethylsulfoxide, dimethylacetamide and N-methylpyrrolidinone. Particularly preferable are dimethylsulfoxide and dimethylacetamide.

Suitable reaction temperatures and reaction times depend on the reactivity of the utilized reagents for effecting condensation and dehydration. Preferably, the reaction temperature is in the range of 0° C. to the boiling point of the utilized solvent system, more preferably in the range of 20 to 150° C., and most preferably in the range of 25 to 120° C. Preferably, the reaction time is in the range of 30 minutes to 24 hours, more preferably in the range of 1 hour to 18 hours, and most preferably 2 to 6 hours.

In an alternative preferred embodiment, the condensation and dehydration reaction is carried out in the presence of an organic or inorganic base. Suitable preferred bases include triethylamine, tributylamine, 2,6-lutidine, N-methylmorpholine, pyridine, imidazole, N-methylimidazole and 4-dimethylaminopyridine. Particularly preferred bases include pyridine, N-methylimidazole and 4-dimethylaminopyridine.

In a preferred embodiment of the present invention, the condensation and dehydration are conducted in two separate reaction steps. In this particular embodiment, different condensation and dehydration agents and solvent systems may be utilized to optimize yield and purity of the obtained product.

In an alternative preferred embodiment of the present invention, the condensation and dehydration are conducted sequentially in the same vessel without isolation of the O-acylated intermediates. In this particular embodiment, the reagents effecting the condensation and dehydration can be the same or different but are preferably identical.

The amount of reagents effecting the condensation and dehydration are not critical. Typical amounts of reagents effecting the condensation and dehydration include at least an amount of 1 mol, preferably 2.1 mol to 5 mol, more preferably 2.2 to 4 mol, and most preferably 2.3 mol to 3 mol, per mol pyridine derivative. In cases in which the reagents effecting the condensation and dehydration also serves as solvent or co-solvent, the excess amount may be much higher.

As mentioned above, in preferred embodiments the invention includes a step in which the nitrogen atom of the pyridyl moiety VIA, VIB or VIC is oxidized under suitable conditions to the corresponding pyridyl-N-oxide derivative IVA, IVB or IVC after the cyclisation reaction.

In the present invention, suitable oxidative conditions to produce the pyridyl-N-oxide comprise conditions which give the pyridyl-N-oxide derivative in high yield and purity.

Preferably, the yield of the desired pyridyl-N-oxide derivative is at least 90%, more preferably 92 to 99%, even more preferably 94 to 98%, and most preferably 95 to 97%. Preferably, the purity of the desired pyridyl-N-oxide derivative is at least 90%, more preferably at least 95%, even more preferably at least 99%, and most preferably at least 99.5%. Following the teaching of the present invention the skilled person can routinely determine the most suitable reaction conditions in order to optimize the yield and purity of the pyridyl-N-oxide. Parameters to be taken into consideration by the skilled person include, but are not limited to, oxidizing agent, amount of oxidizing agent, choice of protective groups, solvent system, reaction temperature and reaction time and solubility of reagents.

Preferred oxidizing agents include hydrogen peroxide, $MnO_2$, peracetic acid, trifluoroperacetic acid, t-butylhydroperoxide, m-chloroperoxybenzoic acid, persulfuric acids, Oxone®, urea hydrogen peroxide complex and trifluoroacetic anhydride, pyridinium chlorochromate and permanganate ions. Particularly preferred is urea hydrogen peroxide complex and trifluoroacetic anhydride.

The preferred amount of oxidizing agent is in the range of equimolar amounts to a 20-fold excess to the pyridine derivative. Preferably, amount of oxidizing agent is in the range of a 1.2-fold to 10-fold excess, more preferably 1.5-fold to 8-fold excess and most preferably 2-fold to 5-fold excess.

Preferred solvent systems for conducting the oxidation are solvents which are inert to the oxidizing agent. Particularly preferred are halogenated solvents, such as dichloromethane, chloroform, chlorobenzene and carbon tetrachloride, aromatic solvents such as benzene and toluene, alkanes such as cyclohexane and hexane, and ethers such as THF, 1,4-dioxane and tert-butylmethylether.

Suitable reaction temperatures and reaction times depend on the reactivity of the utilized oxidizing agent. Preferably, the reaction temperature is in the range of 0° C. to the boiling point of the utilized solvent system, more preferably in the range of 20 to 100° C., and most preferably in the range of 40 to 80° C. Preferably, the reaction time is in the range of 30 minutes to 24 hours, more preferably in the range of 1 hour to 18 hours, and most preferably 2 to 6 hours.

The oxidation of the pyridyl nitrogen atom can be carried out at any stage of the process of preparation of compounds according to the general formula I. Preferably, the oxidation is conducted before formation of the compounds of formulae IIA-IIC, or alternatively after formation of the oxadiazole ring as in compounds of formulae VIA-VIC.

In another aspect of the invention, compounds of formula IIA, IIB or IIC are prepared by reacting compounds of the general formula VIIA, VIIB or VIIC,

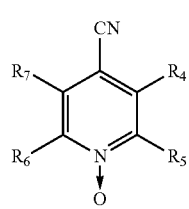

VIIA

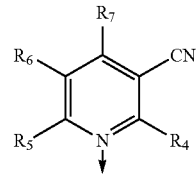

VIIB

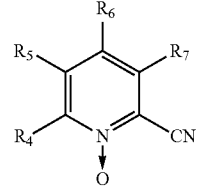

VIIC with hydroxylamine in the presence of a chelating agent under suitable reaction conditions.

In another aspect of the invention, compounds of formula VA, VB or VC are prepared by reacting compounds of the general formula VIIIA, VIIIB or VIIIC,

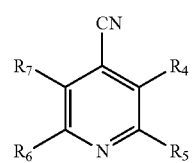

VIIIA

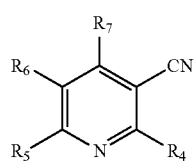

VIIIB

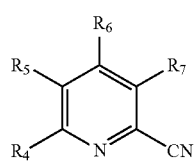

VIIIC with hydroxylamine in the presence of a chelating agent under suitable reaction conditions.

In the present invention, suitable reaction conditions of the above reactions comprise conditions which give the amidoxime derivative in high yield and purity. Preferably, the yield of the desired amidoxime derivative is at least 70%, more preferably 72 to 95%, even more preferably 75 to 90%, and most preferably 78 to 85%. Preferably, the purity of the desired amidoxime derivative is at least 90%, more preferably at least 95%, even more preferably at least 96%, and most preferably at least 97%. Following the teaching of the present invention the skilled person can routinely determine the most suitable reaction conditions in order to optimize the yield and purity of the amidoxime. Parameters to be taken into consideration by the skilled person include, but are not limited to, amount of hydroxylamine, choice of catalyst, nature of substituents $R_4$ to $R_7$, solvent system, reaction temperature and reaction time and solubility of reagents.

The preferred amount of hydroxylamine is in the range of equimolar amounts to a 50-fold excess to the pyridine derivative. Preferably, the amount of hydroxylamine is in the range of a 1.2-fold to 20-fold excess, more preferably 1.5-fold to 10-fold excess and most preferably 3-fold to 5-fold excess.

Preferred chelating agents include 8-hydroxyquinoline, ortho-phenanthroline and hydrates and derivatives thereof. The preferred amount of chelating agent is in the range 0.1-10 mol %, more preferably 0.5-5 mol %, more preferably 0.75-3 mol % and most preferably 1-1.5 mol %.

The solvent system is not particularly limited and includes water, alcohols such as methanol, ethanol or isopropanol, ethers such as THF or 1,4-dioxane, and dipolar aprotic solvents, such as dimethylsulfoxide and the like or mixtures of these solvents.

Preferably, the reaction temperature is in the range of 0° C. to the boiling point of the utilized solvent system, more preferably in the range of 20 to 100° C., and most preferably in the range of 40 to 80° C. Preferably, the reaction time is in the range of 30 minutes to 24 hours, more preferably in the range of 1 hour to 18 hours, and most preferably 2 to 8 hours.

For the preparation of pharmaceutical compositions of general formula (I), inert pharmaceutically acceptable carriers are admixed with the active compounds. The pharmaceutically acceptable carriers may be either solid or liquid. Solid form preparations include powders, tablets, dispersible granules and capsules. A solid carrier can be one or more substances which may also act as diluents, flavouring agents, solubilizers, lubricants, suspending agents, binders or tablet disintegrating agents; it may also be an encapsulating material.

Preferably, the pharmaceutical preparation is in unit dosage form, e.g. packaged preparation, the package containing discrete quantities of preparation such as packeted tablets, capsules and powders in vials or ampoules.

The dosages may be varied depending on the requirement of the patient, the severity of the disease and the particular compound being employed. For convenience, the total daily dosage may be divided and administered in portions throughout the day. Determination of the proper dosage for a particular situation is within the skill of those in the medical art.

Materials and Methods
Assay of Mouse COMT Activity

Liver samples from 60 days old NMRI mice weighing 20-30 g (Harlan-Interfauna Ibérica, Barcelona, Spain) kept ten per cage under controlled environmental conditions (12 h light/dark cycle and room temperature 24° C.), were used in all experiments. Saline perfused tissues, obtained from pentobarbitone (60 mg/kg) anaesthetised mice, were used in the experiments. Tissues were immediately removed and homogenised in 5 mM phosphate buffer, pH 7.8 and stored at −80° C.

COMT activity was evaluated by the ability to methylate adrenaline to metanephrine, as previously described (Vieira-Coelho, M. A., Soares-da-Silva, P., Brain Res, 1999, 821, 69-78). Aliquots of 0.5 ml of liver homogenates were preincubated for 20 min with 0.4 ml of phosphate buffer (5 mM); thereafter, the reaction mixture was incubated for 10 min with adrenaline (500 mM; 0.1 ml) in the presence of a saturating concentration of S-adenosyl-L-methionine, the methyl donor (250 µM). The incubation medium also contained pargyline (100 µM), $MgCl_2$ (100 µM) and EGTA (1 mM). The preincubation and incubation were carried out at 37° C. under conditions of light protection with continuous shaking and without oxygenation. At the end of the incubation period the tubes were transferred to ice and the reaction was stopped by the addition of 200 µl of 2 M perchloric acid. The samples were then centrifuged (200×g, 4 min, 4° C.), and 500 µl aliquots of the supernatant, filtered on 0.22 µm pore size Spin-X filter tubes (Costar) were used for the assay of metanephrine by high pressure liquid chromatography with electrochemical detection.

In experiments designed to evaluate the effects of test compounds upon liver COMT, test compounds (in 5% carboxymethylcellulose) were given by gastric tube to overnight fasted mice. Thereafter, at defined intervals, livers were removed and used to determine COMT activity as described above.

Assay of Rat COMT Activity

Livers from 60 day old male Wistar rats weighing 240-260 g (Harlan-Interfauna Ibérica, Barcelona, Spain), kept two per cage under controlled environmental conditions (12 h light/dark cycle and room temperature 24° C.) were used in all experiments. After decapitation, the organs were immediately removed and homogenised in 5 mM phosphate buffer of pH 7.8. COMT activity was evaluated by the ability to methylate adrenaline to metanephrine. Aliquots of 0.5 ml of liver homogenates were preincubated for 20 min with 0.4 ml of phosphate buffer (5 mM); thereafter, the reaction mixture was incubated for 5 min with epinephrine (1000 µM; 0.1 ml) in the presence of a saturating concentration of S-adenosyl-L-methionine (500 µM), the methyl donor; the incubation medium contained also pargyline (100 µM), $MgCl_2$ (100 µM) and EGTA (1 mM). The preincubation and incubation were carried out at 37° C. under conditions of light protection with continuous shaking and without oxygenation.

In experiments designed to evaluate the oral bioavailability of test substances, compounds were given by gastric tube to overnight fasted rats. Thereafter, at defined intervals, animals were killed by decapitation and livers removed and used to determine COMT activity as described above. At the end of the incubation period (5 min) the tubes were transferred to ice and the reaction was stopped by the addition of 200 µl of 2 M perchloric acid. The samples were then centrifuged (200×g, 4 min, 4° C.), and 500 µl aliquots of the supernatant, filtered on 0.22 µm pore size Spin-X filter tubes (Costar) were used for the assay of metanephrine. The assay of metanephrine was carried out by means of high pressure liquid chromatography with electrochemical detection. The lower limits for detection of metanephrine ranged from 350 to 500 fmol (0.5 to 1.0 pmol/mg protein/h).

Levels of L-DOPA and 3-O-Methyl-L-DOPA in Plasma

Rats fasted overnight were administered orally with tolcapone, entacapone and compounds of general formula I (all at 3 mg/kg) or vehicle (0.5% carboxymethylcellulose, 4 ml/kg). One, 6 or 23 h later, rats were administered orally with L-DOPA (12 mg/kg) plus benserazide (3 mg/kg) or with vehicle (0.5% carboxymethylcellulose, 4 ml/kg). One hour later rats were anaesthetised with sodium pentobarbitone (60 mg/kg, i.p.), blood was collected through the vena cava and the whole brain was quickly removed. Blood samples were centrifuged for 15 min at 3,000 g (4° C.) and the plasma samples were stored at −80° C. till the assay of L-DOPA and 3-O-methyl-L-DOPA. All animals interventions were performed in accordance with the European Directive number 86/609, and the rules of the "Guide for the Care and Use of Laboratory Animals", 7th edition, 1996, Institute for Laboratory Animal Research (ILAR), Washington, D.C.

Assay of L-DOPA and Catechol Derivatives

L-DOPA and 3-O-methyl-L-DOPA in blood samples were assayed by HPLC with electrochemical detection, as previously described (Soares-da-Silva et al., Brain Res. 2000; 863:293-297). In brief, aliquots of 20 μl were injected into the chromatograph. The chromatographic system consisted of a pump (Gilson 307) and a stainless steel 5 μm ODS2 column (Biophase; Bioanalytical Systems, West Lafayette, Ind.) of 25 cm length and 4.6 mm diameter; samples were injected by means of an automatic sample injector (Gilson 231) connected to a Gilson dilutor (Gilson 401). The mobile phase was a degassed solution of citric acid 0.1 mM; sodium octylsulphate 0.5 mM; sodium acetate 0.1 M; $Na_2EDTA$ 0.17 mM; dibutylamine 1 mM and methanol (10% v/v), adjusted to pH 3.5 with PCA 2 M and pumped at a rate of 1.0 ml $min^{-1}$. The detection was carried out electrochemically with a glassy carbon electrode, an Ag/AgCl reference electrode and an amperometric detector (Gilson 142); the detector cell was operated at 0.75 V. The current produced was monitored using the Gilson Unipoint HPLC software.

Cell Toxicity

The method, which detects cell toxicity of a test substance, follows that described by Pedrosa and Soares-da-Silva (Br. J. Pharmacol., 137, 1 1305-1313, 2002). Briefly, Neuro 2A mouse neuroblastoma cells were seeded in 96-well plates in 200 μL per well of culture medium for cell attachment (CMA), under a $CO_2$/air (5%/95%) humidified atmosphere at 37° C. Controls of the test system prior to incubations consisted in a morphological control (light microscopy) of the cultured cells: attachment, spreading and density. Five days after seeding (24 h after cells become confluent), the test compounds were incubated for 24 h with cultured cells. Cultures with no test article or ethanol were run in parallel as negative and positive controls. All incubations contained the same percentage of solvent needed for the test compound.

Cell viability was measured using calcein-AM (Molecular Probes, Eugene, Oreg., USA). The membrane permeant calcein-AM, a nonfluorescent dye, is taken up and converted by intracellular esterases to membrane impermeant calcein, which emits green fluorescence. After treatment with test article or vehicle for 24 h, cells are washed twice with Hanks' medium (medium composition, in mM: NaCl, 137; KCl, 5; $MgSO_4$, 0.8; $Na_2HPO_4$, 0.33; $KH_2PO_4$, 0.44; $CaCl_2$, 0.25; $MgCl_2$, 1.0; Tris HCl, 0.15 and sodium butyrate, 1.0, pH=7.4) and loaded with 2 μM calcein-AM in Hanks' medium, at room temperature for 30 min. Fluorescence is measured at 485 nm excitation and 530 nm emission wavelengths in a multiplate reader. To determine minimum staining for calcein-AM (calceinmin), eight wells were treated with ethanol 30 min before calcein-AM addition. The percent viability is then calculated as [($calcein_{sample}$−$calcein_{min}$)/($calcein_{control}$−$calcein_{min}$)]×100.

Results

Table 1 shows the effects of standard COMT inhibitors, tolcapone and entacapone, and compounds of general formula I upon mouse liver COMT activity 3 h after their oral administration (3 mg/kg). Also shown in table 1 is the cell viability after 24 h exposure to tolcapone, entacapone and compounds of general formula I (all at 30 μM) in Neuro 2A cells.

TABLE 1

Mouse Liver COMT activity (% control) after 3 mg/kg (oral) administration of compounds listed and Neuro 2A cell viability (% of viable cells)

| No. | (X)n, (Y)n | R3 | COMT activity (% of control) | % of viable cells |
| --- | --- | --- | --- | --- |
| Tolcapone |  |  | 13.9 | 27.2 |
| Entacapone |  |  | 79.8 | 81.4 |
| 1 | n = m = 0 | —$CH_3$ | 59.9 | 55.1 |
| 2 | n = m = 0 | —$CH_3$ | 78.8 | 92.5 |
| 3 | n = m = 0 | —$CH_3$ | 63.6 | 100.5 |
| 4 | n = m = 0 | 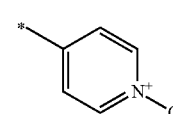 | 42.1 | 98.3 |
| 5 | n = m = 0 | 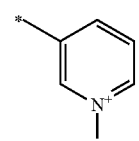 | 58.4 | 93.8 |
| 6 | n = m = 0 | 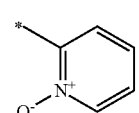 | 101.0 | 107.1 |
| 7 | n = m = 0 | 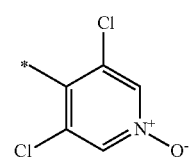 | 14.2 | 56.9 |

TABLE 1-continued

Mouse Liver COMT activity (% control) after 3 mg/kg (oral) administration of compounds listed and Neuro 2A cell viability (% of viable cells)

| No. | (X)n, (Y)n | R3 | COMT activity (% of control) | % of viable cells |
|---|---|---|---|---|
| 8 | n = m = 0 | 2-Cl-pyridine N-oxide | 55.4 | 106.7 |
| 9 | n = m = 0 | 2-Ph-pyridine N-oxide | 80.6 | 79.7 |
| 10 | n = m = 0 | 2-(3-furyl)-pyridine N-oxide | 95.2 | 69.3 |
| 11 | n = m = 0 | 2-morpholino-pyridine N-oxide | 63.9 | 105.7 |
| 12 | n = m = 0 | 2-thiomorpholino-pyridine N-oxide | 92.9 | 91.7 |
| 13 | n = m = 0 | 2-SPh-pyridine N-oxide | 102.3 | |
| 14 | n = m = 0 | 2-OPh-pyridine N-oxide | 76.8 | 83.5 |
| 15 | n = m = 0 | 2,6-dimethyl-pyridine N-oxide | 79.2 | 97.1 |
| 16 | n = m = 0 | 2-SO$_2$CH$_3$-pyridine N-oxide | 85.9 | 64.6 |
| 17 | n = m = 0 | 2-SCH$_3$-pyridine N-oxide | 89.9 | 96.0 |

TABLE 1-continued
Mouse Liver COMT activity (% control) after 3 mg/kg (oral) administration of compounds listed and Neuro 2A cell viability (% of viable cells)
| No. | (X)n, (Y)n | R3 | COMT activity (% of control) | % of viable cells |
|---|---|---|---|---|
| 18 | n = m = 0 | 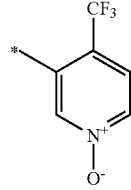 | 21.2 | 93.4 |
| 19 | n = m = 0 | 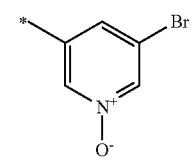 | 45.2 | 100.1 |
| 20 | n = m = 0 | 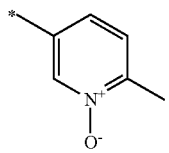 | 56.6 | |
| 21 | n = m = 0 | 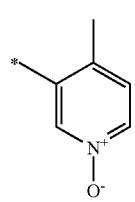 | 95.6 | |
| 22 | n = m = 0 | 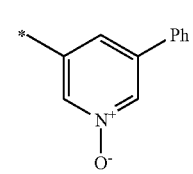 | 111.6 | |
| 23 | n = m = 0 | 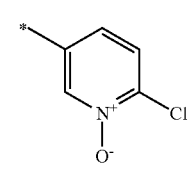 | 43 | 41.1 |
| 24 | n = m = 0 | 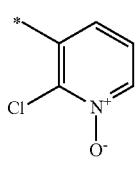 | 71.8 | 93.7 |
| 25 | n = m = 0 | 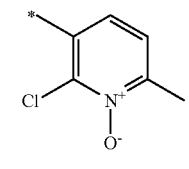 | 23.1 | 100.2 |

TABLE 1-continued
Mouse Liver COMT activity (% control) after 3 mg/kg (oral) administration of compounds listed and Neuro 2A cell viability (% of viable cells)
| No. | (X)n, (Y)n | R3 | COMT activity (% of control) | % of viable cells |
|---|---|---|---|---|
| 26 | n = m = 0 | 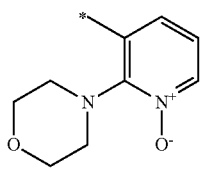 | 35.5 | 110.9 |
| 27 | n = m = 0 | 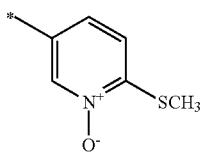 | 47.5 | 95.7 |
| 28 | n = m = 0 | 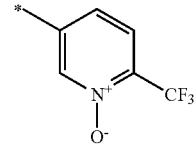 | 11.3 | 87.0 |
| 29 | n = m = 0 | 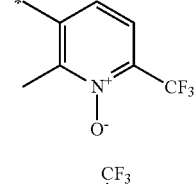 | 10.9 | 62.2 |
| 30 | n = m = 0 | 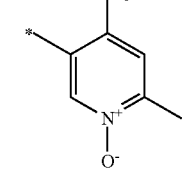 | 8.8 | 81.8 |
| 31 | n = m = 0 | 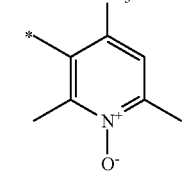 | 0.8 | 37.2 |
| 32 | n = m = 0 | 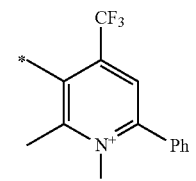 | 9.7 | 26.6 |
| 33 | n = m = 0 | 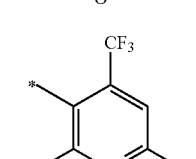 | 39.8 | 45.0 |

TABLE 1-continued

Mouse Liver COMT activity (% control) after 3 mg/kg (oral) administration of compounds listed and Neuro 2A cell viability (% of viable cells)

| No. | (X)n, (Y)n | R3 | COMT activity (% of control) | % of viable cells |
|---|---|---|---|---|
| 34 | n = m = 0 | 4-quinoline N-oxide | 88.6 | 89.0 |
| 35 | n = m = 0 | 3-quinoline N-oxide | 81.2 | 88.0 |
| 36 | n = m = 0 | 2-Br-6-methylpyridine N-oxide (3-yl) | 22.9 | 76.3 |
| 37 | n = m = 0 | 2-Cl-4,6-dimethylpyridine N-oxide (3-yl) | 42.5 | 92.3 |
| 38 | n = m = 0 | 2-Br-4,6-dimethylpyridine N-oxide (3-yl) | 16.3 | 86.0 |
| 39 | X = CH2, n = 1, m = 0 | pyridine N-oxide (3-yl) | 53.8 | 94.9 |
| 40 | n = m = 0 | 2-Br-4,5,6-trimethylpyridine N-oxide (3-yl) | 55.2 | 69.1 |
| 41 | n = m = 0 | 2-Cl-4,5,6-trimethylpyridine N-oxide (3-yl) | 14 | 95.1 |

TABLE 1-continued

Mouse Liver COMT activity (% control) after 3 mg/kg (oral) administration of compounds listed and Neuro 2A cell viability (% of viable cells)

| No. | (X)n, (Y)n | R3 | COMT activity (% of control) | % of viable cells |
|---|---|---|---|---|
| 42 | n = m = 0 |  | 9.4 | 96.4 |
| 43 | X = CH2, n = 1, m = 0 | 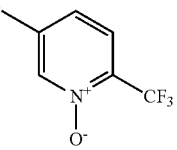 | 27.2 | 101.5 |
| 44 | X = CH2, n = 1, Y = O, m = 1 | 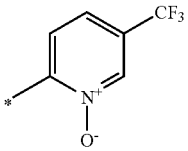 | 24.5 | |
| 45 | n = m = 0 | 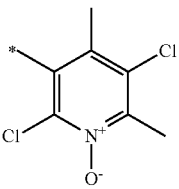 | 30.4 | 86.6 |
| 46 | n = m = 0 | 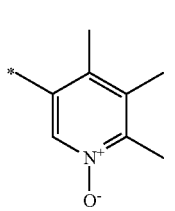 | 43.1 | 53.0 |
| 47 | n = m = 0 | 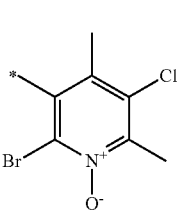 | 25.2 | 81.2 |

Note:
\* represents the point of attachment of the pyridine N-oxide substituent to the molecule Compounds of general formula I were also found to be potent inhibitors of rat liver COMT, the maximal inhibitory effect being achieved within 1 h to 3 h after their oral administration (Table 2). The maximal inhibitory effect of entacapone (Ent) and tolcapone (Tolc) were observed within 1 h after administration (Table 2). Nine hours after administration, entacapone is devoid of COMT inhibitory effects and tolcapone produces minimal inhibitory effects (~16% inhibition), whereas compounds of general formula I continue to inhibit COMT activity by 22% to 90% of control levels (Table 2).

TABLE 2

Rat Liver COMT activity (% control) after 3 mg/kg (oral) administration of compounds listed.

| Compound | Time (h) | | | |
|---|---|---|---|---|
| | 1 | 3 | 6 | 9 |
| Entacapone | 32.0 | 74.5 | 95.2 | 100.0 |
| Tolcapone | 18.3 | 28.6 | 56.8 | 83.9 |
| 18 | 5.2 | 19.9 | 43.0 | 57.4 |
| 29 | 1.2 | 18.5 | 39.7 | 56.4 |

TABLE 2-continued

Rat Liver COMT activity (% control) after 3 mg/kg (oral) administration of compounds listed.

| Compound | Time (h) | | | |
|---|---|---|---|---|
| | 1 | 3 | 6 | 9 |
| 30 | 6.3 | 34.8 | 41.2 | 54.5 |
| 41 | 21.2 | 9.3 | 18.8 | 39.7 |
| 42 | 3.6 | 6.1 | 12.3 | 30.9 |
| 43 | 16.1 | 30.6 | 64.3 | 77.9 |
| 45 | 1.1 | 1.2 | 3.8 | 8.9 |
| 47 | 10.6 | 4.0 | 3.8 | 8.2 |

Table 3 shows percentage changes in plasma levels of L-DOPA and 3-O-methyl-L-DOPA (3-OMD) of rats treated with L-DOPA plus benserazide at 2 h after the administration of entacapone, tolcapone and compounds of general formula I (3 mg/kg). L-DOPA plus benserazide were administered 1 h before collection of plasma samples. This time-point was chosen because it represented the $t_{max}$ for L-DOPA. As can be observed, compounds of general formula I produced significant increases in plasma L-DOPA accompanied by marked decrease in plasma 3-O-methyl-L-DOPA.

TABLE 3

Effect of of compounds listed (3 mg/kg; oral administration) upon changes (% control) in plasma levels of L-DOPA and 3-O-methyl-L-DOPA (3-OMD) of rats treated with L-DOPA plus benserazide.

| Compound | L-DOPA % increase | 3-OMD % reduction | L-Dopa/ 3-OMD |
|---|---|---|---|
| Entacapone | 68.5 | −55.6 | 3.8 |
| Tolcapone | 202.4 | −89.0 | 27.6 |
| 18 | 61.4 | −63.9 | 4.5 |
| 29 | 105.1 | −80.7 | 10.6 |
| 30 | 103.5 | −75.0 | 8.1 |
| 41 | 95.2 | −72.3 | 7.1 |
| 42 | 30.7 | −43.4 | 2.3 |
| 43 | 74.9 | −48.3 | 3.4 |
| 45 | 100.8 | −54.3 | 4.4 |
| 47 | 102.9 | −58.5 | 4.9 |

Conclusion

Compounds of general formula I are very potent catechol-O-methyltransferase (COMT) inhibitors with significantly reduced toxicity. Compounds of general formula I have potentially valuable pharmaceutical properties in the treatment of some central and peripheral nervous system disorders where inhibition of O-methylation of catecholamines may be of therapeutical benefit, such as mood disorders, Parkinson's disease and parkinsonian disorders, restless legs syndrome, gastrointestinal disturbances, edema formation states and hypertension. The possibility to use a potent, long-acting inhibitor with improved safety profile opens new perspectives in the treatment of Parkinson's disease and parkinsonian disorders, gastrointestinal disturbances, edema formation states, and hypertension by improving the safety of nitrocatecholic COMT inhibitors whilst improving or maintaining duration and selectivity of COMT inhibition. This is particularly important when thinking of treating patients afflicted by Parkinson's disease who are taking L-DOPA plus a peripheral AADC inhibitor due to the fact that this is long-term treatment.

The invention disclosed herein is exemplified by the following examples of preparation, which should not be construed to limit the scope of the disclosure. Alternative pathways and analogous structures may be apparent to those skilled in the art.

EXAMPLE 1

3-Nitro-5-[3-(1-oxy-pyridin-4-yl)-[1,2,4]oxadiazol-5-yl]-benzene-1,2-diol (Compound 4, Table 1)

a) To a stirred solution of 3,4-dibenzyloxy-5-nitrobenzoic acid (0.5 g, 1.32 mmol) in dimethylformamide (5 mL) at room temperature was added 1,1-carbonyldiimidazole (0.246 g, 1.52 mmol) in one portion. After stirring for one hour, N'-hydroxypyridine-4-carboximidamide (0.208 g, 1.52 mmol) was added in one portion and the resulting mixture was stirred at room temperature overnight. The mixture was then stirred at 110° C. for three hours and then allowed to cool to room temperature. The mixture was poured onto ice-water (100 mL) and extracted with 20% isopropanol/dichloromethane. The organic extracts were washed with water and brine, then dried (Na$_2$SO$_4$), filtered and evaporated to leave a solid residue that was recrystallised from ethanol. 4-[5-(3,4-Bis-benzyloxy-5-nitro-phenyl)-[1,2,4]oxadiazol-3-yl]-pyridine was obtained as a beige solid (0.395 g, 62%).

b) A stirred solution of the above pyridine compound (0.331 g, 0.689 mmol) in dichloromethane (15 mL) was cooled in an ice-water bath and m-chloroperoxybenzoic acid (0.179 g, 1.03 mmol) was added in portions. The resulting mixture was stirred in the cold for thirty minutes and then at room temperature for thirty minutes whereupon it was cooled again in an ice-water bath. Further m-chloroperoxybenzoic acid (0.17 g, 1.03 mmol) was added and the mixture was then allowed to stir at room temperature for one and a half hours. Water (20 mL) was added and the organic phase was separated and washed with saturated aqueous sodium bicarbonate solution, water and brine, then dried (Na$_2$SO$_4$), filtered and evaporated to leave a yellow oil. Addition of diethyl ether caused formation of a precipitate that was filtered off and recrystallised from a dichloromethane/isopropanol mixture. 4-[5-(3,4-Bis-benzyloxy-5-nitro-phenyl)-[1,2,4]oxadiazol-3-yl]-pyridine 1-oxide was obtained as white crystals (0.239 g, 70%).

c) A solution of the above dibenzyl ether (0.232 g, 0.468 mmol) in dichloromethane (5 mL) was cooled to −78° C. with stirring under argon and treated with boron tribromide (0.586 g, 2.34 mmol) dropwise. The resulting deep purple suspension was then allowed to stir at room temperature for one hour before cooling again to −78° C. The mixture was quenched by the careful addition of methanol. After stirring at room temperature for one hour, the volatiles were evaporated and the residue treated with ethanol/toluene and re-evaporated. The yellow residue was triturated with boiling ethanol and filtered whilst still warm to give the title product as a yellow solid (0.102 g, 69%) of m.p. 280-282° C.

EXAMPLE 2

3-Nitro-5-[3-(1-oxy-pyridin-3-yl)-[1,2,4]oxadiazol-5-yl]-benzene-1,2-diol (Compound 5, Table 1)

a) To a stirred solution of 3,4-dimethoxy-5-nitrobenzoic acid (0.232 g, 1.022 mmol) in dimethylformamide (5 ml) at room temperature was added 1,1-carbonyldiimidazole (0.174 g, 1.073 mmol) in one portion. The resulting mixture was stirred for ninety minutes whereupon N'-hydroxypyridine-3-carboximidamide 1-oxide (0.156 g, 1.022 mmol) was added in one portion. The resulting mixture was stirred at room temperature for two hours, then at 75° C. overnight. After cooling to room temperature, the mixture was poured onto water (100 mL) and the precipitate was filtered off, washed with water, then dried in air and recrystallised from diethyl ether. 3-[5-(3,4-dimethoxy-5-nitro-phenyl-[1,2,4]oxadiazol-3-yl]-pyridine 1-oxide was obtained as a white solid (0.162 g, 46%).

b) To a stirred solution of the dimethyl ether from above (0.153 g, 0.445 mmol) in dichloromethane (10 mL) at −78° C. under argon was added boron tribromide dropwise (0.445 g, 1.779 mmol). The reaction mixture was allowed to warm to room temperature and stirred for ninety minutes before pouring carefully onto water (100 mL). After stirring for twenty minutes, the mixture was extracted with ethyl acetate. The organic extracts were washed with water and brine, dried ($Na_2SO_4$), filtered and evaporated. 2-methoxy-3-nitro-5-[3-(1-oxy-pyridin-3-yl)-[1,2,4]oxadiazol-5-yl]-phenol was obtained as a yellow solid (0.12 g, 82%).

c) A stirred suspension of the above methyl ether (0.108 g, 0.327 mmol) in 1,2-dichloroethane (10 mL) at room temperature under argon was treated with aluminium chloride (0.087 g, 0.654 mmol) followed by pyridine (0.207 g, 2.62 mmol) dropwise. The mixture was then heated at reflux for seven hours whereupon further aluminium chloride (0.087 g, 0.654 mmol) and pyridine (0.207 g, 2.62 mmol) were added and the mixture stirred at reflux for a further seven hours. The mixture was then allowed to cool to room temperature, and poured onto cold 1 N hydrochloric acid (30 mL). The resulting precipitate was filtered off, washed with water and dried at 50° C. under vacuum. The desired product was obtained as an orange solid, (0.075 g, 72%) of m.p. 278-280° C.

EXAMPLE 3

3-Nitro-5-[3-(1-oxy-pyridin-2-yl)-[1,2,4]oxadiazol-5-yl]-benzene-1,2-diol (Compound 6, Table 1)

a) To a stirred solution of 3,4-dimethoxy-5-nitrobenzoic acid (1.0 g, 4.40 mmol) in dimethylformamide (10 mL) at room temperature was added 1,1-carbonyldiimidazole (0.821 g, 5.06 mmol) in one portion. The resulting yellow mixture was allowed to stir for ninety minutes whereupon N'-hydroxypyridine-2-carboximidamide 1-oxide (0.775 g, 5.06 mmol) was added in one portion. The resulting mixture was stirred at room temperature overnight and then poured onto water (100 mL). The resulting precipitate was filtered off, washed with water and then taken up in dichloromethane (30 mL). The organic layer was washed with water and brine, dried ($Na_2SO_4$), filtered and evaporated to leave a white solid (1.37 g, 86%).

b) To a stirred suspension of the solid obtained above (1.365 g, 3.77 mmol) in tetrahydrofuran (14 mL) at room temperature under argon was added a 1 N solution of tetrabutylammonium fluoride in tetrahydrofuran (3.8 mL, 3.8 mmol). The resulting clear yellow solution was allowed to stir at room temperature for seven hours during which time a new precipitate had formed. The mixture was filtered and the solid was washed with several portions of cold tetrahydrofuran. 2-[5-(3,4-Dimethoxy-5-nitro-phenyl)-[1,2,4]oxadiazol-3-yl]-pyridine 1-oxide was obtained as a white solid (0.97 g, 75%).

c) To a stirred suspension of the dimethyl ether obtained from above (0.961 g, 2.79 mmol) in dichloromethane (15 mL) at −78° C. under argon was added boron tribromide (3.5 g, 13.97 mmol) dropwise. The resulting purple suspension was then allowed to stir at room temperature for seven hours before being cooled in an ice/water bath. The mixture was carefully quenched by the addition of methanol. The resulting yellow mixture was allowed to stir at room temperature for one hour before the precipitate was filtered off and washed with methanol. The solid was triturated with boiling ethanol and filtered whilst warm. After drying, the desired compound was obtained as an orange solid (0.712 g, 81%) of m.p. 168° C.

EXAMPLE 4

5-(5-Methyl-[1,2,4]oxadiazol-3-yl)-3-nitro-benzene-1,2-diol (Compound 2, Table 1)

a) To a stirred solution of 3,4-bis-benzyloxy-N'-hydroxy-5-nitro-benzamidine (1.0 g, 2.54 mmol) in dimethylformamide (5 mL) at room temperature was added 1,1-carbonyldiimidazole (0.494 g, 3.048 mmol) in one portion and the mixture was stirred at room temperature for ninety minutes. Thereupon, acetic acid (0.184 g, 3.067 mmol) was added dropwise and the mixture was allowed to stir for two hours at room temperature, then at 155° C. for three hours. The mixture was allowed to cool to room temperature, and poured onto ice-water (100 mL). Brine (10 mL) was added and the resulting precipitate was removed by filtration, washed with water and dried in air. The solid was then dissolved in dichloromethane (20 mL) and a spatula tip of activated charcoal was added. After stirring for twenty minutes, the suspension was filtered through celite and the filtrate was evaporated to leave a yellow oil that solidified on standing. After recrystallisation from dichloromethane/petroleum ether, 3-(3,4-bis-benzyloxy-5-nitrophenyl)-5-methyl-[1,2,4]oxadiazole was obtained as a pale yellow solid (0.537 g, 51%).

b) To a stirred solution of the solid obtained from above (0.128 g, 0.307 mmol) in dichloromethane (15 mL) at −78° C. under argon was added boron tribromide (0.318 g, 1.269 mmol) dropwise. The resulting purple suspension was allowed to stir at room temperature for one hour, then cooled again to −78° C. The mixture was quenched by the careful addition of methanol, and after stirring at room temperature for one hour, the solvents were evaporated. The yellow residue was triturated with diethyl ether, filtered and dried. The desired compound was obtained as a yellow solid (0.070 g, 96%) of m.p. 169.8-172° C.

EXAMPLE 5

5-(5-Methyl-[1,3,4]oxadiazol-2-yl)-3-nitro-benzene-1,2-diol (Compound 3, Table 1)

a) To a stirred solution of 3,4-dimethoxy-5-nitrobenzoic acid (0.438 g, 1.93 mmol) in tetrahydrofuran (10 mL) at room temperature was added 1,1-carbonyldiimidazole (0.343 g, 2.12 mmol) in one portion and the mixture was stirred at room temperature for one hour, then at 70° C. for two hours, whereupon acetic hydrazide (0.157 g, 2.12 mmol) was added. The resulting was stirred at room temperature for thirty minutes, then at 70° C. for two hours. After cooling to room temperature, the mixture was poured onto ice-water (100 mL) and the precipitate was filtered off and washed with water. 3,4-Dimethoxy-5-nitro-benzoic acid N'-acetyl-hydrazide was obtained as a white solid (0.296 g, 54%).

b) A suspension of the solid obtained above (0.288 g, 1.017 mmol) in phosphorus oxychloride (7 mL) was stirred at 120° C. for two hours, then allowed to cool to room temperature. The solution was then poured onto ice-water (200 mL), causing formation of a white precipitate. Extracted with dichloromethane, and the organic extracts were washed with water and brine, then dried, filtered and evaporated to leave a white solid. Recrystallisation from dichloromethane/petroleum ether gave 2-(3,4-dimethoxy-5-nitro-phenyl)-5-methyl-[1,3,4]oxadiazole as white crystals (0.151 g, 56%).

c) To a stirred solution of the solid obtained above (0.145 g, 0.547 mmol) in dichloromethane (10 mL) at −78° C. under argon was added boron tribromide (0.685 g, 2.74 mmol) dropwise. The resulting purple suspension was allowed to stir at room temperature overnight, then cooled again to −78° C. The reaction was quenched by the addition of methanol, and after stirring at room temperature for one hour, the volatiles were evaporated. Toluene (20 mL) was added to the residue and re-evaporated. The residue was triturated with boiling ethanol and filtered whilst warm to give the desired product as an orange solid (0.107 g, 82%) of m.p. 245-246° C.

EXAMPLE 6

5-[3-(3,5-Dichloro-1-oxy-pyridin-4-yl)-[1,2,4]oxadiazol-5-yl]-3-nitro-benzene-1,2-diol (Compound 7, Table 1)

a) To a stirred solution of 3,4-dibenzyloxy-5-nitrobenzoic acid (0.50 g, 1.32 mmol) in dimethylformamide (5 mL) at room temperature was added 1,1-carbonyldiimidazole (0.246 g, 1.52 mmol) in one portion, and the mixture was stirred for ninety minutes whereupon 3,5-dichloro-N'-hydroxy-1-oxyisonicotinamidine (0.337 g, 1.52 mmol) was added in one portion. The resulting mixture was stirred at room temperature overnight and then poured onto ice-water (100 mL). Brine (10 mL) was added and the precipitate was filtered off, washed with water and dissolved in 30% isopropanol/dichloromethane. The dichloromethane was then distilled off and the resulting isopropanol suspension was stored at 0° C. for one hour. The solid was then filtered off, washed with cold isopropanol and dried to leave a white solid (0.756 g, 98%).

b) A portion of this solid (0.664 g, 1.14 mmol) and 1,1-carbonyldiimidazole (0.185 g, 1.14 mmol) were dissolved in dimethylformamide (10 mL) was stirred at 100° C. for nine hours then at room temperature overnight. The resulting mixture was poured onto ice-water (100 mL) and then acidified to pH 1-2 by the dropwise addition of 2 N hydrochloric acid. The yellow precipitate that formed was filtered off, washed with water and dissolved in 10% isopropanol/dichloromethane (50 mL). The organic phase was dried, filtered and evaporated to dryness. The residue was chromatographed over silica gel using an ethyl acetate/petroleum ether (1:1) solvent mixture. Homogeneous fractions were pooled and evaporated, and the residue was recrystallised from dichloromethane/isopropanol to give 2-benzyloxy-4-[3-(3,5-dichloro-1-oxy-pyridine-4-yl)-[1,2,4]oxadiazol-5-yl]-6-nitrophenol as a yellow solid (0.263 g, 49%).

c) To a stirred suspension of the solid obtained from above (0.24 g, 0.505 mmol) in dichloromethane (5 mL) at −78° C. under argon was added boron tribromide (0.371 g, 1.5 mmol) dropwise. The resulting purple suspension was allowed to stir at room temperature for one hour, then cooled again to −78° C. and quenched by the addition of methanol. After stirring at room temperature for one hour, the solvents were removed by evaporation. The resulting yellow foam was recrystallised from dichloromethane/isopropanol to give the desired product as a yellow solid (0.153 g, 79%) of m.p. 252-253° C.

EXAMPLE 7

5-[3-(2-Chloro-1-oxy-pyridin-4-yl)-[1,2,4]oxadiazol-5-yl]-3-nitro-benzene-1,2-diol (Compound 8, Table 1)

a) To a stirred solution of 3,4-dibenzyloxy-5-nitrobenzoic acid (0.50 g, 1.32 mmol) in dimethylformamide (5 mL) at room temperature was added 1,1-carbonyldiimidazole (0.246 g, 1.52 mmol) in one portion and the mixture was stirred for one hour, whereupon 2-chloro-N'-hydroxy-1-oxy-isonicotinamidine (0.284 g, 1.52 mmol) was added in one portion. The resulting mixture was stirred at room temperature for thirty minutes, then at 140° C. for four hours. After cooling to room temperature, the mixture was poured onto water (100 mL) and acidified to pH 1-2 by the dropwise addition of 2 N hydrochloric acid. The mixture was extracted with ethyl acetate and the organic extracts were washed with water and brine, then dried, filtered and evaporated to leave an orange solid that was recrystallised from dichloromethane/isopropanol to give 4-[5-(3,4-bis-benzyloxy-5-nitro-phenyl)-[1,2,4]oxadiazol-3-yl]-2-chloro-pyridine 1-oxide as pale orange crystals (0.265 g, 38%).

b) To a stirred solution of the solid obtained above (0.25 g, 0.471 mmol) in dichloromethane (5 mL) at −78° C. under argon was added boron tribromide (0.59 g, 2.36 mmol) dropwise. The resulting deep purple suspension was allowed to stir at room temperature for one hour, then cooled again to −78° C. The reaction was quenched by the addition of methanol, and after stirring at room temperature for one hour, the solvents were removed by evaporation. Ethanol (5 mL) and toluene (20 mL) were added to the residue and re-evaporated. The residue was triturated with boiling ethanol and filtered while warm to give the desired product as yellow crystals (0.12 g, 72%) which decomposed above 300° C.

EXAMPLE 8

2,5-Dichloro-3-(5-(3,4-dihydroxy-2-nitrophenyl)-1,2,4-oxadiazol-3-yl)-4,6-dimethylpyridine 1-oxide a) To a stirred suspension of 3-hydroxy-4-methoxy-2-nitrobenzoic acid (0.900 g, 4.22 mmol) in N,N-dimethylacetamide (10.35 mL) at room temperature was added 1,1-carbonyldiimidazole (1.540 g, 9.506 mmol) in 7.65 ml of N,N-dimethylacetamide dropwise. After stirring for three hours, (Z)-2,5-dichloro-N'-hydroxy-4,6-dimethylnicotinimidamide (1.19 g, 5.107 mmol) was added in 2.7 ml of N,N-dimethylacetamide in one portion. The resulting mixture was stirred for one hour and forty five minutes then heated at 135° C. for one hour. The reaction mixture was poured onto ice/2N HCl mixture. The precipitate was filtered off, washed with water and dried under vacuum to give a yellow solid. Recrystallisation from dichloromethane/isopropanol gave 3-(3-(2,5-dichloro-4,6-dimethylpyridin-3-yl)-1,2,4-oxadiazol-5-yl)-6-methoxy-2-nitrophenol as a yellow solid (0.317 g, 18%).

b) To a stirred suspension of the solid obtained above (0.315 g, 0.766 mmol) in dichloromethane (4.3 mL) at room temperature was added urea hydrogen peroxide addition complex (0.231 g, 2.451 mmol). The resulting suspension was cooled to 0° C. and trifluoroacetic anhydride (0.483 g, 2.30 mmol) was added dropwise. The mixture was allowed to stir at room temperature for twenty four hours, then water was added and stirred for one hour. The precipitate was filtered off, washed with water and dried. The crude product was chromatographed in dichloromethane/methanol (99:1) mixture. Evaporation of pure fractions gave 2,5-dichloro-3-(5-(3-hydroxy-4-methoxy-2-nitrophenyl)-1,2,4-oxadiazol-3-yl)-4,6-dimethylpyridine 1-oxide as yellow crystals (0.195 g, 59%).

c) To a stirred suspension of the solid obtained above (0.143 g, 0.335 mmol) in N-Methylpyrrolidone (2.5 mL) at 0° C. under argon was added aluminium chloride (0.056 g, 0.42 mmol) in one portion followed by the addition of pyridine (0.106 g, 1.34 mmol). The resulting solution was heated at 60° C. for twenty-five minutes, then cooled again to room temperature and poured onto ice/2N HCl mixture. After stirring at room temperature for forty-five minutes, the precipitate was filtered off, washed with water and dried under vacuum. The crude product was recrystallized from dichloromethane/isopropanol mixture. After drying, the desired compound was obtained as yellow crystals (0.101 g, 73%) of m.p. 230° C. (dec.)

EXAMPLE 9-17

By the application of the above described technique and related procedures known to those skilled in the art and using the appropriate N-hydroxy-1-oxy-isonicotinamidines, the following compounds were prepared:
3-Nitro-5-[3-(1-oxy-2-phenyl-pyridin-4-yl)-[1,2,4]oxadiazol-5-yl]-benzene-1,2-diol, of m.p. 264-264.8° C. (compound 9, Table 1)
5-[3-(2-Furan-3-yl-1-oxy-pyridine-4-yl)-[1,2,4]oxadiazol-5-yl]-3-nitro-benzene-1,2-diol, of m.p. 304-305° C. (compound 10, Table 1)
5-[3-(2-Morpholin-4-yl-1-oxy-pyridine-4-yl)-[1,2,4]oxadiazol-5-yl]-3-nitro-benzene-1,2-diol, of m.p. 277-280° C. (compound 11, Table 1)
3-Nitro-5-[3-(1-oxy-2-thiomorpholin-4-yl-pyridin-4-yl)-[1,2,4]oxadiazol-5-yl]-benzene-1,2-diol, of m.p. 260-262° C. (compound 12, Table 1)
3-Nitro-5-[3-(1-oxy-2-phenylsulfanyl-pyridin-4-yl)-[1,2,4]oxadiazol-5-yl]-benzene-1,2-diol, of m.p. 299-301° C. (compound 13, Table 1)
3-Nitro-5-[3-(1-oxy-2-phenoxy-pyridin-4-yl)-[1,2,4]oxadiazol-5-yl]-benzene-1,2-diol, of m.p. 245-246° C. (compound 14, Table 1)
5-[3-(2,6-Dimethyl-1-oxy-pyridine-4-yl)-[1,2,4]oxadiazol-5-yl]-3-nitro-benzene-1,2-diol of, m.p. 280-282° C. (compound 15, Table 1)
5-[3-(2-Methanesulfonyl-1-oxy-pyridine-4-yl)-[1,2,4]oxadiazol-5-yl]-3-nitro-benzene-1,2-diol of, m.p. 282-285° C. (compound 16, Table 1)
5-[3-(2-Methylsulfanyl-1-oxy-pyridine-4-yl)-[1,2,4]oxadiazol-5-yl]-3-nitro-benzene-1,2-diol of, m.p. 239-240° C. (compound 17, Table 1)

EXAMPLE 18

3-Nitro-5-[3-(1-oxy-4-trifluoromethyl-pyridin-3-yl)-[1,2,4]oxadiazol-5-yl]-benzene-1,2-diol (Compound 18, Table 1)

a) To a stirred solution of 3,4-dibenzyloxy-5-nitrobenzoic acid (0.291 g, 0.769 mmol) in dimethylformamide (5 mL) at room temperature was added 1,1-carbonyldiimidazole (0.131 g, 0.808 mmol) in one portion. After stirring for ninety minutes, N'-hydroxy-1-oxy-4-trifluoromethyl-nicotinamidine (0.17 g, 0.769 mmol) was added in one portion. The resulting mixture was stirred for two hours and then poured onto ice-water (100 mL). The precipitate was filtered off, washed with water and dried in air to give a white solid (0.192 g, 43%).

b) To a stirred solution of the solid obtained above (0.192 g, 0.33 mmol) in tetrahydrofuran (10 mL) at room temperature under argon, was added a 1 N solution of tetrabutylammonium fluoride in tetrahydrofuran (1.2 mL, 1.2 mmol) dropwise. After stirring at room temperature overnight, the mixture was poured onto water (100 mL) and extracted with dichloromethane. The organic extracts were washed with water and brine, dried ($Na_2SO_4$), filtered and evaporated. The residue was chromatographed over silica gel using a dichloromethane/methanol (99:1) solvent mixture as eluent. Homogenous fractions were pooled and evaporated and the residue then recrystallised from dichloromethane/isopropanol. 3-[5-(3,4-Bis-benzyloxy-5-nitro-phenyl)-[1,2,4]oxadiazol-3-yl]-4-trifluoromethyl-pyridine 1-oxide was obtained as a white solid (0.092 g, 49%).

c) To a stirred solution of the solid obtained above (0.09 g, 0.16 mmol) in dichloromethane (5 mL) at −78° C. under argon was added boron tribromide (0.16 g, 0.64 mmol) dropwise. The resulting purple suspension was allowed to stir at room temperature for one hour, then cooled again to −78° C. and carefully quenched by the addition of water. After stirring at room temperature for one hour, the precipitate was filtered off, washed with water and dried at 50° C. under vacuum to afford the desired compound as yellow crystals (0.048 g, 79%) of m.p. 239-240° C.

EXAMPLE 19-35

By the application of the above described technique and related procedures known to those skilled in the art and using the appropriate N'-hydroxy-1-oxy-isonicotinamidines, the following compounds were prepared:
5-[3-(5-Bromo-1-oxy-pyridin-3-yl)-[1,2,4]oxadiazol-5-yl]-3-nitro-benzene-1,2-diol, of m.p. 258-260° C. (compound 19, Table 1)
5-[3-(6-Methyl-1-oxy-pyridin-3-yl)-[1,2,4]oxadiazol-5-yl]-3-nitro-benzene-1,2-diol, of m.p. 325-326° C. (compound 20, Table 1)
5-[3-(4-Methyl-1-oxy-pyridin-3-yl)-[1,2,4]oxadiazol-5-yl]-3-nitro-benzene-1,2-diol, of m.p. 297° C. (compound 21, Table 1)
3-Nitro-5-[3-(1-oxy-5-phenyl-pyridin-3-yl)-[1,2,4]oxadiazol-5-yl]-benzene-1,2-diol, of m.p. 288-289° C. (compound 22, Table 1)
5-[3-(6-Chloro-1-oxy-pyridin-3-yl)-[1,2,4]oxadiazol-5-yl]-3-nitro-benzene-1,2-diol, of m.p. 268-270° C. (compound 23, Table 1)
5-[3-(2-Chloro-1-oxy-pyridin-3-yl)-[1,2,4]oxadiazol-5-yl]-3-nitro-benzene-1,2-diol, of m.p. 265-267° C. (compound 24, Table 1)
5-[3-(2-Chloro-6-methyl-1-oxy-pyridin-3-yl)-[1,2,4]oxadiazol-5-yl]-3-nitro-benzene-1,2-diol, of m.p. 218-220° C. (compound 25, Table 1)
5-[3-(2-Morpholin-4-yl-1-oxy-pyridin-3-yl)-[1,2,4]oxadiazol-5-yl]-3-nitro-benzene-1,2-diol, of m.p. 175-177° C. (compound 26, Table 1)
5-[3-(6-Methylsulfanyl-1-oxy-pyridin-3-yl)-[1,2,4]oxadiazol-5-yl]-3-nitro-benzene-1,2-diol, of m.p. 264-266° C. (compound 27, Table 1)

3-Nitro-5-[3-(1-oxy-6-trifluoromethyl-pyridin-3-yl)-[1,2,4]oxadiazol-5-yl]-benzene-1,2-diol, of m.p. 269.5-271.3° C. (compound 28, Table 1)

5-[3-(2-Methyl-1-oxy-6-trifluoromethyl-pyridin-3-yl)-[1,2,4]oxadiazol-5-yl]-3-nitro-benzene-1,2-diol, of m.p. 240-242° C. (compound 29, Table 1)

5-[3-(6-Methyl-1-oxy-4-trifluoromethyl-pyridin-3-yl)-[1,2,4]oxadiazol-5-yl]-3-nitro-benzene-1,2-diol, of m.p. 250-252.5° C. (compound 30, Table 1)

5-[3-(2,6-Dimethyl-1-oxy-4-trifluoromethyl-pyridin-3-yl)-[1,2,4]oxadiazol-5-yl]-3-nitro-benzene-1,2-diol, of m.p. 252-253° C. (compound 31, Table 1)

5-[3-(2-Methyl-1-oxy-6-phenyl-4-trifluoromethyl-pyridin-3-yl)-[1,2,4]oxadiazol-5-yl]-3-nitro-benzene-1,2-diol, of m.p. 256-256.5° C. (compound 32, Table 1)

5-[3-(6-Methyl-1-oxy-2-phenyl-4-trifluoromethyl-pyridin-3-yl)-[1,2,4]oxadiazol-5-yl]-3-nitro-benzene-1,2-diol, of m.p. 237-239° C. (compound 33, Table 1)

3-Nitro-5-[3-(1-oxy-quinolin-4-yl)-[1,2,4]oxadiazol-5-yl]-benzene-1,2-diol, of m.p. 306-307° C. (compound 34, Table 1)

3-Nitro-5-[3-(1-oxy-quinolin-3-yl)-[1,2,4]oxadiazol-5-yl]-benzene-1,2-diol, of m.p. 276-277° C. (compound 35, Table 1)

3-Nitro-5-[3-(1-oxy-2-trifluoromethyl-pyridin-3-yl)-[1,2,4]oxadiazol-5-yl]-benzene-1,2-diol, of m.p. 253-254° C. (compound 42, Table 1)

EXAMPLE 36

5-[3-(2-Bromo-6-methyl-1-oxy-pyridin-3-yl)-[1,2,4]oxadiazol-5-yl]-3-nitro-benzene-1,2-diol (Compound 36, Table 1)

a) To a stirred solution of 3,4-dibenzyloxy-5-nitrobenzoic acid (1.355 g, 3.576 mmol) in dimethylformamide (10 mL) at room temperature was added 1,1-carbonyldiimidazole (0.667 g, 4.113 mmol) in one portion. After stirring for ninety minutes, 2-bromo-N'-hydroxy-6-methylnicotinamidine (0.946 g, 4.113 mmol) was added and the mixture was stirred overnight then poured onto water (100 mL). Brine (10 mL) was added and the precipitate was filtered off, washed with water and dissolved in dichloromethane (50 mL). The organic layer was washed with water and brine, then dried (Na$_2$SO$_4$), filtered and evaporated to leave a white foam (1.91 g, 90%).

b) To a solution of the solid obtained above (1.91 g, 3.23 mmol) in dimethylformamide (30 mL) was added 1,1-carbonyldiimidazole (0.576 g, 3.55 mmol) and the resulting mixture was stirred at 120° C. for three hours, then allowed to cool to room temperature. Poured onto ice-water (150 mL) and acidified to pH 1-2 by the dropwise addition of 2 N hydrochloric acid. The mixture was extracted with dichloromethane and the organic extracts were washed with water and brine, then dried (Na$_2$SO$_4$), filtered and evaporated to leave an orange solid. Recrystallisation from dichloromethane/ethanol gave 3-[5-(3,4-bis-benzyloxy-5-nitro-phenyl)-[1,2,4]oxadiazol-3-yl]-2-bromo-6-methyl-pyridine as an orange solid (0.702 g, 38%).

c) To a stirred solution of the solid obtained above (0.609 g, 1.063 mmol) in dichloromethane (15 mL) at room temperature was added urea hydrogen peroxide addition complex (0.525 g, 5.579 mmol). The resulting suspension was cooled to 0° C. and trifluoroacetic anhydride (1.12 g, 5.314 mmol) was added dropwise. The mixture was allowed to stir at room temperature for five hours, then the insoluble material was filtered off and washed with a small volume of dichloromethane. The combined filtrate was stirred with a 10% aqueous solution of sodium metabisulphite (10 mL) for fifteen minutes to destroy excess peroxides, then the phases were separated. The organic phase was washed with water, a saturated aqueous solution of sodium bicarbonate, water again and brine, then dried (Na$_2$SO$_4$), filtered and evaporated to leave a white solid. Recrystallisation twice from dichloromethane/ethanol gave 3-[5-(3,4-bis-benzyloxy-5-nitro-phenyl)-[1,2,4]oxadiazol-3-yl]-2-bromo-6-methyl-pyridine 1-oxide as white crystals (0.344 g, 55%).

d) To a stirred solution of the solid obtained above (0.337 g, 0.572 mmol) in dichloromethane (10 mL) at −78° C. under argon was added boron tribromide (0.717 g, 2.86 mmol) dropwise. The resulting purple suspension was stirred at room temperature for one hour, then cooled again to −78° C. and quenched by the addition of methanol. After stirring at room temperature for one hour, the solvents were evaporated. Ethanol (5 mL) and toluene (20 mL) were added to the residue and re-evaporated. The residue was stirred in boiling ethanol and filtered while still warm. After drying, the desired compound was obtained as orange crystals (0.187 g, 80%) of m.p. 246-247° C.

EXAMPLE 37-41

By the application of the above described technique and related procedures known to those skilled in the art and using the appropriate N'-hydroxy-nicotinamidines, the following compounds were prepared:

5-[3-(2-Chloro-4,6-dimethyl-1-oxy-pyridin-3-yl)-[1,2,4]oxadiazol-5-yl]-3-nitro-benzene-1,2-diol, of m.p. 234-235° C. (compound 37, Table 1)

5-[3-(2-Bromo-4,6-dimethyl-1-oxy-pyridin-3-yl)-[1,2,4]oxadiazol-5-yl]-3-nitro-benzene-1,2-diol, of m.p. 205-207° C. (compound 38, Table 1)

3-Nitro-5-[3-(1'-oxy-pyridin-3-ylmethyl)-[1,2,4]oxadiazol-5-yl]-benzenediol, of m.p. 232° C. (compound 39, Table 1)

3-Nitro-5-[3-(1'-oxy-6-trifluoromethyl-pyridine-3-ylmethyl)-[1,2,4]oxadiazol-5-yl]-benzene-1,2-diol, of m.p. 195.2° C. (compound 43, Table 1)

3-Nitro-5-[3-(1'-oxy-5-trifluoromethyl-pyridin-2-yloxymethyl)-[1,2,4]oxadiazol-5-yl]-benzene-1,2-diol, of m.p. 222° C. (compound 44, Table 1)

EXAMPLE 42

5-[3-(2-Bromo-4,5,6-trimethyl-1-oxy-pyridin-3-yl)-[1,2,4]oxadiazol-5-yl]-3-nitrobenzene-1,2-diol (Compound 40, Table 1)

a) To a stirred solution of 3,4-dibenzyloxy-5-nitrobenzoic acid (0.945 g, 2.49 mmol) in dimethylformamide (10 mL) at room temperature was added 1,1-carbonyldiimidazole (0.465 g, 2.87 mmol) in one portion, and the resulting mixture was stirred for two hours, whereupon 2-bromo-N'-hydroxy-4,5,6-trimethyl-nicotinamidine (0.74 g, 2.87 mmol) was added in one portion. The resulting mixture was allowed to stir at room temperature overnight, and then poured onto water (150 mL). Brine (10 mL) was added, and the resulting precipitate was filtered off and washed with water. The solid was then dissolved in dichloromethane (50 mL) and the organic phase was washed with water and brine, then dried, filtered and evaporated to leave an off-white solid (1.40 g, 91%).

b) To a stirred solution of the solid obtained above (1.39 g, 2.245 mmol) in tetrahydrofuran (20 mL) at room temperature under argon was added a 1 N solution of tetrabutylammonium fluoride in tetrahydrofuran (2.47 mL, 2.47 mmol). After stirring at room temperature overnight, the almost black reaction mixture was poured onto water (150 mL) and extracted with dichloromethane. The organic extracts were washed with water and brine, then dried, filtered and evaporated to leave a brown oil. Addition of dichloromethane (4 mL) and diethyl ether (4 mL) caused formation of a precipitate that was filtered off and recrystallised from isopropanol. 3-[5-(3,4-Bis-benzyloxy-5-nitro-phenyl)-[1,2,4]oxadiazol-3-yl]-2-bromo-4,5,6-trimethyl-pyridine was obtained as a beige solid (0.879 g, 65%).

c) To a stirred solution of the pyridine obtained from above (0.621 g, 1.033 mmol) in dichloromethane (20 mL) at room temperature was added urea hydrogen peroxide complex (1.018 g, 10.82 mmol) in one portion. The resulting suspension was cooled in an ice-water bath and trifluoroacetic anhydride (2.23 g, 10.62 mmol) was added dropwise. The resulting suspension was stirred in the cold for fifteen minutes and then allowed to stir at room temperature overnight. The insoluble material was then filtered off and washed with a small volume of dichloromethane. The combined filtrate was stirred with a 10% aqueous solution of sodium metabisulphite for fifteen minutes and then the phases were separated. The organic phase was washed with water, a saturated aqueous solution of sodium bicarbonate, water again and brine, then dried, filtered and evaporated to leave a foamy pale orange solid. This solid was chromatographed over silica gel using a petroleum ether/ethyl acetate (1:1) mixture as eluent. Homogenous product containing fractions were pooled and evaporated. 3-[5-(3,4-Bis-benzyloxy-5-nitro-phenyl)-[1,2,4]oxadiazol-5-yl]-2-bromo-4,5,6-trimethyl-pyridine 1-oxide was obtained as a foamy pale yellow solid (0.342 g, 54%).

d) To a stirred solution of the solid obtained above (0.325 g, 0.527 mmol) in dichloromethane (10 mL) at −78° C. under argon was added boron tribromide (0.66 g, 2.633 mmol) dropwise. The resulting deep purple suspension was allowed to stir at room temperature for one hour, then cooled again to −78° C. and carefully quenched by the dropwise addition of methanol. After stirring at room temperature for one hour, the solvents were removed by evaporation. Toluene (20 mL) and ethanol (5 mL) were added to the residue and re-evaporated. The resulting yellow solid was triturated with boiling ethanol (15 mL) and filtered whilst warm. The desired product was obtained as a yellow solid (0.172 g, 75%) of m.p. 242-243° C.

EXAMPLE 43-46

By the application of the above described technique and related procedures known to those skilled in the art and using the appropriate N'-hydroxy-nicotinamidine, the following compounds were prepared:

5-[3-(2-Chloro-4,5,6-trimethyl-1-oxy-pyridin-3-yl)-[1,2,4]oxadiazol-5-yl]-3-nitrobenzene-1,2-diol, m.p. 246-247.3° C. (compound 41, Table 1)

5-[3-(2,5-Dichloro-4,6-dimethyl-1-oxy-pyridin-3-yl)-[1,2,4]oxadiazol-5-yl]-3-nitrobenzene-1,2-diol, m.p. 237-240° C. (compound 45, Table 1)

3-Nitro-5-[3-(4,5,6-trimethyl-1-oxy-pyridin-3-yl)-[1,2,4]oxadiazol-5-yl]-benzene-1,2-diol, m.p. 255-256° C. (compound 46, Table 1)

5-[3-(2-Bromo-5-chloro-4,6-dimethyl-1-oxy-pyridin-3-yl)-[1,2,4]oxadiazol-5-yl]-3-nitrobenzene-1,2-diol, m.p. 227-228° C. (compound 47, Table 1)

EXAMPLE 47

As an example of a compound of the general formula (I) having a 2H-pyrazol-1,5-diyl moiety as central unit, 3-nitro-5-[2-(1-oxy-2-trifluormethyl-pyridin-3-yl)-2H-pyrazol-3-yl]-benzene-1,2-diol was prepared by the following procedure:

a) To a stirred solution of 1-(3,4-dimethoxy-5-nitro-phenyl)-3-dimethylamino-prop-2-en-1-one (0.5 g, 1.79 mmol) and (2-trifluoromethyl-pyridin-3-yl)-hydrazine (0.33 g, 1.87 mmol) in ethanol (10 mL) was added 10 drops of concentrated hydrochloric acid and the mixture was heated at reflux for two hours. The mixture was allowed to cool to room temperature and the resulting precipitate was filtered off, washed with ethanol and dried to give 3-[5-(3,4-dimethoxy-5-nitro-phenyl)-pyrazol-1-yl]-2-trifluoromethyl-pyridine, 0.58 g (82%).

b) To a solution of 3-[5-(3,4-dimethoxy-5-nitro-phenyl)-pyrazol-1-yl]-2-trifluoromethyl-pyridine (0.50 g, 1.27 mmol) in dichloromethane (10 mL) cooled in an ice-water bath was added urea-hydrogen peroxide complex (0.26 g, 2.76 mmol) in one portion followed by trifluoroacetic anhydride (0.53 g, 2.52 mmol) dropwise. The resulting mixture was allowed to stir at room temperature overnight and then the insoluble material was filtered off. The filtrate was washed with water and brine, then dried over anhydrous sodium sulphate, filtered and evaporated to leave an off-white solid. Recrystallisation from ethanol afforded 3-[5-(3,4-dimethoxy-5-nitro-phenyl)-pyrazol-1-yl]-2-trifluoromethyl-pyridine 1-oxide, 0.34 g (65%).

c) A suspension of 3-[5-(3,4-dimethoxy-5-nitro-phenyl)-pyrazol-1-yl]-2-trifluoromethyl-pyridine 1-oxide (0.3 g, 0.73 mmol) in 48% aqueous hydrobromic acid (10 mL) was stirred at 140° C. for one hour and then allowed to cool to room temperature. The mixture was then poured onto ice-water (100 mL) and the resulting yellow precipitate was filtered off, washed with water and dried to give 3-nitro-5-[2-(1-oxy-2-trifluormethyl-pyridin-3-yl)-2H-pyrazol-3-yl]-benzene-1,2-diol, 0.16 g (57%).

EXAMPLE 48

As an example of a compound of the general formula (I) having a 1,3,4-oxadiazol-2,5-diyl moiety as central unit, 3-nitro-5-[5-(1-oxy-2-trifluoromethyl-pyridin-3-yl)-[1,3,4]oxadiazol-2-yl]-benzene-1,2-diol was prepared by the following procedure:

a) A mixture of 3,4-dimethoxy-5-nitrobenzoic acid (0.53 g, 2.34 mmol) and 1,1-carbonyldiimidazole (0.42 g, 2.59 mmol) was heated in tetrahydrofuran (10 mL) at reflux for three hours and then cooled to room temperature. 2-Trifluoromethyl-nicotinic acid hydrazide (0.53 g, 2.57 mmol) was added in one portion and the yellowish mixture was stirred at reflux overnight and then allowed to cool to room temperature. The mixture was poured onto cold water (100 mL) and the copious precipitate was filtered off, washed with water and dried to give 2-trifluoromethyl-nicotinic acid N'-(3,4-dimethoxy-5-nitro-benzoyl)-hydrazide, 0.71 g (73%).

b) A suspension of 2-trifluoromethyl-nicotinic acid N'-(3,4-dimethoxy-5-nitro-benzoyl)-hydrazide (0.60 g, 1.44 mmol) in phosphorus oxychloride (10 mL) was stirred at 130° C. for three hours, becoming a pale yellow solution. The mixture was allowed to cool to room temperature and then poured onto ice-water (200 mL). The white precipitate was filtered off, washed with water and dried to give 3-[5-(3,4-dimethoxy-5-nitro-phenyl)-[1,3,4]oxadiazol-2-yl]-2-trifluoromethyl-pyridine, 0.48 g (84%).

c) To a stirred solution of 3-[5-(3,4-dimethoxy-5-nitro-phenyl)-[1,3,4]oxadiazol-2-yl]-2-trifluoromethyl-pyridine (0.45 g, 1.13 mmol) in dichloromethane (10 mL)) cooled in an ice-water bath was added urea hydrogen peroxide complex (0.23 g, 2.45 mmol) in one portion followed by trifluoroacetic anhydride (0.47 g, 2.24 mmol) dropwise. The resulting mixture was allowed to stir at room temperature overnight and then the insoluble material was filtered off. The filtrate was washed with water and brine, then dried over anhydrous sodium sulphate, filtered and evaporated to leave an off-white solid. Recrystallisation from ethanol afforded 3-[5-(3,4-dimethoxy-5-nitro-phenyl)-[1,3,4]oxadiazol-2-yl]-2-trifluoromethyl-pyridine 1-oxide, 0.39 g (83%).

d) A suspension of 3-[5-(3,4-dimethoxy-5-nitro-phenyl)-[1,3,4]oxadiazol-2-yl]-2-trifluoromethyl-pyridine 1-oxide (0.30 g, 0.73 mmol) in a mixture of 48% hydrobromic acid (5 mL) and 30% hydrogen bromide in acetic acid (5 mL) was heated at 140° C. overnight and then allowed to cool to room temperature. After evaporation to dryness under reduced pressure, toluene (10 mL) was added to the residue and re-evaporated under reduced pressure. The resulting solid was recrystallised from isopropanol to give 3-nitro-5-[5-(1-oxy-2-trifluoromethyl-pyridin-3-yl)-[1,3,4]oxadiazol-2-yl]-benzene-1,2-diol as a yellow solid, 0.19 g, (68%).

EXAMPLE 49

As an example of a compound of the general formula (I) having a pyrimidin-2,4-diyl moiety as central unit, 3-nitro-5-[2-(1-oxy-2-trifluoromethyl-pyridine-3-yl)-pyrimidin-4-yl]-benzene-1,2-diol was prepared by the following procedure:

a) A stirred suspension of 1-(3,4-dimethoxy-5-nitro-phenyl)-3-dimethylamino-prop-2-en-1-one (0.28 g, 1.0 mmol), 1-oxy-2-trifluoromethyl-nicotinamidine (0.31 g, 1.5 mmol) and potassium tert-butoxide (0.17 g, 1.5 mmol) in absolute ethanol (5 mL) was heated to 80° C. in a sealed tube for one hour and then allowed to cool to room temperature. The mixture was poured onto cold water (100 mL) and the resulting precipitate was filtered off, washed with water and dried to give 4-(3,4-dimethoxy-5-nitro-phenyl)-2-(1-oxy-2-trifluoromethyl-pyridin-3-yl)-pyrimidine, 0.31 g (73%).

b) A suspension of 4-(3,4-dimethoxy-5-nitro-phenyl)-2-(1-oxy-2-trifluoromethyl-pyridin-3-yl)-pyrimidine (0.25 g, 0.59 mmol) in 48% hydrobromic acid (5 mL) was stirred at 140° C. for four hours and then allowed to cool to room temperature. The mixture was poured onto ice-water (100 mL) and the resulting filtrate was filtered off, washed with water and dried to give 3-nitro-5-[2-(1-oxy-2-trifluoromethyl-pyridine-3-yl)-pyrimidin-4-yl]-benzene-1,2-diol, 0.21 g (90%).

EXAMPLE 50

As an example of a compound of the general formula (I) having a benzene-1,3-diyl moiety as central unit, 5-nitro-3'-(1-oxy-6-trifluoromethyl-pyridin-2-yl)-biphenyl-3,4-diol was prepared by the following procedure:

a) To a stirred solution of 4-benzyloxy-3-methoxyphenyl-boronic acid (1.0 g, 3.87 mmol) and 2-(3-bromo-phenyl)-6-trifluoromethyl-pyridine 1-oxide (1.12 g, 3.52 mmol) in toluene (10 mL) and ethanol (1 mL) at room temperature under argon was added 2 N aqueous sodium carbonate solution (5.41 mL, 10.82 mmol) followed by tetrakis(triphenylphosphine)palladium (0.22 g, 0.19 mmol). The resulting mixture was stirred at 90° C. for two hours and then allowed to cool to room temperature. The phases were separated and the aqueous phase was extracted with toluene (5 mL). The combined organic phases were washed with water and brine, then dried over anhydrous sodium sulphate and filtered. Evaporation of the solvent left a brown oil that was chromatographed over silica gel (petroleum ether/ethyl acetate, 9:1) to give 2-(4'-benzyloxy-3'-methoxybiphenyl-3-yl)-6-trifluoromethyl-pyridine 1-oxide as a clear oil, 1.11 g (70%).

b) To a solution of 2-(4'-benzyloxy-3'-methoxybiphenyl-3-yl)-6-trifluoromethyl-pyridine 1-oxide (1.10 g, 2.44 mmol) in dichloromethane (20 mL) cooled in an ice-water bath was added a 30% solution of hydrogen bromide in acetic acid (4 mL, 20 mmol) dropwise. The resulting solution was allowed to stir at room temperature for six hours then poured onto ice-water (100 mL). The phases were separated and the aqueous phase was extracted with dichloromethane (10 mL). The combined organic layers were washed with water and brine, then dried over anhydrous sodium sulphate and filtered. Evaporation of the solvent left a brown oil that was chromatographed over silica gel (petroleum ether/ethyl acetate, 4:1) to give 3-methoxy-3'-(1-oxy-6-trifluoromethyl-pyridin-2-yl)-biphenyl-4-ol as a clear oil, 0.57 g (65%).

c) To a solution of 3-methoxy-3'-(1-oxy-6-trifluoromethyl-pyridin-2-yl)-biphenyl-4-ol (0.50 g, 1.38 mmol) in acetic acid (10 mL) at room temperature was added 60% nitric acid (0.12 mL, 1.52 mmol) dropwise. The resulting mixture was allowed to stir for thirty minutes then poured onto ice-water (100 mL) and the resulting precipitate was filtered off, washed with water and dried. After chromatography over silica gel (petroleum ether/ethyl acetate, 2:1), 5-methoxy-3-nitro-3'-(1-oxy-6-trifluoromethyl-pyridin-2-yl)-biphenyl-4-ol was obtained as a yellow solid, 0.34 g (60%).

d) To a stirred solution of 5-methoxy-3-nitro-3'-(1-oxy-6-trifluoromethyl-pyridin-2-yl)-biphenyl-4-ol (0.30 g, 0.738 mmol) in 1,2-dichloroethane (10 mL) cooled in an ice-water bath was added aluminium chloride (0.123 g, 0.922 mmol) in one portion followed by pyridine (0.233 g, 2.95 mmol) dropwise. The resulting red suspension was stirred at 80° C. for two hours, then cooled to room temperature and poured onto cold 2 N aqueous hydrochloric acid (100 mL). The precipitate was filtered off, washed with water and dried to give 5-nitro-3'-(1-oxy-6-trifluoromethyl-pyridin-2-yl)-biphenyl-3,4-diol, 0.17 g, (59%).

EXAMPLE 51

As an example of a compound of the general formula (I) having a carbonyl moiety as central unit, (3,4-dihydroxy-5-nitro-phenyl)-(1-oxy-2-trifluoromethyl-pyridin-3-yl)-methanone was prepared by the following procedure:

a) To a solution of 4-benzyloxy-3-methoxy-bromobenzene (2.0 g, 6.82 mmol) in tetrahydrofuran (50 mL) at −78° C. under argon was added 2 N butyllithium solution in hexanes (3.75 mL, 7.5 mmol) dropwise. The resulting mixture was allowed to stir for one hour, whereupon a solution of N-methoxy-N-methyl-2-trifluoromethyl-nicotinamide (1.76 g, 7.5 mmol) in tetrahydrofuran (20 mL) was added dropwise. The mixture was then allowed to reach room temperature over two hours, then poured onto cold 2 N aqueous hydrochloric acid (150 mL). The mixture was extracted with diethylether, and the combined organic layers were washed with water and brine, dried over anhydrous sodium sulphate and filtered. Evaporation of the solvent left a brown oil that was chromatographed over silica gel (petroleum ether/ethyl acetate, 2:1) to give (4-benzyloxy-3-methoxy-phenyl)-(2-trifluoromethyl-pyridin-3-yl)-methanone, 1.72 g (65%).

b) To a stirred solution of (4-benzyloxy-3-methoxy-phenyl)-(2-trifluoromethyl-pyridin-3-yl)-methanone (1.60 g, 4.13 mmol) in dichloromethane (20 mL) cooled in an ice-water bath was added urea hydrogen peroxide complex (0.85 g, 9.08 mmol) in one portion followed by trifluoroacetic anhydride (1.73 g, 8.26 mmol) dropwise. The resulting mixture was then allowed to stir at room temperature overnight, whereupon insoluble material was filtered off and washed with dichloromethane (5 mL). The combined filtrate was washed with water and brine, then dried over anhydrous sodium sulphate and filtered. Evaporation of the solvent left an orange solid that was recrystallised from ethanol to give (4-benzyloxy-3-methoxy-phenyl)-(1-oxy-2-trifluoromethyl-pyridin-3-yl)-methanone, 1.0 g (60%).

c) To a stirred solution of (4-benzyloxy-3-methoxy-phenyl)-(1-oxy-2-trifluoromethyl-pyridin-3-yl)-methanone (0.95 g, 2.36 mmol) in dichloromethane cooled in an ice-water bath was added dropwise a 30% solution of hydrogen bromide in acetic acid (3.54 mL, 17.7 mmol). The resulting solution was allowed to stir at room temperature overnight then poured onto ice-water (100 mL). The phases were separated and the aqueous phase extracted with dichloromethane (10 mL). The combined organic layers were washed with water and brine, then dried over anhydrous sodium sulphate and filtered. Evaporation of the solvent left a brown oil that was chromatographed over silica gel (petroleum ether/ethyl acetate, 1:1) to give (4-hydroxy-3-methoxy-phenyl)-(1-oxy-2-trifluoromethyl-pyridin-3-yl)-methanone as a colourless solid, 0.59 g (80%).

d) To a solution of (4-hydroxy-3-methoxy-phenyl)-(1-oxy-2-trifluoromethyl-pyridin-3-yl)-methanone (0.50 g, 1.59 mmol) in acetic acid (10 mL) at room temperature was added 60% nitric acid (0.14 mL, 1.75 mmol) dropwise. The resulting mixture was allowed to stir for thirty minutes then poured onto ice-water (100 mL) and the resulting precipitate was filtered off, washed with water and dried. Recrystallisation from ethanol afforded (4-hydroxy-3-methoxy-5-nitro-phenyl)-(1-oxy-2-trifluoromethyl-pyridin-3-yl)-methanone as a yellow solid, 0.33 g (58%).

e) To a stirred solution of (4-hydroxy-3-methoxy-5-nitro-phenyl)-(1-oxy-2-trifluoromethyl-pyridin-3-yl)-methanone (0.30 g, 0.84 mmol) in 1,2-dichloroethane (10 mL) cooled in an ice-water bath was added aluminium chloride (0.14 g, 1.05 mmol) in one portion followed by pyridine (0.26 g, 3.35 mmol) dropwise. The resulting red suspension was stirred at 80° C. for two hours, then cooled to room temperature and poured onto cold 2 N aqueous hydrochloric acid (100 mL). The precipitate was filtered off, washed with water and dried to give (3,4-dihydroxy-5-nitro-phenyl)-(1-oxy-2-trifluoromethyl-pyridin-3-yl)-methanone, 0.19 g, (66%).

EXAMPLE 52

As an example of a compound of the general formula (I) having a (Z)-1-cyanoethen-1,2-diyl moiety as central unit, 3-(3,4-dihydroxy-5-nitro-phenyl)-2-(1-oxy-6-trifluoromethyl-pyridin-3-yl)-acrylonitrile was prepared by the following procedure:

a) A suspension of vanillin (1.0 g, 6.57 mmol), (1-oxy-6-trifluoromethyl-pyridin-3-yl)-acetonitrile (1.33 g, 6.57 mmol) and piperidine (0.71 mL, 7.23 mmol) in absolute ethanol (10 mL) was stirred at reflux for forty-eight hours and then allowed to cool to room temperature. The resulting precipitate was filtered off, washed with water and dried. Recrystallisation from isopropanol afforded 3-(4-hydroxy-3-methoxy-phenyl)-2-(1-oxy-6-trifluoromethyl-pyridin-3-yl)-acrylonitrile as white crystals, 0.95 g (43%).

b) To a solution of 3-(4-hydroxy-3-methoxy-phenyl)-2-(1-oxy-6-trifluoromethyl-pyridin-3-yl)-acrylonitrile (0.90 g, 2.68 mmol) in acetic acid (20 mL) was added 60% nitric acid (0.23 mL, 2.95 mmol) dropwise. The resulting mixture was allowed to stir at room temperature for thirty minutes then poured onto ice-water (100 mL). The yellow precipitate was filtered off, washed with water and dried. Recrystallisation from isopropanol afforded 3-(4-hydroxy-3-methoxy-5-nitro-phenyl)-2-(1-oxy-6-trifluoromethyl-pyridin-3-yl)-acrylonitrile as a yellow solid, 0.63 g, (62%).

c) To a stirred solution of 3-(4-hydroxy-3-methoxy-5-nitro-phenyl)-2-(1-oxy-6-trifluoromethyl-pyridin-3-yl)-acrylonitrile (0.55 g, 1.44 mmol) in 1,2-dichloroethane (10 mL) cooled in an ice-water bath was added aluminium chloride (0.24 g, 1.80 mmol) in one portion followed by pyridine (0.46 g, 5.77 mmol) dropwise. The resulting red suspension was stirred at 80° C. for two hours, then cooled to room temperature and poured onto cold 2 N aqueous hydrochloric acid (100 mL). The precipitate was filtered off, washed with water and dried to give 3-(3,4-dihydroxy-5-nitro-phenyl)-2-(1-oxy-6-trifluoromethyl-pyridin-3-yl)-acrylonitrile, 0.32 g (60%).

EXAMPLE 53

As an example of a compound of the general formula (I) having a 1H-imidazol-1,5-diyl moiety as central unit, 2-(5-(3,4-dihydroxy-5-nitrophenyl)-1H-imidazol-1-yl)-5-(trifluoromethyl)pyridine 1-oxide was prepared by the following procedure:

a) To a stirred solution of 2-amino-5-(trifluoromethyl) pyridine 1-oxide (0.445 g, 2.5 mmol) in a mixture of ethanol (12.5 mL) and acetic acid (0.25 mL) at room temperature was added 3,4-dimethoxy-5-nitrobenzaldehyde (0.53 g, 2.5 mmol). The reaction was heated at reflux temperature for two hours then ethanol was evaporated. The oily residue was dissolved in a mixture of methanol (17 mL) and 1,2-dimethoxyethane (7.5 mL), whereupon 1-(isocyanomethyl-sulfonyl)-4-methylbenzene (TOSMIC) (0.73 g, 3.75 mmol) and potassium carbonate (0.69 g, 5 mmol) were added in one portion. The resulting mixture was stirred at reflux temperature for 3 hours. The reaction was evaporated to dryness, and then taken up in dichloromethane (50 ml). The organic phase was washed with water (50 mL) and then dried over anhydrous magnesium sulphate, filtered and evaporated to leave brown oil. Column chromatography over silica gel (petroleum ether-ethyl acetate 9:1) gave 2-(5-(3,4-dimethoxy-5-nitrophenyl)-1H-imidazol-1-yl)-5-(trifluoromethyl)pyridine 1-oxide, 0.56 g (55%).

b) 2-(5-(3,4-Dimethoxy-5-nitrophenyl)-1H-imidazol-1-yl)-5-(trifluoromethyl)pyridine 1-oxide (0.41 g, 1 mmol) was heated at 140° C. in 48% aqueous hydrogen bromide (6 mL) for 2.5 hours. The dark homogeneous solution was cooled to room temperature and volatiles were removed by evaporation to leave a pale brown crystalline solid that was dried over $P_2O_5$ under vacuum. Trituration of the resulting solid with diethyl ether gave 2-(5-(3,4-dihydroxy-5-nitrophenyl)-1H-imidazol-1-yl)-5-(trifluoromethyl)pyridine 1-oxide as a yellow crystalline solid, 0.27 g (71%).

EXAMPLE 54

As an example of a compound of the general formula (I) having a isoxazo-3,5-diyl moiety as central unit, 3-(3-(3,4- dihydroxy-5-nitrophenyl)isoxazol-5-yl)-2-(trifluoromethyl) pyridine 1-oxide was prepared by the following procedure:

a) To a stirred suspension of (E)-3-(3-(3,4-dimethoxy-5-nitrophenyl)acryloyl)-2-(trifluoromethyl)pyridine 1-oxide (1.19 g, 3 mmol) in ethanol (15 mL) was added 50% aqueous hydroxylamine solution (0.74 mL, 4.5 mmol) and the mixture was heated to 80° C. After stirring for 1 hour, a fine precipitate began to separate from the reaction mixture. After cooling to room temperature the yellow precipitate was filtered off, washed with ethanol and dried under vacuum to give 3-(3-(3,4-dimethoxy-5-nitrophenyl)-5-hydroxy-4,5-dihydroisoxazol-5-yl)-2-(trifluoromethyl)pyridine 1-oxide, 0.94 g (73%).

b) 3-(3-(3,4-dimethoxy-5-nitrophenyl)-5-hydroxy-4,5-dihydroisoxazol-5-yl)-2-(trifluoromethyl)pyridine 1-oxide (2.14 g, 5 mmol) was heated in 20 mL of ethyl acetate to 70° C. To the resulting slurry was added trifluoroacetic acid (0.74 g, 6.5 mmol) dropwise. After 10 minutes, the reaction was evaporated to dryness and the residue was recrystallised from isopropanol to give 3-(3-(3,4-dimethoxy-5-nitrophenyl)isoxazol-5-yl)-2-(trifluoromethyl)pyridine 1-oxide, 1.27 g (62%).

c) 3-(3-(3,4-dimethoxy-5-nitrophenyl)isoxazol-5-yl)-2-(trifluoromethyl) pyridine 1-oxide (0.81 g, 2 mmol) was taken up in dichloromethane (15 mL) and the yellowish suspension was cooled to −78° C. under argon whereupon boron tribromide (4.5 g, 18 mmol) was added dropwise. The reddish reaction mixture was allowed to warm to room temperature and stirred for 18 hours, then carefully poured into ice-water (100 mL) and allowed to stir for 1 hour. The yellow precipitate was filtered off, washed with water and dried over $P_2O_5$ under vacuum. Trituration with boiling ethanol gave 3-(3-(3,4-dihydroxy-5-nitrophenyl)isoxazol-5-yl)-2-(trifluoromethyl)pyridine 1-oxide as a yellow solid, 0.49 g (64%).

EXAMPLE 55

As an example of a compound of the general formula (I) having a furan-2,4-diyl moiety as central unit, 3-(4-(3,4-dihydroxy-5-nitrophenyl)-3-(ethoxycarbonyl)furan-2-yl)-2-(trifluoromethyl)pyridine-1-oxide was prepared by the following procedure:

a) To a stirred solution of 3-(3-ethoxy-3-oxopropanoyl)-2-(trifluoromethyl)pyridine-1-oxide (1.39 g, 5 mmol) in pyridine (25 mL) was added 2-bromo-1-(3,4-dimethoxy-5-nitrophenyl)ethanone (1.67 g, 5.5 mmol). The reaction mixture was heated to 70° C. and stirred for 5 hours, then cooled to room temperature and poured onto 6 N aqueous HCl (100 mL). The precipitate was filtered off, washed with water and dried over $P_2O_5$ under vacuum. The solid was recrystallised from dichloromethane/ispropanol to give crude 3-(4-(3,4-dimethoxy-5-nitrophenyl)-3-(ethoxycarbonyl)furan-2-yl)-2-(trifluoromethyl)pyridine 1-oxide, 1.05 g (43%).

b) 3-(4-(3,4-Dimethoxy-5-nitrophenyl)-3-(ethoxycarbonyl)furan-2-yl)-2-(trifluoro-methyl)pyridine-1-oxide (482 mg, 1 mmol) was taken up in dichloromethane (8 mL). The yellowish suspension was cooled to −78° C. under argon and boron tribromide (0.85 mL, 9 mmol) was added dropwise. The reddish reaction mixture was allowed to warm to room temperature and stirred for 18 hours and then carefully poured into ice-water (100 mL) and stirred for 1 hour. The yellow precipitate was filtered off, washed with water and dried over $P_2O_5$ under vacuum. Recrystallisation of the solid from ethanol gave 3-(4-(3,4-Dihydroxy-5-nitrophenyl)-3-(ethoxycarbonyl)furan-2-yl)-2-(trifluoromethyl)pyridine 1-oxide as a yellow solid, 0.31 g (68%).

EXAMPLE 56

As an example of a compound of the general formula (I) having a oxazol-2,4-diyl moiety as central unit, 3-(4-(3,4-dihydroxy-5-nitrophenyl)oxazol-2-yl)-2-(trifluoromethyl) pyridine 1-oxide was prepared by the following procedure:

a) To a solution of 2-(3,4-dimethoxy-5-nitrophenyl)-2-oxoethyl acetate (4.24 g, 15 mmol) in xylene (30 mL) were added 3-carbamoyl-2-(trifluoromethyl)pyridine 1-oxide (3.40 g, 16.5 mmol) and boron trifluoride etherate (0.18 mL, 15 mmol). The resulting yellow solution was heated to reflux for 18 hours and then cooled to room temperature. After evaporation of the solvent, the residue was partitioned between ethyl acetate and saturated aqueous sodium bicarbonate. The organic phase was separated, washed with brine and the dried over anhydrous magnesium sulphate, filtered and evaporated. The pure 3-(4-(3,4-dimethoxy-5-nitrophenyl)oxazol-2-yl)-2-(trifluoromethyl) pyridine 1-oxide was obtained by column chromatography over silica gel (petroleum ether/ethylacetate 2:1) as a pale yellow solid, 2.58 g (42%).

b) 3-(4-(3,4-Dimethoxy-5-nitrophenyl)oxazol-2-yl)-2-(trifluoromethyl)pyridine 1-oxide (1.23 g, 3 mmol) was taken up in dichloromethane (25 mL). The yellowish suspension was cooled to −78° C. under argon and boron tribromide (2.55 mL, 27 mmol) was added dropwise. The red reaction mixture was allowed to warm to room temperature and stirred for 18 hours. It was then carefully poured into ice-water (100 mL) and stirred for 1 hour. The resulting yellow precipitate was filtered off, washed with water and dried over $P_2O_5$ under vacuum. The solid was recrystallized from ethanol to give 3-(4-(3,4-dihydroxy-5-nitrophenyl)oxazol-2-yl)-2-(trifluoromethyl)pyridine 1-oxide as a yellow solid, 0.65 g, (57%).

EXAMPLE 57

As an example of a compound of the general formula (I) having a 1,2,4-triazin-3,5-diyl moiety as central unit, 3-(5-(3,4-dihydroxy-5-nitrophenyl)-1,2,4-triazin-3-yl)-2-(trifluoromethyl)pyridine 1-oxide was prepared by the following procedure:

a) To a stirred solution of (Z)-3-carbamohydrazonoyl-2-(trifluoromethyl) pyridine 1-oxide (1.10 g, 5 mmol) in ethanol (30 mL) was added 2-(3,4-dimethoxy-5-nitrophenyl)-2-oxoacetaldehyde (1.19 g, 5 mmol). The reaction mixture was heated to reflux for 5 hours, and then cooled to room temperature and the solvent was removed by evaporation. The residue was dissolved in dichloromethane (30 mL) and the organic phase was washed with water and dried over anhydrous magnesium sulphate, filtered and evaporated. The crude product was recrystallized from isopropanol to give 3-(5-(3.4-dimethoxy-5-nitrophenyl)-1,2,4-triazin-3-yl)-2-(trifluoromethyl)pyridine 1-oxide, 1.69 g (80%).

b) 3-(5-(3,4-dimethoxy-5-nitrophenyl)-1,2,4-triazin-3-yl)-2-(trifluoromethyl)pyridine 1-oxide (1.27 g, 3 mmol) was taken up in dichloromethane (25 mL). The yellowish solution was cooled to −78° C. under argon and boron tribromide (2.55 mL, 27 mmol) was added dropwise. The red reaction mixture was allowed to warm to room temperature and stirred for 18 hours. It was then carefully poured into ice-water (100 mL) and stirred for 1 hour. The yellow precipitate was filtered off, washed with water and dried over $P_2O_5$ under vacuum. The solid was recrystallised from dichloromethane-ethanol to give 3-(5-(3,4-dihydroxy-5-nitrophenyl)-1,2,4-triazin-3-yl)-2-(trifluoromethyl)pyridine 1-oxide as a yellow solid, 0.84 g (71%).

EXAMPLE 58

As an example of a compound of the general formula (I) having a 1,3,5-triazin-2,4-diyl moiety as central unit, 3-(4-(3,4-dihydroxy-5-nitrophenyl)-1,3,5-triazin-2-yl)-2-(trifluoromethyl)pyridine 1-oxide was prepared by the following procedure:

a) To a solution of (E)-N-((dimethylamino)methylene)-3,4-dimethoxy-5-nitrobenzamide (1.12 g, 4 mmol) ethanol (30 mL) was added 3-carbamimidoyl-2-(trifluoromethyl)pyridine 1-oxide (0.82 g, 4 mmol). The reaction mixture was heated to reflux for 5 hours. It was cooled to room temperature and the solvent was removed by evaporation. The residue was then dissolved in dichloromethane/isopropanol mixture (50 mL, 70:30) and the organic phase was washed with water, dried over anhydrous magnesium sulphate, filtered and evaporated. The crude product was recrystallized from ethanol to give 3-(4-(3,4-dimethoxy-5-nitrophenyl)-1,3,5-triazin-2-yl)-2-(trifluoromethyl)pyridine 1-oxide, 1.27 g (75%).

b) A portion of 3-(4-(3,4-dimethoxy-5-nitrophenyl)-1,3,5-triazin-2-yl)-2-(trifluoromethyl) pyridine 1-oxide (1.269 g, 3 mmol) was taken up in dichloromethane (25 mL). The yellowish solution was cooled to −78° C. under argon and boron tribromide (2.55 mL, 27 mmol) was added dropwise. The red reaction mixture was allowed to warm to room temperature and stirred for 18 hours and then carefully poured into ice-water (100 mL) and stirred for 1 hour. The yellow precipitate was filtered off, washed with water and dried over $P_2O_5$ under vacuum. Recrystallisation from a dichloromethane-ethanol mixture gave 3-(4-(3,4-dihydroxy-5-nitrophenyl)-1,3,5-triazin-2-yl)-2-(trifluoromethyl)pyridine 1-oxide as a yellow solid, 1.07 g (90%).

EXAMPLE 59

As an example of a compound of the general formula (I) having a pyrrol-2,5-diyl moiety as central unit, 5-(3,4-dihydroxy-5-nitrophenyl)-1-methyl-2-(2-trifluoromethyl-1-oxypyridin-3-yl)-1H-pyrrole-3-carboxylic acid ethyl ester was prepared by the following procedure:

a) To a stirred solution of methylamine (0.63 mL, 33% EtOH solution, 5 mmol) in a mixture of ethanol (25 mL) and acetic acid (0.5 mL) at room temperature was added 3-oxo-3-(1-oxy-2-trifluoromethyl-pyridin-3-yl)-propionic acid ethyl ester (1.39 g, 5 mmol). The reaction mixture was heated at reflux for two hours whereupon the solvent was removed by evaporation under vacuum. To a solution of the crude product in dimethylformamide (25 mL) was added potassium carbonate (2.07 g, 15 mmol) in one portion followed by 1-(3,4-bis-benzyloxy-5-nitro-phenyl)-2-bromoethanone (2.51 g, 5.50 mmol) and the mixture was then stirred at 100° C. Once no starting material was detectable by TLC, the reaction mixture was allowed to cool to room temperature and poured onto ice-cold 1 N aqueous hydrochloric acid (100 mL). The resulting precipitate was filtered off, washed with water and dried. The residue was chromatographed over silica gel. Homogeneous fractions were pooled and evaporated to give 5-(3,4-bis-benzyloxy-5-nitro-phenyl)-1-methyl-2-(2-trifluoromethyl-1-oxy-pyridin-3-yl)-1H-pyrrole-3-carboxylic acid ethyl ester, 2.41 g (79%).

b) A solution of 5-(3,4-bis-benzyloxy-5-nitro-phenyl)-1-methyl-2-(2-trifluoromethyl-1-oxy-pyridin-3-yl)-1H-pyrrole-3-carboxylic acid ethyl ester (0.2 g, 0.30 mmol) in dichloromethane (10 mL) was cooled to −78° C. with stirring and treated under argon with boron tribromide (0.30 g, 1.21 mmol). The resulting deep purple suspension was then allowed to stir at room temperature for one hour before cooling again to −78° C. The mixture was quenched by the careful addition of methanol. After stirring at room temperature for thirty minutes, the volatiles were evaporated and the residue stirred with 2 N hydrochloric acid (5 mL) for thirty minutes. The resulting solid was filtered off, washed with water (25 mL) and then cold isopropanol (5 mL) to give 5-(3,4-dihydroxy-5-nitro-phenyl)-1-methyl-2-(1-oxy-2-trifluoromethyl-pyridin-3-yl)-1H-pyrrole-3-carboxylic acid ethyl ester as a yellow solid, 0.13 g (93%).

EXAMPLE 60

As an example of a compound of the general formula (I) having a 2H-tetrazol-2,5-diyl moiety as central unit, 5-[2-(5-trifluoromethyl-1-oxy-pyridin-2-yl)-2H-tetrazol-5-yl]-3-nitrobenzene-1,2-diol was prepared by the following procedure:

a) A mixture of 3,4-bis-benzyloxy-5-nitro-benzonitrile (0.54 g, 1.50 mmol), sodium azide (0.15 g, 2.25 mmol) and ammonium chloride (0.12 g, 2.25 mmol) in dimethylformamide (3 mL) was stirred at 85° C. for 20 hours. After cooling to room temperature, the reaction mixture was poured onto water (30 mL) and acidified with dilute hydrochloric acid. The resulting precipitate was collected, washed with water and dried to yield 5-(3,4-bis-benzyloxy-5-nitro-phenyl)-2H-tetrazole, 0.53 g (87%).

b) 2-Chloro-5-trifluoromethyl-1-oxy-pyridine (0.20 g, 1.00 mmol) was added to a stirred suspension of 5-(3,4-bis-benzyloxy-5-nitro-phenyl)-2H-tetrazole (0.4 g, 1.00 mmol) and potassium carbonate (0.14 g, 1 mmol) in acetonitrile (10 mL). The reaction mixture was stirred at room temperature till completion, then diluted with dichloromethane and washed with water. The organic phase was separated, dried over anhydrous magnesium sulphate, filtered and evaporated to dryness to leave a crude residue that was recrystallised from a dichloromethane/isopropanol mixture to afford 2-[5-(3,4-bis-benzyloxy-5-nitro-phenyl)-tetrazol-2-yl]-5-trifluoromethyl-1-oxy-pyridine, 0.40 g (71%).

c) A solution of 2-[5-(3,4-bis-benzyloxy-5-nitro-phenyl)-tetrazol-2-yl]-5-trifluoromethyl-1-oxy-pyridine (0.282 g, 0.5 mmol) in dichloromethane (15 mL) was cooled to −78° C. with stirring under argon and treated with boron tribromide (1.00 g, 4.00 mmol) dropwise. The resulting deep purple suspension was then allowed to stir at room temperature for one hour before cooling again to −78° C. The mixture was quenched by the careful addition of methanol. After stirring at room temperature for thirty minutes, the volatiles were evaporated and the residue stirred with 2 N hydrochloric acid (5 mL) for thirty minutes. The resulting solid was filtered off, washed with water (25 mL) and then cold isopropanol (5 mL) to give 5-[2-(5-trifluoromethyl-1-oxy-pyridin-2-yl)-2H-tetrazol-5-yl]-3-nitrobenzene-1,2-diol as a yellow solid, 0.17 g, (90%).

EXAMPLE 61

As an example of a compound of the general formula (I) having a 1,3-thiazol-2,4-diyl moiety as central unit, 5-[2-

[2-(trifluoromethyl)-1-oxy-pyridin-3-yl]-[1,3]-thiazol-4-yl]-3-nitrobenzene-1,2-diol was prepared by the following procedure:

a) A mixture of 2-(trifluoromethyl)-1-oxy-pyridine-3-carbothioamide (0.24 g, 1.10 mmol) and 1-[3,4-bis(benzyloxy)-5-nitrophenyl]-2-bromoethanone (0.50 g, 1.10 mmol) were refluxed overnight in absolute ethanol (5 mL). After cooling to room temperature, the reaction mixture was poured onto water (50 mL). The resulting precipitate was filtered off, washed with water (25 mL) and dried. Recrystallisation from dichloromethane/isopropanol afforded 3-[4-(3,4-bis-benzyloxy-5-nitro-phenyl)-[1,3]-thiazol-2-yl]-2-trifluoromethyl-1-oxy-pyridine, 0.55 g (87%).

b) A solution of 3-[4-(3,4-bis-benzyloxy-5-nitro-phenyl)-[1,3]-thiazol-2-yl]-2-trifluoromethyl-1-oxy-pyridine (0.15 g, 0.26 mmol), in dichloromethane (10 mL) was cooled to −78° C. and treated under argon, with boron tribromide (0.26 g, 1.03 mmol). The resulting deep purple suspension was then allowed to stir at room temperature for one hour before cooling again to −78° C. The mixture was quenched by careful addition of methanol. After stirring at room temperature for thirty minutes, the volatiles were evaporated and the residue stirred with 2 N hydrochloric acid (5 mL) for thirty minutes. The resulting solid was filtered off, washed with water (25 mL) and then cold isopropanol (5 mL) to give 5-[2-[2-(trifluoromethyl)-1-oxy-pyridin-3-yl]-[1,3]-thiazol-4-yl]-3-nitrobenzene-1,2-diol as a yellow solid, 0.09 g (87%).

EXAMPLE 62

As an example of a compound of the general formula (I) having a 1,2,4-triazol-3,5-diyl moiety as central unit, 5-[4-methyl-5-(2-trifluoromethyl-1-oxy-pyridin-3-yl)-4H-[1,2,4]triazol-3-yl]-3-nitro-benzene-1,2-diol was prepared by the following procedure:

a) To a stirred solution of 3,4-dimethoxy-5-nitro-benzoyl chloride (0.50 g, 2.04 mmol) in dichloromethane (10 mL) at 0° C., was added dropwise methylamine (1.02 mL, 2.04 mmol, 2 M in THF). The reaction mixture was stirred at room temperature till all starting material disappeared, then diluted with dichloromethane and washed with water. The organic phase was dried over anhydrous magnesium sulphate, filtered and evaporated to dryness to leave a crude residue that was recrystallised from a dichloromethane/isopropanol mixture to afford 3,4-dimethoxy-N-methyl-5-nitro-benzamide, 0.44 g (89%).

b) To a stirred suspension of 3,4-dimethoxy-N-methyl-5-nitro-benzamide (0.40 g, 1.66 mmol) in toluene (10 mL) was added phosphorous pentachloride (0.38 g, 1.83 mmol) portionwise. Upon completion of addition, the reaction mixture was warmed to reflux till complete disappearance of starting material. Evaporation to dryness resulted in a crude solid that was washed with diethyl ether, affording 3,4-dimethoxy-N-methyl-5-nitro-benzimidoyl chloride, 0.37 g (85%).

c) A mixture of 2-trifluoromethyl-1-oxy-3-pyridinecarbonitrile (0.47 g, 2.50 mmol), sodium azide (0.24 g, 3.75 mmol) and ammonium chloride (0.20 g, 3.75 mmol) in dimethylformamide (2.5 mL) was stirred at 85° C. for 20 hours. After cooling to room temperature, the reaction mixture was poured onto water (20 mL) and acidified with dilute hydrochloric acid. The resulting precipitate was collected, washed with water and dried to yield 3-(2H-tetrazol-5-yl)-2-trifluoromethyl-1-oxy-pyridine, 0.52 g (90%).

d) 3,4-Dimethoxy-N-methyl-5-nitro-benzimidoyl chloride (0.26 g, 1.08 mmol) was added to a stirred solution of 3-(2H-tetrazol-5-yl)-2-trifluoromethyl-1-oxy-pyridine (0.23 g, 1 mmol) in dry pyridine (3 mL), preheated to 50° C. The resulting mixture was cautiously heated to 75-90° C. and maintained at this temperature until nitrogen evolution ceased. The mixture was then poured onto water (30 mL) and extracted with dichloromethane (25 mL). The organic phase was separated, dried over anhydrous magnesium sulphate, filtered and evaporated to dryness. The resulting residue was purified by chromatography to afford 3-[5-(3,4-dimethoxy-5-nitro-phenyl)-4-methyl-4H-[1,2,4]triazol-3-yl]-2-trifluoromethyl-1-oxy-pyridine, 0.25 g (59%).

e) To a stirred suspension of 3-[5-(3,4-dimethoxy-5-nitro-phenyl)-4-methyl-4H-[1,2,4]triazol-3-yl]-2-trifluoromethyl-1-oxy-pyridine (0.20 g, 0.47 mmol) in dichloromethane (20 mL) at −78° C. under argon was added boron tribromide (0.47 g, 1.88 mmol) dropwise. The resulting purple suspension was then allowed to stir at room temperature for seven hours before being cooled in an ice-water bath. The mixture was carefully quenched by the addition of methanol. After stirring at room temperature for thirty minutes, the volatiles were evaporated and the residue stirred with 2 N hydrochloric acid (5 mL) for thirty minutes. The resulting solid was filtered off, washed with water (25 mL) and then cold isopropanol (5 mL) to give, after drying, 5-[4-Methyl-5-(2-trifluoromethyl-1-oxy-pyridin-3-yl)-4H-[1,2,4]triazol-3-yl]-3-nitro-benzene-1,2-diol was obtained as an orange solid, 0.16 g (86%).

EXAMPLE 63

As an example of a compound of the general formula (I) having a 1,2,3-thiadiazol-4,5-diyl moiety as central unit, 5-[5-(2-trifluoromethyl-1-oxy-pyridin-3-yl)-[1,2,3]thiadiazol-4-yl]-3-nitrobenzene-1,2-diol was prepared by the following procedure:

a) A mixture of 1-(3,4-bis-benzyloxy-5-nitro-phenyl)-2-(2-trifluoromethyl-1-oxy-pyridin-3-yl)-ethanone (0.50 g, 0.93 mmol), ethyl carbazate (0.11 g, 1.06 mmol) and p-toluenesulfonic acid (4 mg) in toluene (10 mL) was refluxed until azeotropic distillation of water ceased. The reaction mixture was cooled to room temperature, the solvents were evaporated to dryness, and the crude solid was triturated with diethyl ether (15 mL), filtered and dried yielding N'-[1-(3,4-bis-benzyloxy-5-nitro-phenyl)-2-(2-trifluoromethyl-1-oxy-pyridin-3-yl)-ethylidene]-hydrazinecarboxylic acid ethyl ester, 0.49 g (84%).

b) A mixture of N'-[1-(3,4-bis-benzyloxy-5-nitro-phenyl)-2-(2-trifluoromethyl-1-oxy-pyridin-3-yl)-ethylidene]-hydrazinecarboxylic acid ethyl ester (0.40 g, 0.64 mmol), in thionyl chloride (2 mL) was refluxed until no more starting material was detected by TLC. Excess of solvent was removed and the residue was purified by chromatography over silica gel using a mixture of dichloromethane/ethanol as eluent. Homogeneous fractions were pooled and evaporated to afford 3-[4-(3,4-bis-benzyloxy-5-nitro-phenyl)-[1,2,3]thiadiazol-5-yl]-2-trifluoromethyl-1-oxy-pyridine, 0.19 g (51%).

c) A solution of 3-[4-(3,4-bis-benzyloxy-5-nitro-phenyl)-[1,2,3]thiadiazol-5-yl]-2-trifluoromethyl-1-oxy-pyridine (0.15 g, 0.26 mmol) in dichloromethane (10 mL) was cooled to −78° C. with stirring and treated under argon with boron tribromide (0.26 g, 1.03 mmol). The resulting deep purple suspension was then allowed to stir at room temperature for one hour before cooling again to −40° C. The mixture was quenched by the careful addition of methanol. After stirring at room temperature for thirty minutes, the volatiles were evaporated and the residue stirred with 2 N hydrochloric acid (5 mL) for thirty minutes. The resulting solid was filtered off, washed with water (25 mL) and then cold isopropanol (5 mL) to give 5-[5-(2-trifluoromethyl-1-oxy-pyridin-3-yl)-[1,2,3]thiadiazol-4-yl]-3-nitrobenzene-1,2-diol as a yellow solid, 0.09 g (89%).

EXAMPLE 64

As an example of a compound of the general formula (I) having a 1,2,4-oxadiazol-3,5-diyl moiety as central unit, 5-[5-[2-(trifluoromethyl)-1-oxypyridin-3-yl]-[1,2,4]-oxadiazol-3-yl]-3-nitrobenzene-1,2-diol was prepared by the following procedure:

a) To a stirred solution of 2-trifluoromethyl nicotinic acid (0.38 g, 2 mmol) in dimethylformamide (10 mL) at room temperature was added 1,1-carbonyldiimidazole (0.34 g, 2.10 mmol) in one portion. The resulting yellow mixture was allowed to stir for ninety minutes whereupon 3,4-bis(benzyloxy)-N'-hydroxy-5-nitrobenzamidine (0.79 g, 2 mmol) was added in one portion. The resulting mixture was stirred at room temperature for two hours and then poured onto water (100 mL). The resulting precipitate was filtered off, washed with water and dried. After recrystallisation from dichloromethane/isopropanol 3,4-bis(benzyloxy)-5-nitro-N'-(2-(trifluoromethyl)nicotinoyloxy)benzimidamide was obtained, as a light yellow solid, 0.88 g (78%).

b) To a stirred solution of the solid obtained above (0.26 g, 0.46 mmol) in tetrahydrofuran (15 mL) at room temperature under argon was added a 1 N solution of tetrabutylammonium fluoride in tetrahydrofuran (0.7 mL, 0.7 mmol). The resulting clear yellow solution was allowed to stir at room temperature for four hours. Additional tetrabutylammonium fluoride (0.7 mmol) was added and the reaction mixture was allowed to stir for fifteen hours at room temperature and then ten hours at 55° C. After cooling to room temperature, the reaction mixture was poured onto water (150 mL). The resulting precipitate was filtered off, washed with water and dried. The crude product was chromatographed over silica gel using dichloromethane as eluent. Homogeneous fractions were pooled and evaporated to afford 3-[3-[3,4-bis(benzyloxy)-5-nitrophenyl]-[1,2,4]-oxadiazol-5-yl]-2-(trifluoromethyl)pyridine as an off-white solid, 0.21 g (82%).

c) To a stirred solution of 3-[3-[3,4-bis(benzyloxy)-5-nitrophenyl]-[1,2,4]-oxadiazol-5-yl]-2-(trifluoromethyl) pyridine (0.33 g, 0.60 mmol) in dichloromethane (6 mL) at 0° C. was added urea hydrogen peroxide complex (0.28 g, 3 mmol) and trifluoroacetic anhydride (0.43 mL, 3.00 mmol). After the reaction mixture had been stirred at room temperature for 60 hours, solid residues were filtered off. The organic phase was then successively treated with an aqueous solution of $Na_2S_2O_5$ (0.6 g, 3.45 mmol, dissolved in 20 mL of water), 0.4 N hydrochloric acid (20 mL), a saturated solution of $NaHCO_3$ (20 mL), water (20 mL) and brine (20 mL). The organic phase was dried over anhydrous magnesium sulphate, filtered and evaporated to dryness. The residue was chromatographed over silica gel using dichloromethane/ethanol as eluent. Homogeneous fractions were pooled and evaporated, and the residue was recrystallised from dichloromethane/isopropanol to afford 3-[3-[3,4-bis(benzyloxy)-5-nitrophenyl]-[1,2,4]-oxadiazol-5-yl]-2-(trifluoromethyl)-1-oxy-pyridine as a yellow solid, 0.23 g (68%).

d) A solution of 3-[3-[3,4-bis(benzyloxy)-5-nitrophenyl]-[1,2,4]-oxadiazol-5-yl]-2-(trifluoromethyl)-1-oxy-pyridine (0.10 g, 0.18 mmol) in dichloromethane (5 mL) was cooled to −78° C. with stirring under argon and treated with boron tribromide (0.18 g, 0.74 mmol) dropwise. The resulting deep purple suspension was then allowed to stir at room temperature for one hour before cooling again to −78° C. The mixture was quenched by the careful addition of methanol. After stirring at room temperature for thirty minutes, the volatiles were evaporated and the residue stirred with 2 N hydrochloric acid (5 mL) for thirty minutes. The resulting solid was filtered off, washed with water (25 mL) and then cold isopropanol (5 mL) to give 5-[5-[2-(trifluoromethyl)-1-oxypyridin-3-yl]-[1,2,4]-oxadiazol-3-yl]-3-nitrobenzene-1,2-diol as a yellow solid, 0.06 g (88%).

The invention claimed is:

1. A process for the preparation of compounds according to formula I,

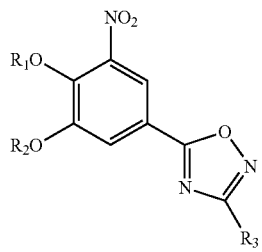

I wherein $R_1$ and $R_2$ independently from each other represent hydrogen, optionally substituted lower alkanoyl or optionally substituted lower aroyl;

$R_3$ represents a pyridine N-oxide group according to the formula A, B or C, which is connected as indicated by the unmarked bond:

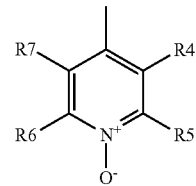

A

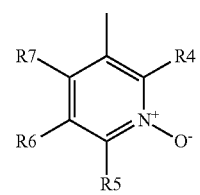

B

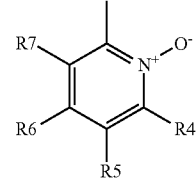

C comprising steps wherein a compound of formula IIA, IIB or IIC,

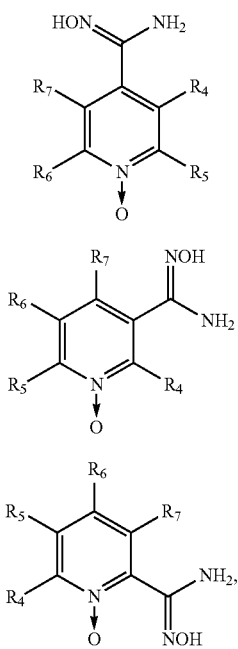

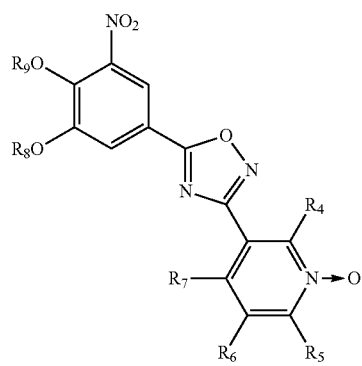

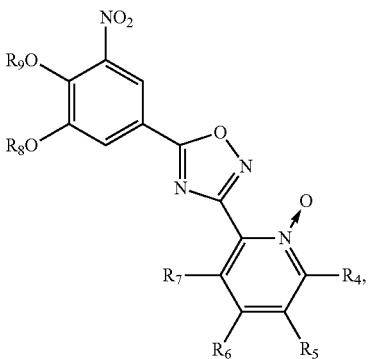

wherein $R_4$, $R_5$, $R_6$ and $R_7$ independently from each other represent hydrogen, $C_1$-$C_6$-alkyl, $C_1$-$C_6$-thioalkyl, $C_1$-$C_6$-alkoxy, $C_6$-$C_{12}$-aryloxy, a $C_6$-$C_{12}$-thioaryl group, $C_1$-$C_6$-alkanoyl, a $C_7$-$C_{13}$-aroyl group, amino, $C_1$-$C_6$-alkylamino, $C_1$-$C_6$-dialkylamino, $C_3$-$C_{12}$-cycloalkylamino, $C_3$-$C_{12}$-heterocycloalkylamino, $C_1$-$C_6$-alkylsulphonyl, $C_6$-$C_{12}$-arylsulphonyl, halogen, $C_1$-$C_6$-haloalkyl, trifluoromethyl, cyano, nitro or a heteroaryl group; or where two or more of residues $R_4$, $R_5$, $R_6$ and $R_7$ taken together represent aliphatic or heteroaliphatic rings or aromatic or heteroaromatic rings, is subjected to cyclisation with a compound of formula III,

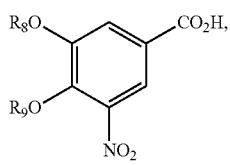

wherein $R_8$ and $R_9$ independently from each other represent hydrogen or suitable protective groups for aromatic hydroxyl groups, under conditions suitable to produce oxadiazole derivatives of formula IVA, IVB or IVC,

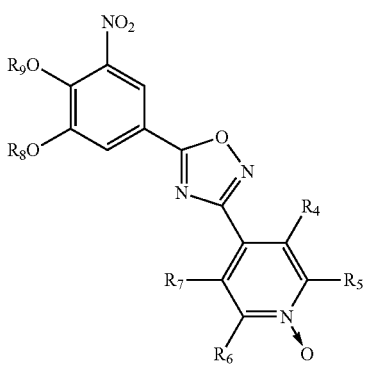

optionally followed by removal of the protecting groups $R_8$ and or $R_9$.

2. A process for the preparation of compounds according to formula I,

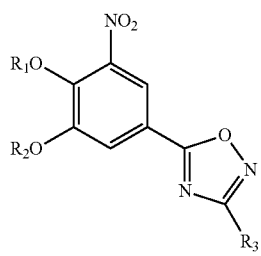

wherein
$R_1$ and $R_2$ independently from each other represent hydrogen, optionally substituted lower alkanoyl or optionally substituted lower aroyl;
$R_3$ represents a pyridine group according to the formula A, B or C, which is connected as indicated by the unmarked bond:

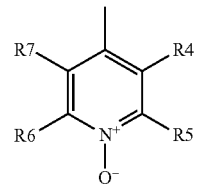

-continued

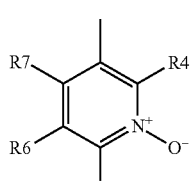
B

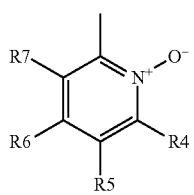
C comprising steps wherein a compound of formula VA, VB, or VC,

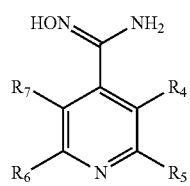
VA

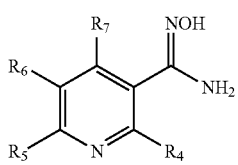
VB

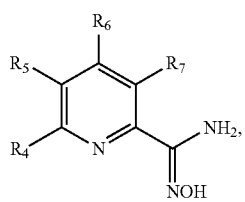
VC wherein $R_4$, $R_5$, $R_6$ and $R_7$ independently from each other represent hydrogen, $C_1$-$C_6$-alkyl, $C_1$-$C_6$-thioalkyl, $C_1$-$C_6$-alkoxy, $C_6$-$C_{12}$-aryloxy, a $C_6$-$C_{12}$-thioaryl group, $C_1$-$C_6$-alkanoyl, a $C_7$-$C_{13}$-aroyl group, amino, $C_1$-$C_6$-alkylamino, $C_1$-$C_6$-dialkylamino, $C_3$-$C_{12}$-cycloalkylamino, $C_3$-$C_{12}$-heterocycloalkylamino, $C_1$-$C_6$-alkylsulphonyl, $C_6$-$C_{12}$-arylsulphonyl, halogen, $C_1$-$C_6$-haloalkyl, trifluoromethyl, cyano, nitro or a heteroaryl group; or where two or more of residues $R_4$, $R_5$, $R_6$ and $R_7$ taken together represent aliphatic or heteroaliphatic rings or aromatic or heteroaromatic rings, is subjected to cyclisation with a compound of formula III

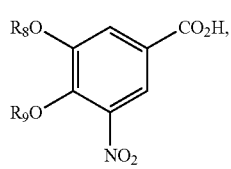
(III)

under conditions suitable to produce oxadiazole derivatives of formula VIA, VIB or VIC,

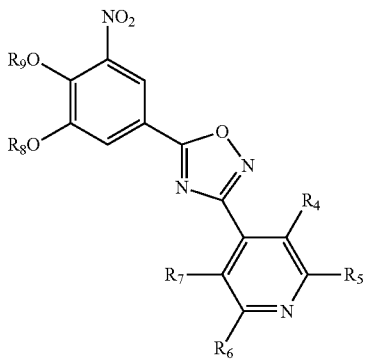
VIA

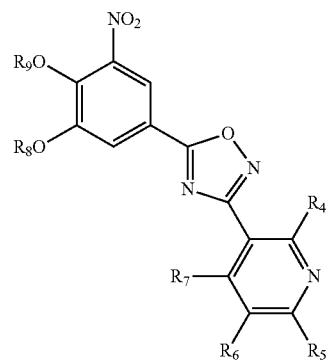
VIB

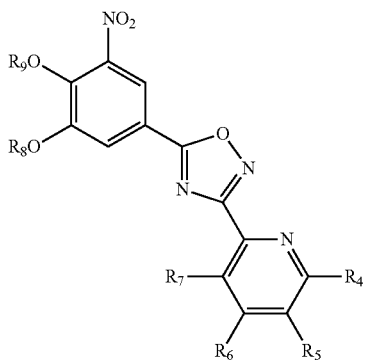
VIC followed by oxidation of the pyridyl nitrogen atom to give a compound according to formula IVA, IVB or IVC,

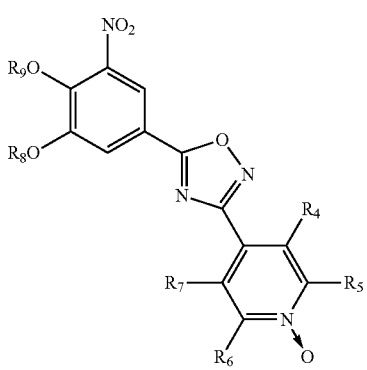
IVA

-continued

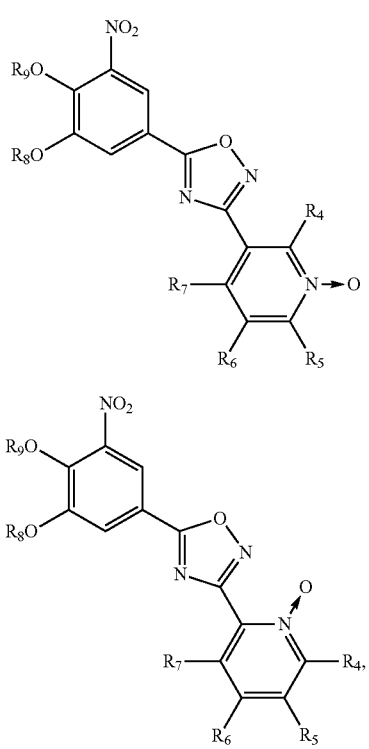

optionally followed by removal of the protecting groups $R_8$ and/or $R_9$, wherein $R_8$ and $R_9$ independently from each other represent hydrogen or suitable protective groups for aromatic hydroxyl groups.

3. The process according to claim 1, wherein the compound of formula III is activated by reaction with thionyl chloride or 1,1-carbonyldiimidazole.

4. The process according to claim 1, wherein the cyclisation step consisting of condensation and dehydration is conducted sequentially in a one-pot reaction.

5. The process according to claim 1, wherein the cyclisation step is carried out in the presence of a suitable organic base.

6. The process according to claim 5, wherein the cyclisation step is carried out in the presence of pyridine.

7. The process according to claim 1, wherein the groups $R_8$ and $R_9$ are independently from each other or jointly removed and replaced with hydrogen.

8. The process according to claim 1, wherein $R_8$ and $R_9$ of the compound of formula III independently from each other represent methyl or hydrogen.

9. The process according to claim 8, wherein the methyl group is removed by reaction with aluminium chloride and pyridine in N-methylpyrrolidinone.

10. The process according to claim 1, wherein the condensation and dehydration is performed in a dipolar aprotic solvent.

11. The process according to claim 10, wherein the condensation and dehydration is performed in dimethylacetamide, N-methylpyrrolidinone, or dimethylsulfoxide.

12. The process according to claim 2, wherein the pyridyl nitrogen atom of the oxadiazolyl compound of formula VIA, VIB or VIC is oxidised by hydrogen peroxide, peracetic acid, trifluoroperacetic acid, or urea-hydrogen peroxide complex and trifluoroacetic anhydride.

13. The process according to claim 1, wherein the compound of formula IIA, IIB or IIC is obtained by the reaction of compound VIIA, VIIB, or VIIC, respectively,

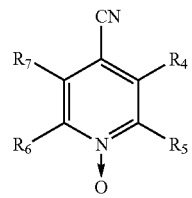

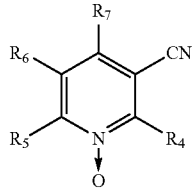

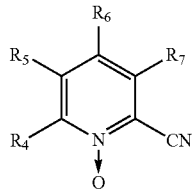

wherein $R_4$, $R_5$, $R_6$, and $R_7$ are defined as in the general formula I in claim 1, with hydroxylamine in the presence of a chelating agent under conditions suitable to produce amidoxime derivatives.

14. The process according to claim 2, wherein the compound of formula VA, VB or VC is obtained by the reaction of compound VIIIA, VIIIB or VIIIC, respectively,

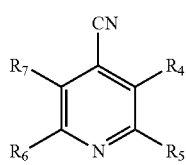

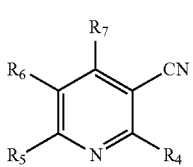

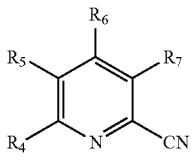

wherein $R_4$, $R_5$, $R_6$ and $R_7$ are defined as in the general formula I in claim 2, with hydroxylamine in the presence of a chelating agent under conditions suitable to produce amidoxime derivatives.

15. The process according to claim 13, wherein the chelating agent is selected from the group consisting of 8-hydroxyquinoline, ortho-phenanthroline and hydrates or derivatives thereof.

16. Process for the preparation of compounds according to formula I in claim 1, comprising the oxidation of the respective pyridine compound to the pyridine N-oxide compound.

* * * * *